(12) United States Patent
Elands et al.

(10) Patent No.: US 12,419,964 B2
(45) Date of Patent: Sep. 23, 2025

(54) ANTIBODY DRUG CONJUGATE (ADC) TARGETING NECTIN 4 AND COMPRISING AN EXATECAN PAYLOAD

(71) Applicants: ELI LILLY AND COMPANY, Indianapolis, IN (US); UNIVERSITÉ D'AIX-MARSEILLE, Marseilles (FR); INSERM (Institut National De La Sante Et De La Recherche Medicale), Paris (FR); INSTITUT JEAN PAOLI & IRENE CALMETTES, Marseilles (FR); CENTRE NATIONAL DE LA RECHERCHE SCIENTIFIQUE—CNRS, Paris (FR); MABLINK BIOSCIENCE, Lyons (FR); UNIVERSITE CLAUDE BERNARD LYON, Villeurbanne (FR)

(72) Inventors: Jacobus Petrus Maria Elands, Forest (BE); Joanna Fares, Aix-en-Provence (FR); Guy Fournet, Lyons (FR); Benoit Joseph, Villeurbanne (FR); Florence Lhospice, Bretagne (FR); Marc Lopez, Marseilles (FR); Daniel Olive, Marseilles (FR); Xavier Preville, Roquefort les Pins (FR); Warren Viricel, Sainte Consorce (FR)

(73) Assignees: ELI LILLY AND COMPANY, Indianapolis, IN (US); UNIVERSITÉ D'AIX-MARSEILLE, Marseilles (FR); INSERM (Institut National De La Sante Et De La Recherche Medicale), Paris (FR); INSTITUT JEAN PAOLI & IRENE CALMETTES, Marseilles (FR); CENTRE NATIONAL DE LA RECHERCHE SCIENTIFIQUE—CNRS, Paris (FR); MABLINK BIOSCIENCE, Lyons (FR); UNIVERSITE CLAUDE BERNARD LYON, Villeurbanne (FR)

( * ) Notice: Subject to any disclaimer, the term of this patent is extended or adjusted under 35 U.S.C. 154(b) by 0 days.

(21) Appl. No.: 18/904,628

(22) Filed: Oct. 2, 2024

(65) Prior Publication Data
US 2025/0127916 A1  Apr. 24, 2025

(30) Foreign Application Priority Data
Oct. 2, 2023  (EP) .................................... 23201214

(51) Int. Cl.
*A61K 47/68* (2017.01)
*A61P 35/00* (2006.01)

(52) U.S. Cl.
CPC .... *A61K 47/68037* (2023.08); *A61K 47/6849* (2017.08); *A61K 47/6889* (2017.08); *A61P 35/00* (2018.01)

(58) Field of Classification Search
None
See application file for complete search history.

(56) References Cited

U.S. PATENT DOCUMENTS

| 12,049,500 B2 | 7/2024 | Elands et al. |
| 2013/0144045 A1 | 6/2013 | Papot et al. |

(Continued)

FOREIGN PATENT DOCUMENTS

| EP | 2305214 A1 | 4/2011 |
| EP | 3347048 A0 | 3/2017 |

(Continued)

OTHER PUBLICATIONS

GenCore version 6.4.4 Copyright (c) 1993-2024 Biocceleration Ltd., entry AC BLW71217, WO2022207822-A1, Anti-nectin-4 humanized antibody back-mutated VH (Year: 2022).*

(Continued)

*Primary Examiner* — Karl J Puttlitz
(74) *Attorney, Agent, or Firm* — M. Scott McBride

(57) ABSTRACT

The present disclosure provides Nectin-4 antibody drug conjugates (ADCs) comprising exatecan and pharmaceutical (Continued)

compositions thereof, and methods of using the ADCs for the treatment of cancer.

11 Claims, 18 Drawing Sheets

Specification includes a Sequence Listing.

(56) References Cited

U.S. PATENT DOCUMENTS

| | | | |
|---|---|---|---|
| 2020/0345863 | A1 | 11/2020 | Viricel |
| 2024/0034791 | A1 | 2/2024 | Elands et al. |
| 2024/0173424 | A1 | 5/2024 | Elands et al. |
| 2024/0216525 | A1 | 7/2024 | Viricel et al. |

FOREIGN PATENT DOCUMENTS

| | | | | |
|---|---|---|---|---|
| EP | 3546448 | A1 | 2/2019 | |
| WO | 2011145068 | A1 | 11/2011 | |
| WO | 2013050617 | A1 | 4/2013 | |
| WO | 2014093394 | A1 | 6/2014 | |
| WO | 2015031693 | A1 | 3/2015 | |
| WO | 2015038426 | A1 | 3/2015 | |
| WO | 2015057699 | A2 | 4/2015 | |
| WO | 2016059377 | A1 | 4/2016 | |
| WO | 2017042210 | A1 | 3/2017 | |
| WO | 2017057653 | A1 | 6/2017 | |
| WO | 2017089895 | A1 | 6/2017 | |
| WO | 2018158398 | A1 | 9/2018 | |
| WO | 2018226578 | A1 | 12/2018 | |
| WO | 2019081455 | A1 | 5/2019 | |
| WO | 2021069508 | A1 | 4/2021 | |
| WO | 2021143741 | A1 | 7/2021 | |
| WO | 2021151984 | A1 | 8/2021 | |
| WO | 2021213434 | A1 | 10/2021 | |
| WO | 2022207699 | A1 | 10/2022 | |
| WO | WO-2022207822 | A1 * | 10/2022 | ......... A61K 47/6803 |
| WO | WO-2022207825 | A1 * | 10/2022 | ......... A61K 47/6803 |
| WO | WO-2022207828 | A1 * | 10/2022 | ......... A61K 47/6803 |
| WO | WO-2023170247 | A1 * | 9/2023 | ....... A61K 47/68037 |
| WO | WO-2024017992 | A1 * | 1/2024 | ............. A61P 35/00 |
| WO | 2024038075 | A1 | 2/2024 | |

OTHER PUBLICATIONS

GenCore version 6.4.4 Copyright (c) 1993-2024 Biocceleration Ltd., entry AC BLW71162, WO2022207822-A1, Anti-nectin-4 humanized antibody back-mutated VL (Year: 2022).*
See also GenCore version 6.4.4 Copyright (c) 1993-2024 Biocceleration Ltd., entry AC BOP64493, WO2024017992-A1, Anti-nectin-4 monoclonal antibod heavy chain (Year: 2022).*
GenCore version 6.4.4 Copyright (c) 1993-2024 Biocceleration Ltd., entry AC BOP64494, WO2024017992-A1, Anti-nectin-4 humanized antibody back-mutated VL (Year: 2022).*
Azim et al., Abstract B128: Preclinical characterization of ETx-22, a next-generation antibody drug Conjugate (ADC) targeting nectin-4; Mol Cancer Ther (2023) 22 (12_Supplement): B128., Dec. 1, 2023, Proceedings of the AACR-NCI-EORTC Virtual International Conference on Molecular Targets and Cancer Therapeutics; Oct. 11-15, 2023.
Bargh et al., Chem. Soc. Rev., 2019, 48, 4361-4371.
Burke et al., "Campthothecins in Cancer Therapy," 2005 Humana Press, pp. 317-341.
Challita-Eid et al., Cancer Res; 76(10) May 15, 2016, 3003-3013.
Conilh et al., Pharmaceuticals 2021, 14, 247.
Dobry et al., JAAD Case Reports 2021;14;7-9.
Extended European Search Report for EP23201214.6, issued Mar. 25, 2024.
Hirotsu et al., J Am Acad Dermatology, Dec. 2021, 1610-1611.
IPRP for PCT/EP2018/078949, Apr. 28, 2020.
IPRP for PCT/EP2020/078146, Apr. 12, 2022.
IPRP for PCT/EP2022/058402, Oct. 3, 2023.
IPRP for PCT/EP2022/058626, Jun. 27, 2023.
IPRP for PCT/EP2022/058629, Oct. 3, 2023.
Iris Biotech, Polysarcosine—a True Alternative to PEG, Feb. 7, 2017 Updated at Oct. 4, 2022.
ISR for PCT/EP2018/078949, completed Jan. 8, 2019.
ISR for PCT/EP2020/078146, completed Jan. 12, 2021.
ISR for PCT/EP2022/058402, completed Jul. 7, 2022.
ISR for PCT/EP2022/058626, completed May 30, 2022.
ISR for PCT/EP2022/058629, completed Jul. 15, 2022.
ISR for PCT/EP2023/056097, completed Jun. 7, 2023.
ISR for PCT/EP2024/072528, completed Nov. 22, 2023.
Jeong et al., Xenobiotica. Jan. 2008 ; 38(1): 62-75.
Lau et al., Langmuir. Nov. 20, 2012; 28(46): 16099-16107.
Lyon et al., Nature Biotechnology, vol. 33, No. 7, Jul. 2015, 733-736.
Rosenberg et al., Abstract CT084: A phase 1 study of LY4101174 (ETx-22), an antibody-drug conjugate targeting nectin-4, in patients with advanced or metastatic urothelial cancer and other solid tumors (trial in progress). Cancer Res (2024) 84 (7_Supplement): CT084. Apr. 5, 2024, Proceedings of the American Association for Cancer Research Annual Meeting 2024; Part 2 (Late-Breaking, Clinical Trial, and Invited Abstracts); Apr. 5-10, 2024.
Shim, Hyunbo, Biomolecules, 10, 360.
WO for PCT/EP2018/078949, May 2, 2019.
WO for PCT/EP2020/078146, Apr. 15, 2021.
WO for PCT/EP2022/058402, Oct. 6, 2022.
WO for PCT/EP2022/058626, Oct. 6, 2022.
WO for PCT/EP2022/058629, Oct. 6, 2022.
WO for PCT/EP2023/056097, Sep. 14, 2023.
WO for PCT/EP2024/072528, Feb. 22, 2024.
WO Response for PCT/EP2022/058626, Dec. 5, 2022.
Wu et al., Dermatology Online Journal, vol. 15 No. 2| Feb. 2019 24(2): 6.
Wu et al., J. Mol. Biol. (1999) 294, 151-162.
Zuckermann et al., J. Am. Chem. Soc. 1992, 114, 10646-10647.
International Search Report and Written Opinion issued by the European Patent Office for International Application No. PCT/EP2024/077813 mailed on Jan. 15, 2025, 14 pages.

* cited by examiner

ANTIBODY DRUG CONJUGATE (ADC) TARGETING NECTIN 4 AND COMPRISING AN EXATECAN PAYLOAD

REFERENCE TO A SEQUENCE LISTING

The present application is being filed along with a Sequence Listing in ST.26 XML format. The Sequence Listing is provided as a file titled "txt_P30825_FR" created Sep. 27, 2023 and is 7,935 bytes in size. The Sequence Listing information in the ST.26 XML format is incorporated herein by reference in its entirety.

BACKGROUND

The disclosure relates to the field of medicine. More particularly, the disclosure relates to Nectin-4 antibody drug conjugates and pharmaceutical compositions thereof, and their use in treating cancer.

Nectin-4 is a member of the Nectin family of Ca2+ independent immunoglobulin-like cellular adhesion molecules. Unlike others in the Nectin family, Nectin-4 expression in healthy tissue is largely placental or embryonic, but Nectin-4 is overexpressed in several tumor types, including urothelial, breast, lung, gastric, esophageal, colorectal, pancreatic, and ovarian cancer. Studies have connected high Nectin-4 expression with tumor occurrence in several cancer types.

Antibody drug conjugates (ADC) comprising anti Nectin-4 antibodies have been created. These include ADCs comprising a monomethyl auristatin E (MMAE) payload (WO201247724), ADCs with camptothecin analog payloads (WO2022112356 and WO2021151984), and ADCs comprising an exatecan payload (WO2022207825).

ADCs for use in oncology are very challenging compounds to design since multiple aspects of the molecule must be balanced, including, sufficient specificity for the tumor target over healthy cells, acceptable toxicity while maintaining desirable activity against bystander tumor cells, and controlled lability of payloads to allow intracellular delivery yet maintain good physical and chemical stability. In particular, one of the challenges in the development of ADCs is selecting a suitable linker with which to conjugate a payload to the antibody of the ADC. The chemical structure of a linker affects various properties of the ADC including toxicity, specificity, stability, and potency.

There currently is one FDA-approved anti-Nectin-4 ADC, which is enfortumab vedotin-ejfv marketed under the brand name PADCEV®. Enfortumab vedotin is an ADC comprising a monoclonal anti-Nectin-4 antibody and monomethyl auristatin-E (MMAE) as a cytotoxic payload. Unfortunately, enfortumab vedotin exhibits some undesirable skin-toxicity which may be at least partially associated with the nondiscriminate binding of enfortumab to skin cells as opposed to targeted tumor cells. In addition, long-term administration of enfortumab vedotin may result in the occurrence of drug-resistant cancer in human patients. Cabaud et al. (Mol Cancer Ther 21 (2022):1227-1235) found an upregulation in resistant tumors of ABCB1 expression encoding the multidrug resistance protein MDR1/P-glycoprotein (P-gp) in a preclinical mouse model. Sensitivity to an anti-Nectin-4 antibody-MMAE conjugate of the resistant mouse model could be restored in vitro and in vivo by the P-gp inhibitor tariquidar.

In particular, a need remains for anti-Nectin-4 ADCs that comprise a topoisomerase I payload. In particular, a need remains for anti-Nectin-4 ADCs that avoid or allow for better management of dermatological events seen in certain anti-Nectin-4 ADCs. In particular, a need remains for anti-Nectin-4 ADCs that avoid ocular and/or peripheral neuropathy signals seen in certain anti-Nectin-4 ADCs. In particular, a need remains for anti-Nectin-4 ADCs that have low immunogenicity, stable in vivo pharmacokinetics, and adequate chemical and physical stability. Additionally, a need remains for anti-Nectin-4 ADCs that possess one or more of the following features: improved anti-tumor activity as measured in certain tumor models, enhanced bystander activity for Nectin-4 low tumors, lower immunogenicity, no measurable antibody effector function, and/or better physical and chemical stability.

Here, the inventors disclose a novel anti-Nectin-4 ADC that addresses one or more these needs. The disclosed ADC comprises an anti-Nectin-4 antibody that exhibits selectivity for tumor-expressed Nectin-4 and a novel linker-payload comprising exatecan. The inventors show that the disclosed anti-Nectin-4 ADC exhibits one or more of these improved properties related to aggregation, toxicity, specificity, stability, and potency. The inventors also show that the novel anti-Nectin-4 ADC can be used to treat auristatin-resistant cancer, including cancer that is resistant to treatment with enfortumab vedotin

SUMMARY

Provided herein are anti-Nectin-4 ADCs and compositions comprising anti-Nectin-4 ADCs. Also provided herein are methods of using the anti-Nectin-4 ADCs or compositions comprising the anti-Nectin-4 ADCs for treating cancer in a patient, such as cancer that expresses Nectin-4.

In one aspect, provided herein is an ADC comprising an antibody that binds human Nectin-4, and a payload. In one aspect, provided herein is an ADC prepared by conjugating an antibody that binds human Nectin-4 to a payload. In the ADC, the antibody and payload are covalently bound or conjugated either directly or via a linker. In one aspect of the disclosed ADC, the antibody and payload are covalently bound or conjugated via a linker. In one aspect, the linker provides suitable stabile binding or conjugation between the antibody and the payload when the ADC is administered systemically, and the linker provides suitable lability when the ADC is internalized by a target cell that expresses Nectin-4 such that the payload is released from the ADC.

In one aspect, provided herein is an ADC comprising or prepared from an antibody that binds human Nectin-4, wherein the antibody comprises a heavy chain variable region (HCVR) and a light chain variable region (LCVR), wherein the HCVR comprises heavy chain complementarity determining regions (HCDR) HCDR1, HCDR2, and HCDR3, and the LCVR comprises light chain complementarity determining regions (LCDR) LCDR1, LCDR2, and LCDR3, wherein (a) the HCDR1 comprises SEQ ID NO: 9 (NYGMA), the HCDR2 comprises SEQ ID NO: 10 (FISNLAYGINYADTVTG), the HCDR3 comprises SEQ ID NO: 11 (GARATGWFAY), the LCDR1 comprises SEQ ID NO: 12 (KASQNVDTHVA), the LCDR2 comprises SEQ ID NO: 13 (SASYRYS), and the LCDR3 comprises SEQ ID NO: 14 (QQYNSYPLT) (all Kabat numbering); or (b) the HCDR1 comprises SEQ ID NO: 15 (GFTFSNYG), the HCDR2 comprises SEQ ID NO: 16 (ISNLAYGI), the HCDR3 comprises SEQ ID NO: 17 (ARGARATGWFAY), the LCDR1 comprises SEQ ID NO: 18 (QNVDTH), the LCDR2 comprises SEQ ID NO: 19 (SAS), and the LCDR3 comprises SEQ ID NO: 20 (QQYNSYPLT) (all IMGT numbering).

In a further aspect, provided herein is an ADC comprising or prepared from an antibody that binds human Nectin-4, wherein the antibody comprises a heavy chain variable region (VH) and a light chain variable region (VL), wherein the HCVR comprises SEQ ID NO: 7 and the LCVR comprises SEQ ID NO: 8.

In another aspect, provided herein is an ADC comprising or prepared from an antibody that binds human Nectin-4, wherein the antibody comprises one or more mutations in the antibody constant region, which alter Fc effector functions as disclosed herein, such as mutations in the constant region that result in reduced binding of the antibody to Fc receptors. In some embodiments, the antibody comprises an IgG1 heavy chain (HC) comprising one or more mutations selected from L234F, L235E, and P331S (EU numbering) or one or more mutations selected from L247F, L248E, and P350S (Kabat numbering). In some embodiments, the antibody comprises an IgG1 heavy chain (HC) comprising each of the mutations L234F, L235E, and P331S (EU numbering) or each of the mutations L247F, L248E, and P350S (Kabat numbering). In some embodiments, the antibody comprises a chain (HC) comprising one or more mutations selected from L234F, L235E, and P331S relative to a wild-type sequence as provided in SEQ ID NO:2. In some embodiments, the antibody comprises a heavy chain comprising each of the mutations L234F, L235E, and P331S relative to a wild-type sequence as provided in SEQ ID NO:2. In some embodiments, the antibody comprises a heavy chain comprising the amino acid sequence of SEQ ID NO:3.

In another aspect, provided herein is an ADC comprising or prepared from an antibody that binds human Nectin-4, wherein the antibody comprises a heavy chain (HC) and a light chain (LC), wherein the HC comprises SEQ ID NO: 5 and the LC comprises SEQ ID NO: 6.

In another aspect, provided herein is an ADC comprising a Nectin-4 antibody conjugated directly or through a linker to a payload, which payload may include a cytotoxic agent such as exatecan or analogs thereof. In some embodiments, the Nectin-4 antibody is conjugated to the payload via a thiol group of one or more cysteine residues.

In some embodiments, the ADC comprises or is prepared from an anti-Nectin-4 antibody that is conjugated via the thiol group of one or more cysteine residues present in the HC of the antibody, which optionally are present in the constant region of the HC. In some embodiments, the cysteine residues are present in the HC at one or more positions selected from C220, C226, C229 (EU Index numbering) and combinations thereof, or at positions selected from C233, C239, C242 and combinations thereof (Kabat numbering). In some embodiments, the anti-Nectin-4 antibody is conjugated via the thiol group of each of the cysteine residues present in the HC at positions C220, C226, C229 (EU Index numbering), or at positions C233, C239, C242 (Kabat numbering). In some embodiments, the anti-Nectin-4 antibody is conjugated via the thiol group of one or more cysteine residues present in the HC of the antibody, wherein the HC has the amino acid sequence of SEQ ID NO:5 and the cysteine residues are present in the HC at positions selected from C222, C228, C231 and combinations thereof, optionally wherein the anti-Nectin-4 antibody is conjugated via the thiol group of each of the cysteine residues present at positions C222, C228, and C231. In some embodiments, the anti-Nectin-4 antibody is conjugated via the thiol group of a cysteine residue present in the LC. In some embodiments, the anti-Nectin-4 antibody is conjugated via the thiol group of a cysteine residue present at the C-terminus of the LC, optionally wherein the LC is a kappa light chain and the cysteine residue is present at position C214. In some embodiments, the anti-Nectin-4 antibody is conjugated via the thiol group of one or more cysteine residues present in the LC of the antibody wherein the LC has the amino acid sequence of SEQ ID NO:6 and the cysteine residue is present in the LC at position C214. In some embodiments, the anti-Nectin-4 antibody is conjugated via the thiol group of cysteine residues present in the HC at positions C220, C226, C229 (EU Index numbering), or at positions C233, C239, C242 (Kabat numbering) and via the thiol group of a cysteine residue present in the LC at position C214. In some embodiments, the anti-Nectin-4 antibody is conjugated via the thiol group of cysteine residues present in the HC wherein the HC has the amino acid sequence of SEQ ID NO:5 and the cysteines are present at positions C222, C228, and C231, and the Nectin-4 antibody is conjugated via the thiol group of a cysteine residue present in the LC wherein the LC has the amino acid sequence of SEQ ID NO: 6 and the cysteine is present at position C214.

In a further aspect, provided herein is an ADC comprising or prepared from: (i) an antibody that binds human Nectin-4, (ii) optionally a linker, and (iii) a payload. In a further aspect, provided herein is an ADC comprising an antibody that binds human Nectin-4 which antibody is conjugated directly or via a linker to a payload. In a further aspect, provided herein is an ADC prepared by conjugating an antibody that binds human Nectin-4 to a payload, either directly or indirectly via a linker.

In a further aspect, provided herein is an ADC comprising or prepared from: (i) an antibody that binds human Nectin-4, (ii) optionally a linker, and (iii) exatecan or an analog thereof. In a further aspect, provided herein is an ADC comprising an antibody that binds human Nectin-4 which antibody is conjugated directly or via a linker to exatecan or an analog thereof. In a further aspect, provided herein is an ADC prepared by conjugating an antibody that binds human Nectin-4 and exatecan or an analog thereof, either directly or indirectly via a linker.

In a further aspect, provided herein is an ADC comprising an antibody that binds human Nectin-4, optionally a linker, and a compound of Formula (P), which in some aspects may be referred to as a "payload":

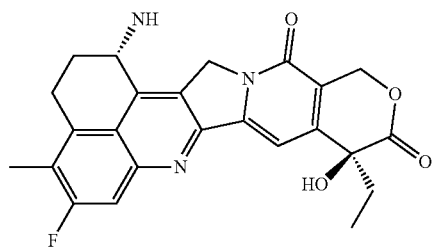

Formula (P)

The compound of Formula (P) may be referred to as exatecan.

In a further aspect, provided herein is an ADC comprising an antibody that binds human Nectin-4 conjugated directly or via a linker to a payload of Formula (P). In a further aspect, provided herein is an ADC prepared by conjugating an antibody that binds human Nectin-4 and a payload of Formula (P), either directly or indirectly via a linker.

In a further aspect, provided herein are compounds, which in some aspects may be utilized as a linker-payload for an ADC. In one aspect, disclosed is a compound of Formula (L-P), which may be utilized as a linker-payload for the ADCs disclosed herein:

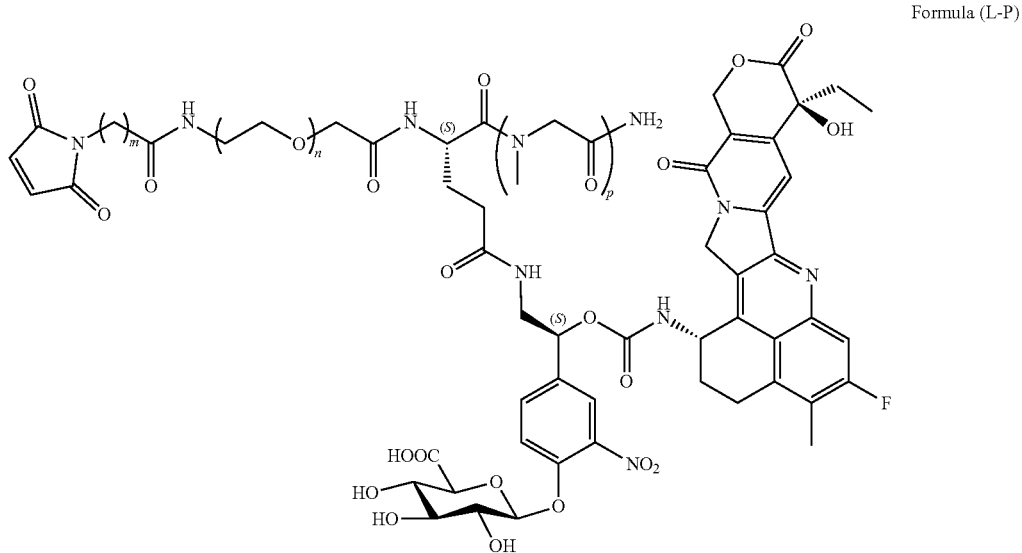

Formula (L-P)

wherein: m is selected from 1-6; n is selected from 1-6; and p is selected from 1-20.

In some embodiments of the linker-payload of Formula (L-P), m is 2.

In some embodiments of the linker-payload of Formula (L-P), n is 2.

In some embodiments of the linker-payload of Formula (L-P), p is 10.

In a further aspect, provided herein is an ADC comprising an antibody that binds human Nectin-4 and a compound of Formula (L-P) or an ADC prepared by conjugating an antibody that binds human Nectin-4 and a compound of Formula (L-P).

In another aspect, provided herein is a compound of Formula (L-P'), which may be used as a linker-payload for the ADCs disclosed herein:

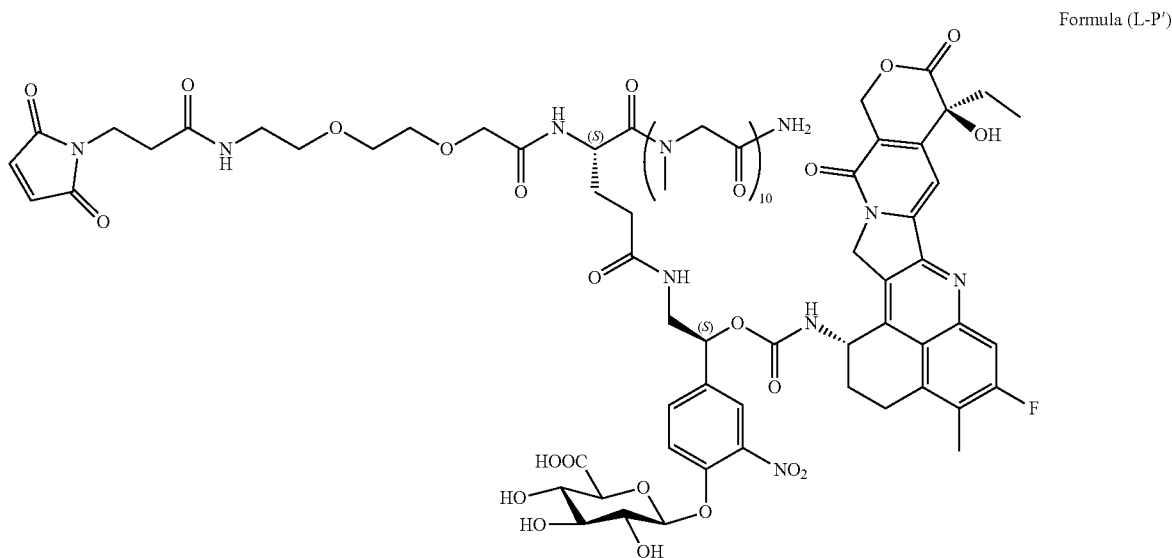

Formula (L-P')

In another aspect, provided herein is compound: (2S,3S,4S,5R,6S)-6-(4-((3S,9S)-40-amino-9-(2-(2-(2-(3-(2,5-dioxo-2,5-dihydro-1H-pyrrol-1-yl)propanamido)ethoxy)ethoxy)acetamido)-1-(((1S,9S)-9-ethyl-5-fluoro-9-hydroxy-4-m-ethyl-10,13-dioxo-2,3,9,10,13,15-hexahydro-1H,12H-benzo[de]pyrano(3',4':6,7]indolizino[1,2-b]quinolin-1-yl)amino)-1,14,17,20,23,26,29,32,35,38-decamethyl-1,6,10,13,16,19,22,25,28,31,34,37,40-tridecaoxo-2-oxa-5,11,14,17,20,23,26,29,32,35,38-undecaazatetracontan-3-yl)-2-nitrophenoxy)-3,4,5-trihydroxytetrahydro-2H-pyran-2-carboxylic acid; which compound is some aspects may be utilized as a linker-payload for the ADCs disclosed herein.

In a further aspect, provided herein is an ADC comprising an antibody that binds human Nectin-4 conjugated to a linker-payload of Formula (L-P). In a further aspect, provided herein is an ADC prepared by conjugating an antibody that binds human Nectin-4 and a linker-payload of Formula (L-P).

In one aspect, provided herein is an antibody-drug conjugate (ADC) of the Formula (ADC):

In some embodiments of the ADC of Formula (ADC), DAR is 8.

In some embodiments of the ADC of Formula (ADC), at least about 50%, 60%, 70%, 80%, 90%, 95%, 96%, 97%, 98%, or 99% of the ADC has a DAR of 8. In some embodiments of the ADC of Formula (ADC), the ADC is present in a composition wherein at least about 50%, 60%, 70%, 80%, 90%, 95%, 96%, 97%, 98%, or 99% of the ADC in the composition has a DAR of 8.

In some embodiments of the ADC of Formula (ADC), the Ab is conjugated to the linker-payload via the thiol group of one or more cysteine residues. In some embodiments, the Ab is conjugated via the thiol group of one or more cysteine residues in the HC of the Ab, optionally wherein the HC has the amino acid sequence of SEQ ID NO:5 and the cysteines are selected from positions C222, C228, C231, and combinations thereof. In some embodiments, the Ab is conjugated via the thiol group of one or more cysteine residues in the LC of the Ab, optionally wherein the LC has the amino acid sequence of SEQ ID NO:6 and the cysteine is present at

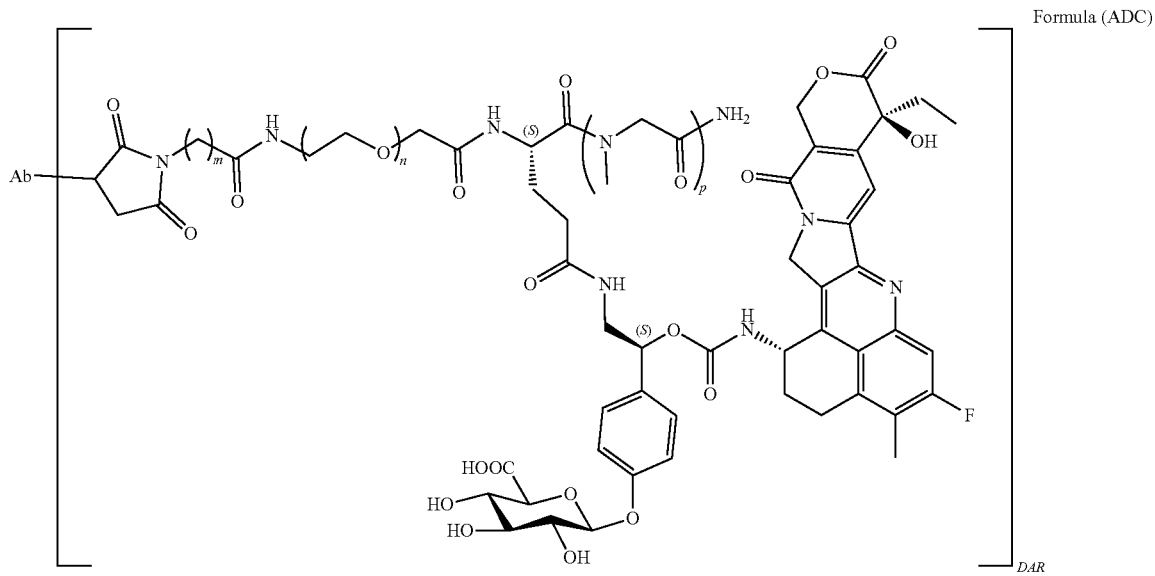

Formula (ADC)

wherein: Ab is an antibody that binds to Nectin-4 as disclosed herein; m is selected from 1-6; n is selected from 1-6; p is selected from 1-20; and DAR is a value of the range 1-8, inclusive, and represents the drug-antibody ratio (DAR) of the ADC.

In some embodiments of the ADC of Formula (ADC), m is 2.

In some embodiments of the ADC of Formula (ADC), n is 2.

In some embodiments of the ADC of Formula (ADC), p is 10.

position C214. In some embodiments, the Ab is conjugated via all of C222, C228, and C231 of the HC of SEQ ID NO:5, and C214 of the LC of SEQ ID NO:6.

In a further aspect, provided herein is an ADC comprising an antibody that binds human Nectin-4 conjugated to a linker-payload of Formula (L-P'). In a further aspect, provided herein is an ADC prepared by conjugating an antibody that binds human Nectin-4 and a linker-payload of Formula (L-P').

In one aspect, provided herein is an antibody-drug conjugate (ADC) of the Formula (ADC'):

Formula (ADC')

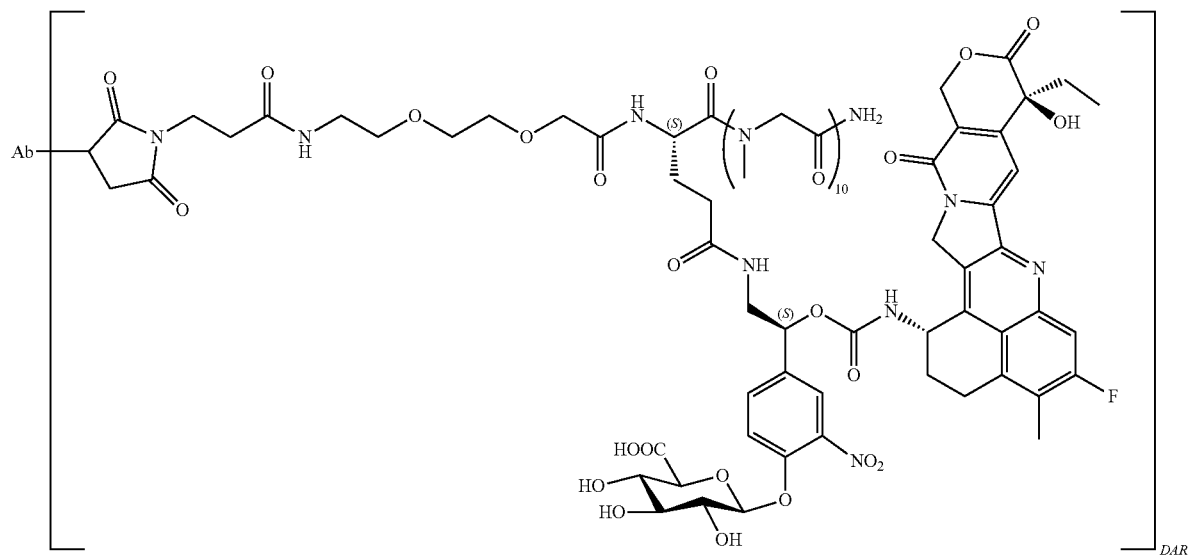

wherein DAR is a value of the range 1-8, inclusive, and represents the drug-antibody ratio (DAR) of the ADC.

In some embodiments of the ADC of Formula (ADC'), DAR is 8.

In some embodiments of the ADC of Formula (ADC'), at least about 50%, 60%, 70%, 80%, 90%, 95%, 96%, 97%, 98%, or 99% of the ADC has a DAR of 8. In some embodiments of the ADC of Formula (ADC'), the ADC is present in a composition wherein at least about 50%, 60%, 70%, 80%, 90%, 95%, 96%, 97%, 98%, or 99% of the ADC in the composition has a DAR of 8.

In some embodiments of the ADC of Formula (ADC'), the Ab is conjugated to the linker-payload via the thiol group of one or more cysteine residues. In some embodiments, the Ab is conjugated via the thiol group of one or more cysteine residues in the HC of the Ab, optionally wherein the HC has the amino acid sequence of SEQ ID NO:5 and the cysteines are selected from positions C222, C228, C231, and combinations thereof. In some embodiments, the Ab is conjugated via the thiol group of one or more cysteine residues in the LC of the Ab, optionally wherein the LC has the amino acid sequence of SEQ ID NO:6 and the cysteine is present at position C214. In some embodiments, the Ab is conjugated via all of C222, C228, and C231 of the HC of SEQ ID NO:5, and C214 of the LC of SEQ ID NO:6.

In another aspect, provided herein is an antibody-drug conjugate (ADC) of the Formula (ETx-22):

Formula (ETx-22)

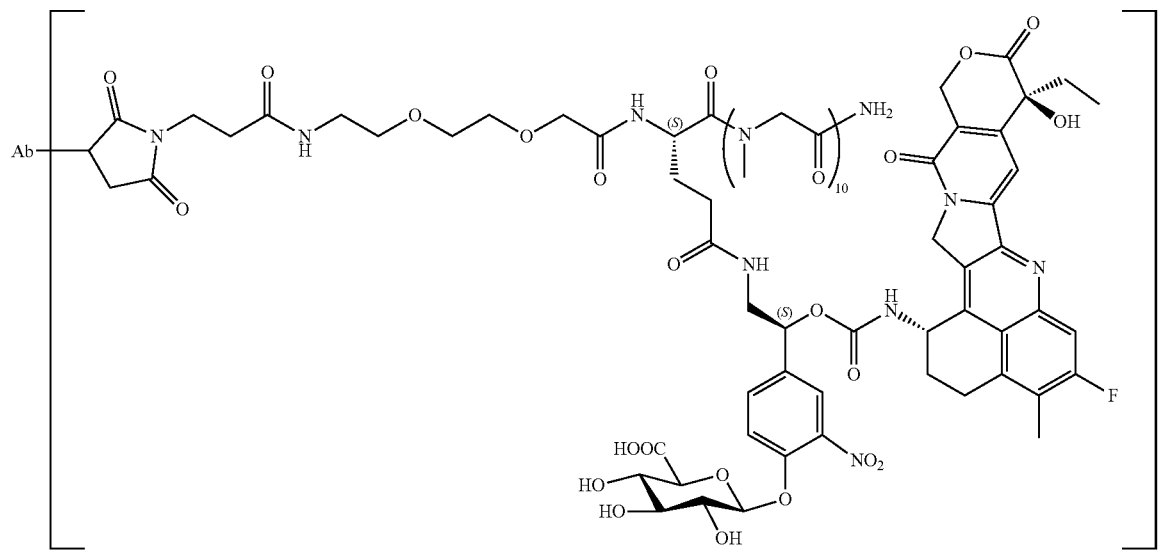

wherein Ab is an antibody that binds to Nectin-4 as disclosed herein. Ab comprises a heavy chain (HC) and a light chain (LC), wherein the HC comprises SEQ ID NO: 5 and the LC comprises SEQ ID NO: 6. Ab is conjugated to the linker-payload via the thiol group of cysteine residues including C222, C228, and C231 of the HC of SEQ ID NO:5, and C214 of the LC of SEQ ID NO:6.

In another aspect, provided herein is a composition comprising an anti-Nectin-4 ADC disclosed herein. In one aspect of the disclosed compositions comprising an anti-Nectin-4 ADC, at least about 50%, 60%, 70%, 80%, 90%, 95%, 96%, 97%, 98%, or 99% of the ADC in the composition has a DAR of 8.

In another aspect, provided herein is a pharmaceutical composition comprising an anti-Nectin-4 antibody disclosed herein, and one or more pharmaceutically acceptable carriers, diluents, or excipients. In another aspect, provided herein is a pharmaceutical composition comprising an anti-Nectin-4 ADC disclosed herein, and one or more pharmaceutically acceptable carriers, diluents, or excipients. In another aspect, provided herein is a pharmaceutical composition comprising an anti-Nectin-4 ADC disclosed herein, wherein at least about 50%, 60%, 70%, 80%, 90%, 95%, 96%, 97%, 98%, or 99% of the ADC in the composition has a DAR of 8.

In another aspect, provided herein is a method of treating cancer, comprising administering to a patient in need thereof, an effective amount of an anti-Nectin-4 ADC as disclosed herein, such as a Nectin-4 expressing cancer. In a further aspect, provided herein is a method of treating cancer, comprising administering to a patient in need thereof, an effective amount of an anti-Nectin-4 ADC disclosed herein, wherein the cancer is urothelial carcinoma, breast cancer, lung cancer, gastric cancer, esophageal cancer, colorectal cancer, pancreatic cancer, head and neck cancer, ovarian cancer, or prostate cancer. In another aspect, provided herein is a method of treating cancer, comprising administering to a patient in need thereof, an effective amount of an anti-Nectin-4 ADC as disclosed herein, optionally wherein the cancer is resistant to treatment with an ADC comprising a Nectin-4-binding agent and an auristatin, such as monomethyl auristatin E (MMAE). In another aspect, provided herein is a method of treating cancer, comprising administering to a patient in need thereof, an effective amount of an anti-Nectin-4 ADC as disclosed herein, wherein the patient previously has been administered enfortumab vedotin, optionally, enfortumab vedotin-ejfv marketed under the brand name Padcev®.

In another aspect, provided herein is an ADC comprising a Nectin-4 binding agent and exatecan for use in a method comprising administering the ADC to a patient suffering from cancer as disclosed herein, such as a Nectin-4 expressing cancer. Optionally the cancer is resistant to treatment with an ADC comprising a Nectin-4-binding agent and an auristatin, such as monomethyl auristatin E (MMAE). In another aspect, provided herein is an ADC comprising a Nectin-4 binding agent and exatecan for use in a method comprising administering the ADC to a patient suffering from a Nectin-4 expressing cancer, wherein the patient previously has been administered enfortumab vedotin, optionally, enfortumab vedotin-ejfv marketed under the brand name Padcev @.

In another aspect, provided herein is a pharmaceutical composition comprising a Nectin-4 binding agent and exatecan for use in treating cancer, such as a Nectin-4 expressing cancer. Optionally, the cancer is resistant to treatment with an ADC comprising a Nectin-4-binding agent and an aurista-tin, such as monomethyl auristatin E (MMAE). In another aspect, provided herein is a pharmaceutical composition comprising a Nectin-4 binding agent and exatecan for use in treating cancer, wherein the patient previously has been administered enfortumab vedotin, optionally, enfortumab vedotin-ejfv marketed under the brand name Padcev®.

In another aspect, provided herein is the use of an ADC comprising a Nectin-4 binding agent and exatecan for the manufacture of a medicament for the treatment of a patient suffering from a Nectin-4 expressing cancer. Optionally, the cancer is resistant to treatment with an ADC comprising a Nectin-4-binding agent and an auristatin, such as monomethyl auristatin E (MMAE). In another aspect, provided herein is the use of an ADC comprising a Nectin-4 binding agent and exatecan for the manufacture of a medicament for the treatment of a patient suffering from a Nectin-4 expressing cancer, wherein the patient previously has been administered enfortumab vedotin, optionally, enfortumab vedotin-ejfv marketed under the brand name Padcev®.

DETAILED DESCRIPTION

Nectin-4

Figure 1:
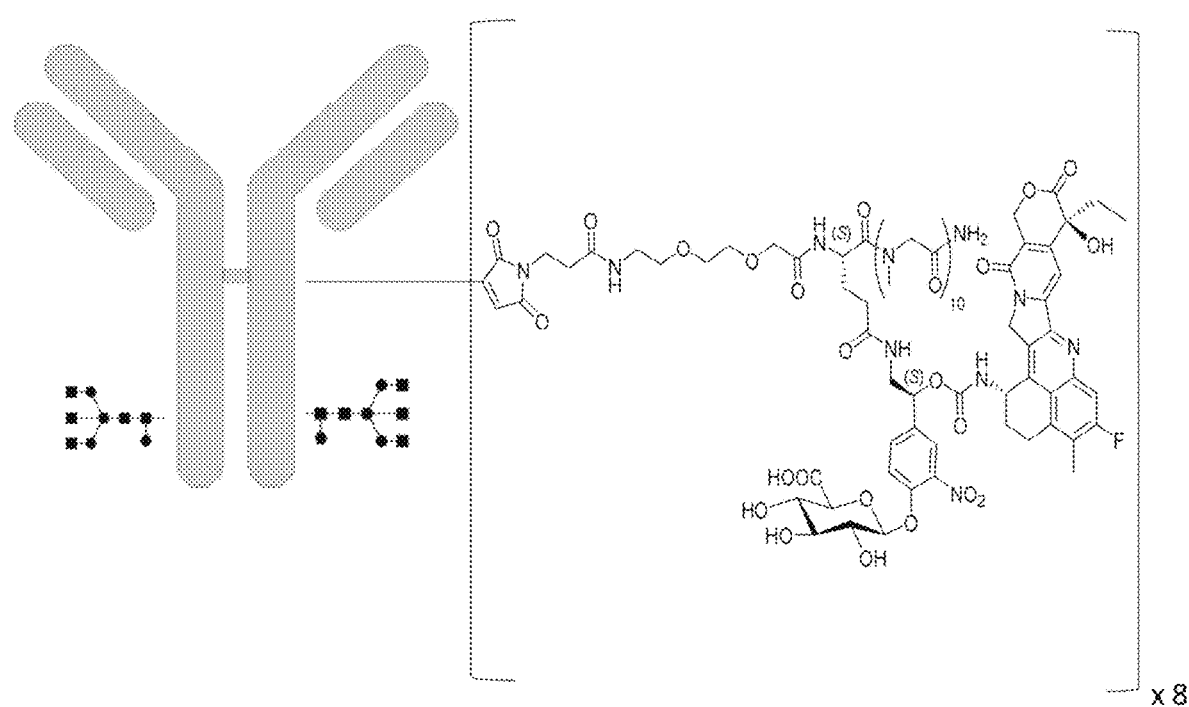
FIG. 1. Schematic representation of ETx-22.

As used herein, "human Nectin-4" refers to a human Nectin-4 protein or polypeptide, also known as poliovirus receptor-related 4, Ig superfamily receptor LNIR, or poliovirus receptor-related protein 4 (PVRL4). An amino acid sequence of human Nectin-4 can be found at NP_112178.2 and as provided in SEQ ID NO: 1.

Antibodies

The disclosed ADCs comprise an antibody. The term "antibody," as used herein, refers to an immunoglobulin molecule that binds an antigen. The antibodies can be of any class (e.g., IgG, IgE, IgM, IgD, IgA), and any subclass (e.g., IgG1, IgG2, IgG3, IgG4).

An exemplary antibody of the present disclosure is an immunoglobulin G (IgG) type antibody comprised of four polypeptide chains: two heavy chains (HC) and two light chains (LC) that are cross-linked via inter-chain disulfide bonds. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector function. Each heavy chain is comprised of a heavy chain variable region (VH) and a heavy chain constant region. Each light chain is comprised of a light chain variable region (VL) and a light chain constant region. The IgG isotype may be further divided into subclasses (e.g., IgG1, IgG2, IgG3, and IgG4).

The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTics database available on at www.imgt.org; see Lefranc et al., Nucleic Acids Res. 1999; 27:209-212). The CDRs of the present disclosure are determined by North.

Certain antibodies of the ADCs described herein contain an IgG1 Fc region or an Fc region derived from human IgG1, e.g., a modified IgG1 Fc region having altered Fc effector functions. IgG1 is known to induce antibody-dependent cell cytotoxicity (ADCC) and complement-dependent cytotoxicity (CDC). Some antibodies of the disclosed ADCs comprise amino acid substitutions introduced into the IgG1 Fc region that alter Fc effector function. In some aspects of the antibodies of the disclosed ADCs, mutations are introduced in the Fc region at positions 234 and 235 (EU Index numbering) or at positions 247 and 248 (Kabat numbering). In some aspects of the antibodies disclosed herein, mutations are introduced in the Fc region at one or more positions selected from 234, 235, and 331 (EU Index numbering) or from 247, 248, and 350 (Kabat numbering). In some aspects, the anti-Nectin-4 antibodies of the present disclosure comprise a modified human IgG1 Fc region comprising one or more mutations selected from L234E, L235E, P331S, and combinations thereof (EU Index numbering) or selected from L247F, L248E, P350S, and combinations thereof (Kabat numbering). In further aspects, these amino acid substitutions introduced into IgG1 Fc region reduced or eliminated measurable antibody effector function, including but not limited to reduced binding to the Fc receptor.

Mammalian expression of antibodies from IgG subclasses can result in clipping of C-terminal amino acids from one or both heavy chains; for example, one or two C-terminal amino acids can be removed for IgG1 antibodies. For IgG1 antibodies, if a C-terminal lysine is present, then it may be truncated or clipped off from the heavy chain during expression. Additionally, a penultimate glycine may also be truncated or clipped off from the heavy chain as well. The anti-Nectin-4 antibodies disclosed herein may include one or more truncations and clippings accordingly.

Mammalian expression of antibodies can also result in the modification of N-terminal amino acids. For example, where the N-terminal most amino acid of a heavy chain or light chain is a glutamine or glutamic acid, it may be modified into pyro-glutamic acid. For example, where the C-terminal most amino acid of a heavy chain or light chain is a lysine or glycine, it may be removed. The anti-Nectin-4 antibodies disclosed herein may include one or more modifications or removals accordingly.

The terms "nucleic acid" or "polynucleotide", as used interchangeably herein, refer to polymers of nucleotides, including single-stranded and/or double-stranded nucleotide-containing molecules, such as DNA, cDNA and RNA molecules, incorporating native, modified, and/or analogs of, nucleotides. Polynucleotides of the present disclosure may also include substrates incorporated therein, for example, by DNA or RNA polymerase or a synthetic reaction.

Polynucleotides of the present disclosure may be expressed in a host cell, for example after the polynucleotides have been operably linked to an expression control sequence. Expression control sequences capable of expression of polynucleotides to which they are operably linked are well known in the art. For example, an expression vector may include a sequence that encodes one or more signal peptides that facilitate secretion of the polypeptide(s) from a host cell. The signal peptide may be an immunoglobulin signal peptide or a heterologous signal peptide, for example. Expression vectors containing a polynucleotide of interest (e.g., a polynucleotide encoding a polypeptide of an antibody) may be transferred into a host cell by well-known methods. Additionally, expression vectors may contain one or more selection markers, e.g., tetracycline, neomycin, and dihydrofolate reductase, to aid in detection of host cells transformed with the desired polynucleotide sequences.

A host cell includes cells stably or transiently transfected, transformed, transduced or infected with one or more expression vectors expressing all or a portion of an antibody of the present disclosure. According to some embodiments, a host cell may be stably or transiently transfected, transformed, transduced, or infected with an expression vector expressing HC polypeptides and an expression vector expressing LC polypeptides of an antibody of the present disclosure. In some embodiments, a host cell may be stably or transiently transfected, transformed, transduced, or infected with an expression vector expressing HC and LC polypeptides of an antibody of the present disclosure. The antibody of the present disclosure may be produced in mammalian cells such as CHO, NS0, HEK293 or COS cells according to techniques well known in the art.

Medium, into which an antibody of the present disclosure has been secreted, may be purified by conventional techniques, such as mixed-mode methods of ion-exchange and hydrophobic interaction chromatography. For example, the medium may be applied to and eluted from a Protein A or G column using conventional methods; mixed-mode methods of ion-exchange and hydrophobic interaction chromatography may also be used. Soluble aggregate and multimers may be effectively removed by common techniques, including size exclusion, hydrophobic interaction, ion exchange, or hydroxyapatite chromatography. The product may be immediately frozen, for example at −70 degrees C., refrigerated, or may be lyophilized. Various methods of protein purification may be employed, and such methods are known in the art and described, for example, in Deutscher, Methods in Enzymology 182: 83-89 (1990) and Scopes, Protein Purification: Principles and Practice, 3rd Edition, Springer, NY (1994).

Anti-Nectin-4 Antibodies

Antibodies for use in the disclosed ADCs exhibit specific binding to Nectin-4 with respect to other proteins of the human Nectin-family, such as Nectin-1. As used herein, the terms "binding" and "specific binding" refer to the binding of an antibody to an epitope of the Nectin-4 antigen. The measure of the binding strength of an antibody is referred to as affinity. Methods for determining such a binding and/or affinity using in vitro assays are known to the person skilled in the art. According to the present invention, detection with flow cytometry, immuno-histochemistry and/or fluorescence are described and particularly preferred herein. The affinity of the binding of an antibody to an antigen may be defined by the terms $K_a$ (rate constant for the association of the antibody from the antibody/antigen complex), $K_D$ (dissociation constant), and $K_{dis}$ ($K_D/K_a$).

In some aspects, the disclosed ADCs may comprise or may be prepared from an anti-Nectin-4 antibody which is a tumor-selective anti-Nectin-4 antibody. A tumor-selective anti-Nectin-4 antibody may be characterized as an anti-Nectin-4 antibody that binds Nectin-4 expressed by tumors with a higher affinity in comparison to Nectin-4 expressed by normal cells. For comparison, in some aspects binding affinity may be detected by flow cytometry, immuno-histochemistry and/or fluorescence. Normal cells may include normal human endothelial keratinocytes (NHEKs). Normal cells may include in vitro differentiated Nectin-4 expressing human endothelial keratinocytes. In one aspect, tumor-selective anti-Nectin-4 antibodies may have a dissociation constant $K_D$ for binding to Nectin-4 expressed on keratinocytes which is greater than the dissociation constant for binding to Nectin-4 expressed on tumor cells. In one aspect, tumor-selective anti-Nectin-4 antibodies exhibit lower internalization and/or cytotoxic activity towards keratinocytes in comparison to tumor cells. In one aspect, tumor-selective anti-Nectin-4 antibodies exhibit lower binding affinity, lower internalization, and lower cytotoxic activity towards keratinocytes in comparison to tumor cells. In one aspect, the anti-Nectin-4 antibodies of the disclosed ADCs exhibit lower binding affinity, internalization, or cytotoxic activity towards keratinocytes in comparison to tumor cells in comparison to the reference antibody HA22 mAb (enfortumab).

Tumor-selective anti-Nectin-4 antibodies for use in the disclosed ADCs may comprise antibodies disclosed in WO2022/207822 and WO2022/207825. In one aspect, the ADCs disclosed herein comprise a monoclonal antibody referred to as 15A7.5 or a humanized variant thereof referred to as H1L2_15A7.5 comprising back mutations as disclosed in WO2022/207822 and WO2022/207825 and having a HC comprising the amino acid sequence of SEQ ID NO:5 and having a LC comprising the amino acid sequence of SEQ ID NO:6.

In an aspect, provided herein is an ADC comprising or prepared from an antibody that binds human Nectin-4, wherein the antibody comprises a heavy chain variable region (HCVR) and a light chain variable region (LCVR), wherein the HCVR comprises heavy chain complementarity determining regions (HCDR) HCDR1, HCDR2, and HCDR3, and the LCVR comprises light chain complementarity determining regions (LCDR) LCDR1, LCDR2, and LCDR3, wherein the HCDR1 comprises SEQ ID NO: 9 (NYGMA), the HCDR2 comprises SEQ ID NO: 10 (FISNLAYGINYADTVTG), the HCDR3 comprises SEQ ID NO: 11 (GARATGWFAY), the LCDR1 comprises SEQ ID NO: 12 (KASQNVDTHVA), the LCDR2 comprises SEQ ID NO: 13 (SASYRYS), and the LCDR3 comprises SEQ ID NO: 14 (QQYNSYPLT) (all Kabat numbering). In another aspect, provided herein is an antibody that binds human Nectin-4, wherein the HCDR1 comprises SEQ ID NO: 15 (GFTFSNYG), the HCDR2 comprises SEQ ID NO: 16 (ISNLAYGI), the HCDR3 comprises SEQ ID NO: 17 (ARGARATGWFAY), the LCDR1 comprises SEQ ID NO: 18 (QNVDTH), the LCDR2 comprises SEQ ID NO: 19 (SAS), and the LCDR3 comprises SEQ ID NO: 20 (QQYNSYPLT) (all IMGT numbering).

In an aspect, the ADC disclosed herein comprises or is prepared from an anti-Nectin-4 antibody, wherein the antibody comprises a heavy chain variable region (HCVR) and a light chain variable region (LCVR), wherein the antibody comprises a HCVR comprising SEQ ID NO: 7 and a LCVR comprising SEQ ID NO: 8.

In a further aspect, the ADC disclosed herein comprises or is prepared from an anti-Nectin-4 antibody, wherein the antibody comprises a heavy chain variable region (HCVR) and a light chain variable region (LCVR), and wherein the antibody has a human IgG1 or IgG4 isotype. In a further aspect, wherein the anti-Nectin-4 antibody has a human IgG1 isotype. In a further aspect, the anti-Nectin-4 antibody has a human IgG1 isotype and the HC of the anti-Nectin-4 antibody comprises one or more mutations at positions L234, L235, and P331 (EU Index numbering) or at positions L247, L248, P350 (Kabat numbering). In a further aspect, the anti-Nectin-4 antibody comprises one or more mutations selected from L234F, L235E, and P331S (EU Index numbering) or L247F, L248E, P350S (Kabat numbering).

In an aspect, provided herein is an ADC comprising or prepared from an antibody that binds human Nectin-4, wherein the antibody comprises a heavy chain (HC) and a light chain (LC), wherein the HC comprises SEQ ID NO: 5 and the LC comprises SEQ ID NO: 6.

In a further aspect, provided herein is an ADC comprising or prepared from an antibody that binds human Nectin-4, wherein the HC consists of SEQ ID NO: 5 and the LC consists of SEQ ID NO: 6.

In another aspect, provided herein are mammalian cells comprising a DNA molecule comprising a polynucleotide sequence encoding polypeptides comprising the amino acid sequence of SEQ ID NO: 5, the amino acid sequence of SEQ ID NO: 6, or both of the amino acid sequence of SEQ ID NO: 5 and the amino acid sequence of SEQ ID NO: 6. In some aspects, the cells are capable of expressing Nectin-4 antibodies as disclosed herein.

In another aspect, provided herein are mammalian cells comprising a first DNA molecule and a second DNA molecule, wherein the first DNA molecule comprises a polynucleotide sequence encoding a polypeptide comprising the amino acid sequence of SEQ ID NO:5, and wherein the second DNA molecule comprises a polynucleotide sequence encoding a polypeptide comprising the amino acid sequence of SEQ ID NO:6.

In another aspect, provided herein is a process for producing a Nectin-4 antibody comprising cultivating one of the mammalian cells disclosed herein under conditions such that the antibody is expressed, and recovering the expressed antibody.

In another aspect, provided herein is an antibody produced by cultivating a mammalian cell comprising a DNA molecule comprising a polynucleotide sequence encoding polypeptides comprising the amino acid sequences of SEQ ID NO: 5, SEQ ID NO: 6, or both of SEQ ID NO:5 and SEQ ID NO:6, under conditions such that the antibody is expressed, and recovering the expressed antibody.

Figure 3:
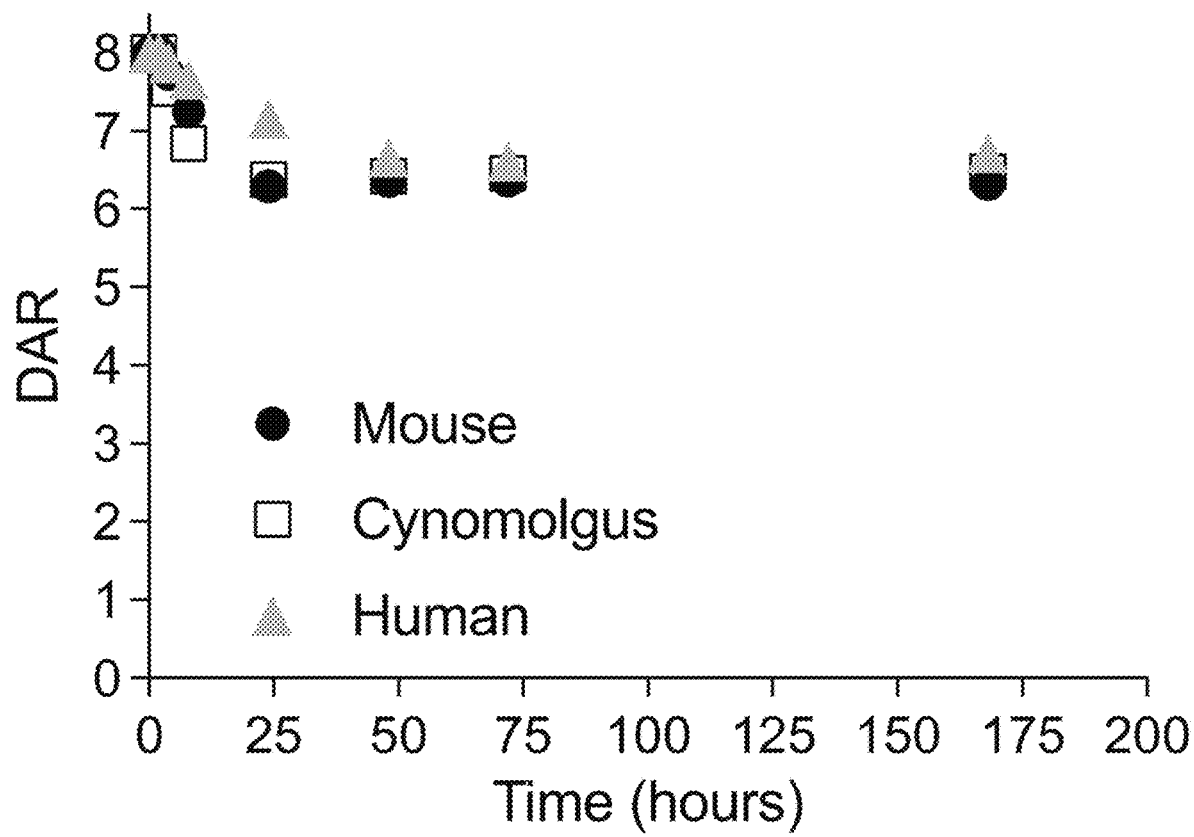
FIG. 3. Ex vivo stability assessment. ETx-22 was incubated in mouse, cynomolgus or human serum. At the indicated times, ETx-22 was affinity-captured via anti-human LC-kappa (mouse) or Fc-nectin-4 fragment (cynomolgus and human) and drug antibody ratio was measured by LC/MS.

In another aspect, provided herein is an antibody produced by cultivating a mammalian cell comprising a first DNA molecule and a second DNA molecule, wherein the first DNA molecule comprises a polynucleotide sequence encoding a polypeptide comprising the amino acid sequence of SEQ ID NO:5, and wherein the second DNA molecule comprises a polynucleotide sequence encoding a polypeptide comprising the amino acid sequence of SEQ ID NO:6, under conditions such that the antibody is expressed, and recovering the expressed antibody:

The term "enfortumab" as used herein refers to a fully human anti-Nectin-4 IgG1 kappa monoclonal antibody with the sequence as disclosed in WO2012047724 (FIGS. 3A and 3B), expressed and purified using standard conditions. Enfortumab may be referred to herein alternatively as the HA22 mAb. The term enfortumab-vedotin-ejfv refers to the antibody-drug conjugate sold under the brand name PADCEV®, which comprises enfortumab conjugated to a monomethyl auristatin E (MMAE) payload via a peptide linker, where the linker-payload has a formula represented as maleimidocaproyl (MC)-valine-citrulline-PABC-MMAE.

Payloads

Nectin-4 antibodies of the present disclosure can be conjugated to various payloads (including pharmaceutically acceptable salts thereof) to form an antibody drug conjugate (ADC). In one aspect, the disclosed ADCs comprise or are prepared from: (i) an antibody that binds human Nectin-4, (ii) optionally a linker, and (iii) a payload. In a further aspect, the disclosed ADCs comprise an antibody that binds human Nectin-4 conjugated directly or via a linker to a payload. In a further aspect, the disclosed ADCs are prepared by conjugating an antibody that binds human Nectin-4 to a payload, either directly or indirectly via a linker. In a further aspect, the disclosed ADCs release a payload after the ADCs bind target cells that expresses Nectin-4 and the ADCs are internalized by the target cells.

Suitable moieties for conjugation to the Nectin-4 antibodies disclosed herein include cytotoxic agents (e.g., chemotherapeutic agents), prodrug converting enzymes, radioactive isotopes or compounds, toxins, and other known payloads in the art.

Exemplary ADCs herein utilize exatecan-based payloads (e.g., exatecan or exatecan analogs). Exatecan is a topoisomerase I (TOPO 1) inhibitor that has been shown to have anticancer activity. Exatecan and its analogs bind to the TOPO 1/DNA complex which prevents reannealing leading to cell death from the accumulation of partially cleaved DNA.

In a further aspect, the disclosed ADCs comprise an antibody that binds human Nectin-4, optionally a linker, and exatecan or an analog thereof. In a further aspect, the disclosed ADCs comprise an antibody that binds human Nectin-4 conjugated directly or via a linker to exatecan or an analog thereof. In a further aspect, the disclosed ADCs are prepared by conjugating an antibody that binds human Nectin-4 and exatecan or an analog thereof, either directly or indirectly via a linker. In the disclosed ADCs, exatecan may be conjugated to the anti-Nectin-4 antibody either directly or indirectly via a linker through its free $NH_2$ group (e.g., by the $NH_2$ group of exatecan forming an amide bond with the linker).

In a further aspect, the disclosed ADCs comprise or are prepared from: (i) an antibody that binds human Nectin-4, (ii) optionally a linker, and a compound of Formula (P), which may be referred to as a "payload":

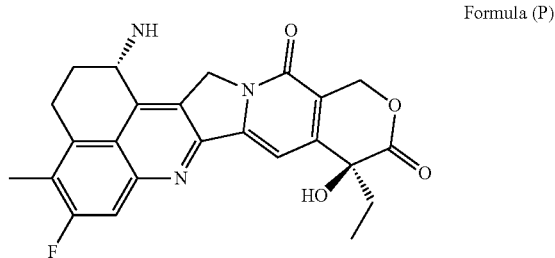 [SMILES: CC[C@@]1(O)C(=O)OCc2c1cc1n(c2=O)Cc2c-1nc1cc(F)c(C)c3c1c2[C@@H](N)CC3]

Formula (P)

A compound of Formula (P) may be referred to as exatecan.

In a further aspect, the disclosed ADCs comprise an antibody that binds human Nectin-4 conjugated directly or via a linker to a payload of Formula (P). In a further aspect, the disclosed ADCs are prepared by conjugating an antibody that binds human Nectin-4 and a payload of Formula (P), either directly or indirectly via a linker.

Linkers

As disclosed herein, payloads can be conjugated with a Nectin-4 antibody to form a Nectin-4 ADC described herein by methods understood by one of skill in the art. One example of such conjugation would include connection of a payload described herein to a Nectin-4 antibody described herein via a linker.

Linkers used for ADCs are designed for stability in plasma to allow time for the ADC to localize to the target cells. Releasing the payload too soon lowers the therapeutic index of the ADC by damaging non-targeted tissue of all kinds. When the ADC is internalized into the target cell, then the linker should provide a mechanism for liberation of the payload, such so the payload can work as designed.

Linkers known to those of skill in the art contain, for example, cleavable moieties and noncleavable moieties. Accordingly, provided herein are ADCs where the payload, e.g. exatecan or an exatecan analog is conjugated to an anti-Nectin-4 antibody via a linker with a cleavable moiety or is conjugated to an antibody via a linker with a non-cleavable moiety.

Any suitable linkers known in the art can be used in preparing the ADCs of the present disclosure. In certain aspects, the linkers comprise reactive groups capable of conjugating with both the antibodies of the present disclosure and the payload. Examples include but are not limited to linkers comprising a maleimide group which is conjugatable to a thiol of a cysteine residue of the antibody and a succinimide ester group which his conjugatable to the payload, such as 3-(maleimido)propionic acid N-hydroxysuccinimide ester.

In certain aspects of the present disclosure, the ADC comprises a linker having a moiety that is cleavable. Cleavable moieties may include beta-glucuronide which is cleavable by intracellular beta-glucuronidase.

In some aspects of the present disclosure, the ADC comprises a linker which comprises a spacer unit, herein called spacer unit A, that connects the cysteine(s) of the antibodies disclosed herein to the payloads described herein. Some of the chemistries used in the art to conjugate payloads to thiol groups of cysteines include maleimide or succinimide chemistries, and can be utilized for ADCs of the present disclosure. In further aspects of the present disclosure, maleimide-type spacers such as maleimidopropionyl are utilized in the linkers disclosed herein.

In some aspects of the present disclosure, provided herein is an ADC with a spacer unit A of formula:

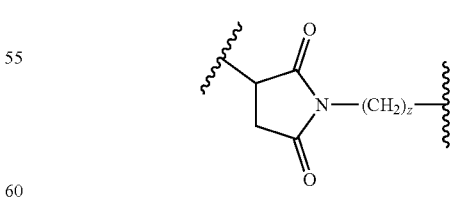

wherein z is from 1-5. The spacer unit A is conjugated to the anti-Nectin-4 antibody via the reduced maleimidyl group. The spacer unit A may be conjugated to the payload either directly or indirectly via a linker through the methylene moiety (i.e., via the (CH2)z) moiety. In some aspects of spacer unit A, z is 2. In some aspects, the spacer unit A "spaces" or "positions" the remainder of the linker and the payload distally from the antibody of the ADC.

Linkers Comprising Polysarcosine (PSAR) and Polyethylene Glycol (PEG).

In some aspects, the disclosed ADCs comprise a linker comprising a polysarcosine moiety. ADCs comprising polysarcosine moieties are known in the art. (See WO2019/081455 and WO2022/207699; and Conilh et at. "Exatecan antibody drug conjugates based on a hydrophilic polysarcosine drug-linker platform" (Pharmaceuticals 14 (2021), 247).

In some aspects, the disclosed linkers comprise at least one ethylene glycol unit, e.g., 1, 2, 3, 4, 5, 6, 7, 8, 9, or 10 or more ethylene glycol units. Further preferred linkers include highly polar spacers such as an acyl group, carbamoyl group and/or sulfamide group added to at least at least one ethylene glycol unit, e.g., 1, 2, 3, 4, 5, 6, 7, 8, 9, or 10 or more ethylene glycol units.

In certain embodiments, the linker is a hydrophilic polysarcosine linker comprising, e.g., up to 20 sarcosine units, and at least one ethylene glycol unit, e.g., 1, 2, 3, 4, 5, 6, 7, 8, 9, or 10 or more ethylene glycol units, wherein the linker is subject to cleavage by a glycosidase, and particularly subject to cleavage by a glucuronidase.

In certain embodiments, the linker is a hydrophilic polysarcosine linker comprising, e.g., about 8-12 sarcosine units, and at least one ethylene glycol unit, e.g., up to 10 ethylene glycol units, and wherein the linker is subject to cleavage by a glycosidase, and particularly subject to cleavage by a glucuronidase.

In certain embodiments, the linker is a hydrophilic polysarcosine linker comprising 10 sarcosine units, and 2 ethylene glycol units, and wherein the linker is subject to cleavage by a glucuronidase.

A further aspect of the invention relates to a linker-drug conjugate comprising: (i) a hydrophilic polysarcosine linker comprising, e.g., about 8-12 sarcosine units, and at least one ethylene glycol unit, e.g., 1, 2, 3, 4, 5, 6, 7, 8, 9, or 10 or more ethylene glycol units, wherein the linker is subject to cleavage by a glycosidase, and particularly subject to cleavage by a glucuronidase, and wherein the linker comprises a thiol-reactive group, e.g., a maleimide group capable of reacting with cysteine residues on an antibody or antigen-binding fragment thereof, and (ii) exatecan covalently attached to the linker.

In particular embodiments, the linker-drug conjugate comprises: (i) a hydrophilic polysarcosine group (e.g., a polysarcosine group consisting of 10 sarcosine units), and a polyethylene group (e.g., a polyethylene glycol group consisting of 2 ethylene glycol units), wherein the linker is subject to cleavage by a glycosidase, and particularly subject to cleavage by a glucuronidase, and wherein the linker comprises a maleimide group capable of reacting with cysteine residues on an antibody or antigen-binding fragment thereof, and (ii) exatecan covalently attached to the linker. In some embodiments, the polysarcosine group is located at a position in the linker characterized as "orthogonal" relative to the polyethylene glycol group and exatecan.

Self-Immolative Units

Self-immolation, or self-removal, of a part of the ADC can be designed into the structure of the ADC, for example within the linker of the ADC. Self-immolation typically involves a self-immolative unit becoming activated after removal of a triggering group that is conjugated to the self-immolative unit. In some aspects of self-immolative units, the triggering group is cleaved enzymatically from the self-immolative unit via a cellular enzyme after the ADC is internalized by a target cell. Suitable triggering groups may include beta-glucuronide that are cleaved from the self-immolative unit via intracellular, beta-glucuronidase. Then further biological or chemical reactions result in the spontaneous elimination of the self-immolative unit itself from the linker. The self-immolative unit can provide positive attributes to the ADC, such as providing space to reduce steric hindrance of cellular proteases reaching the peptide cleavage site in the ADC.

In some aspects of the present disclosure, the ADC described herein contains a self-immolative unit. When present, the self-immolative unit may be located within the linker and may become activated after enzymatic cleavage of a triggering group from the self-immolative unit. In some aspects, the self-immolative unit comprises a 3-nitro-octopamine group conjugated via its 4-hydroxyl group to a beta-glucuronide, which beta-glucuronide is cleavable via intracellular beta-glucuronidase expressed by a tumor.

Conjugation

In the disclosed ADCs, the payload, particularly exatecan or an exatecan analog, is covalently conjugated to the anti-Nectin-4 antibody either directly or indirectly via a linker. Methods to conjugate antibodies disclosed herein to the payloads disclosed herein are known in the art. In some methods, the antibody is conjugated to a linker in a first reaction, and then the antibody and linker are conjugated to the payload in a second reaction. In some methods, the antibody is conjugated to the payload or payload/linker in one reaction.

The payload may be conjugated to any suitable position of the anti-Nectin-4 antibody which does not abolish the binding of the antibody to Nectin-4. For example, the payload may be conjugated to a reactive amino acid residue on the antibody, e.g., a cysteine residue having a thiol group.

In certain aspects, the ADC has a molar drug-antibody/antibody fragment ratio (DAR) of greater than 1, i.e., more than one drug molecule is attached to an antibody/antibody fragment. Typically, the conjugate has a DAR of about 2:1 to about 16:1, particularly of about 4:1 to about 10:1 and more particularly of about 6:1 to about 8:1. The DAR may be calculated from a statistical distribution according to known methods. In some aspects, the ADC has a DAR of 8:1. In some aspects, the ADC has a DAR of 8, or the ADC has substantially homogenous DAR of 8, for example where at least about 50%, 60%, 70%, 80%, 90%, 95%, 96%, 97%, 98%, 99%, or more of the ADC has a DAR of 8.

In some aspects, it may be desirable to obtain a composition comprising an ADC (or population of ADCs) in which the DAR of the ADC (or population of ADCs) is substantially homogenous DAR, where at least about 80%, 90%, 95%, 96%, 97%, 98%, or 99% of the ADCs have a selected DAR of 1-8. In some aspects of the disclosed ADCs and compositions comprising the discloses ADCs, a composition comprising the ADCs has a substantially homogenous DAR where at least about 80%, 90%, 95%, 96%, 97%, 98%, or 99% of the ADCs have a DAR selected from 2, 4, 6, or 8. In some aspects of the disclosed ADCs and compositions comprising the discloses ADCs, a composition comprising the ADCs has a substantially homogenous DAR where at least about 80%, 90%, 95%, 96%, 97%, 98%, or 99% of the ADCs have a DAR of 8.

A composition comprising the disclosed ADC (or population of ADCs) may comprise ADCs having an average DAR. In some embodiments, a composition comprising the disclosed ADC (or population of ADCs), comprises ADCs having an average DAR which is a value within a range of 1-8 inclusive. In some embodiments, the average DAR is greater than about 1, 2, 3, 4, 5, 6, or 7.

Anti-Nectin-4 ADCs Comprising an Exatecan Payload

In a further aspect, provided herein is an ADC comprising an antibody that binds human Nectin-4 and an exatecan payload. In some aspects, the ADC comprises or is prepared from a compound of Formula (L-P), which may be utilized as a linker-payload:

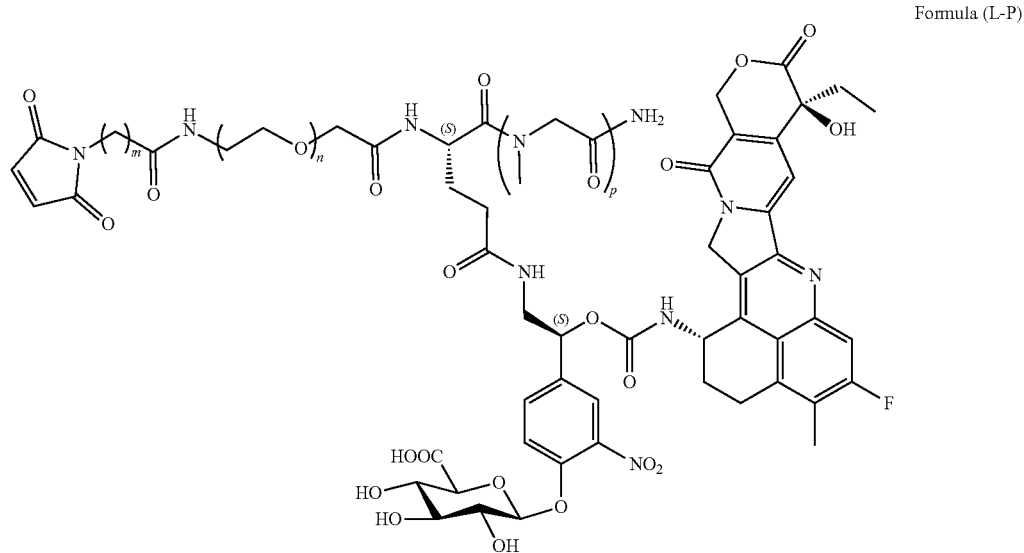

Formula (L-P)

wherein: m is selected from 1-6; n is selected from 1-6; and p is selected from 1-20.

In some embodiments of the linker-payload of Formula (L-P), m is 2.

In some embodiments of the linker-payload of Formula (L-P), n is 2.

In some embodiments of the linker-payload of Formula (L-P), p is 10.

In some aspects, the ADC comprises or is prepared from a compound of Formula (L-P'), which may be utilized as a linker-payload:

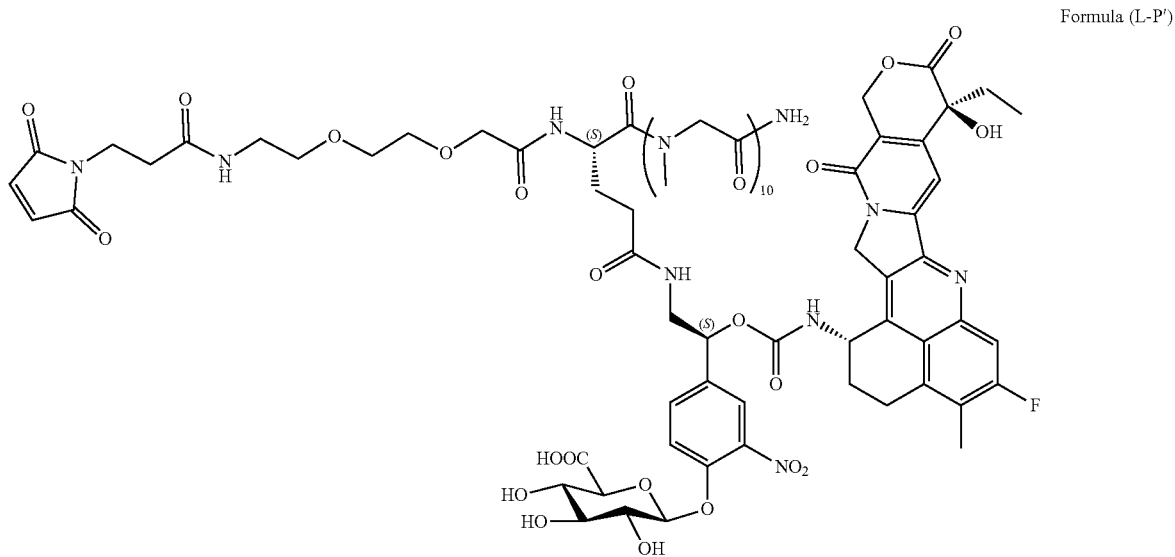

Formula (L-P')

In some aspects, the disclosed ADC comprises or is prepared using the compound: (2S,3S,4S,5R,6S)-6-(4-((3S,9S)-40-amino-9-(2-(2-(2-(3-(2,5-dioxo-2,5-dihydro-1H-pyrrol-1-yl)propanamido)ethoxy)ethoxy)acetamido)-1-(((1S,9S)-9-ethyl-5-fluoro-9-hydroxy-4-methyl-10,13-dioxo-2,3,9,10,13,15-hexahydro-1H,12R-benzo[de]pyrano[3',4':6,7]indolizino[1,2-b]quinolin-1-yl)amino)-11,14,17,20,23,26,29,323538-decamethyl-1,6,10,13,16,19,22,25,28,31,34,37,40-tridecaoxo-2-oxa-5,11,14,17,20,23,26,29,32,35,38-undecaazatetracontan-3-yl)-2-nitrophenoxy)-3,4,5-trihydroxytetrahydro-2H-pyran-2-carboxylic acid; which compound may be utilized as a linker-pay load.

In one aspect, the ADC disclosed herein is of the Formula (ADC):

philicity and reduce aggregation of the ADC. In some embodiments of the ADC of Formula (ADC), p is greater than 1, 2, 3, 4, 5, 6, 7, 8, or 9 and preferably p is 10.

In some embodiments of the ADC of Formula (ADC), p is a value small enough so as not to impair stability of the linker-payload. In some embodiments of the ADC of Formula (ADC), p is less than 20, 19, 18, 17, 16, 15, 14, 13, 12, or 11, and preferably p is 10.

In some embodiments of the ADC of Formula (ADC), DAR is a value large enough so as to provide sufficient activity for the ADC, such as sufficient toxicity. In some embodiments of the ADC of Formula (ADC), DAR is greater than 1, 2, 3, 4, 5, 6, 7, and preferably DAR is 8.

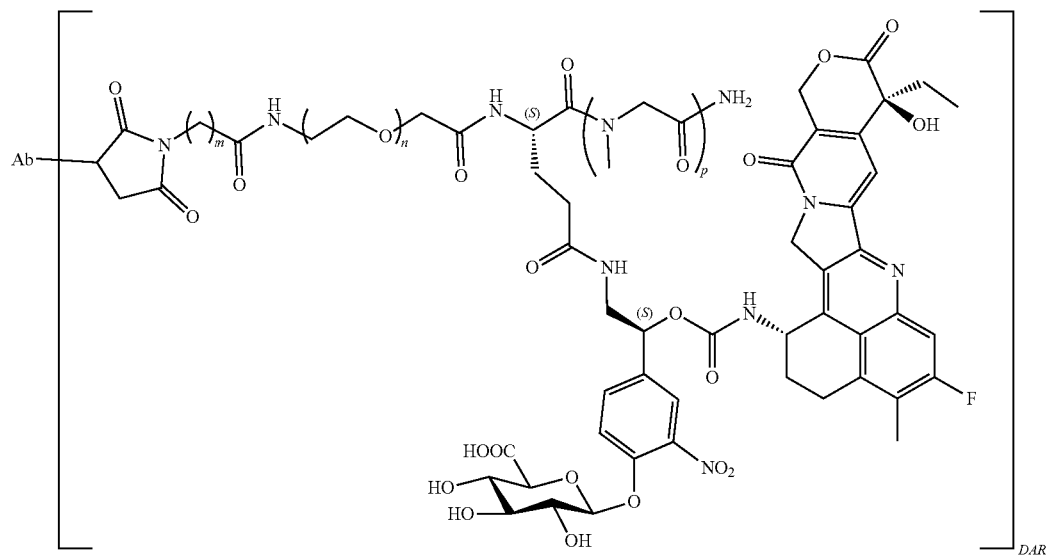

Formula (L-P')

wherein: Ab is an antibody that binds to Nectin-4 as disclosed herein; m is selected from 1-6; n is selected from 1-6; p is selected from 1-20; and DAR is from 1-8 and represents the drug-antibody ratio (DAR) of the ADC.

In some embodiments of the ADC of Formula (ADC), m is a value large enough such that the linker-payload is sufficiently spaced from the Ab portion of the ADC so as not impair activity of the Ab, which activity may include binding and binding affinity for tumor-specific Nectin-4. In some embodiments of the ADC of Formula (ADC), m is greater than 1, and preferably m is 2.

In some embodiments of the ADC of Formula (ADC), m is a value small enough so as not to impair stability of the linker-payload. In some embodiments of the ADC of Formula (ADC), m is less than 6, 5, 4, or 3, and preferably m is 2.

In some embodiments of the ADC of Formula (ADC), n is a value large enough so as to provide sufficient hydrophilicity and reduce aggregation of the ADC. In some embodiments of the ADC of Formula (ADC), n is greater than 1, and preferably n is 2.

In some embodiments of the ADC of Formula (ADC), n is a value small enough so as not to impair stability of the linker-payload. In some embodiments of the ADC of Formula (ADC), n is less than 6, 5, 4, or 3, and preferably n is 2.

In some embodiments of the ADC of Formula (ADC), p is a value large enough so as to provide sufficient hydro- In some embodiments of the ADC of Formula (ADC), at least about 50%, 60%, 70%, 80%, 90%, 95%, 96%, 97%, 98%, or 99% of the ADC has a DAR of 8. In some embodiments, the ADC of Formula (ADC) is present in a composition wherein at least 50%, 60%, 70%, 80%, 90%, 95%, 96%, 97%, 98%, or 99% of the ADC in the composition has a DAR of 8. In some embodiments, the ADC of Formula (ADC) is present in a composition wherein ADC present in the composition has an average DAR greater than about 1, 2, 3, 4, 5, 6, or 7.

In some embodiments of the ADC of Formula (ADC), the Ab is conjugated to the linker-payload via the thiol group of one or more cysteine residues. In some embodiments, the Ab is conjugated via the thiol group of one or more cysteine residues in the HC of the Ab, optionally wherein the HC has the amino acid sequence of SEQ ID NO:5 and the cysteines are selected from C222, C228, C231, and combinations thereof. In some embodiments, the Ab is conjugated via the thiol group of one or more cysteine residues in the LC of the Ab, optionally wherein the LC has the amino acid sequence of SEQ ID NO:6 and the cysteine is C214. In some embodiments of the ADC of Formula (ADC), the Ab comprises a HC comprising the amino acid sequence of SEQ ID NO:5 and a LC comprising the amino acid sequence of SEQ ID NO:6 and the Ab is conjugated to the linker-payload via the thiol group of cysteines residues including all of C222, C228, C231 of the HC, and C214 of the LC.

In some embodiments, the ADC disclosed herein is of a Formula (ADC'),

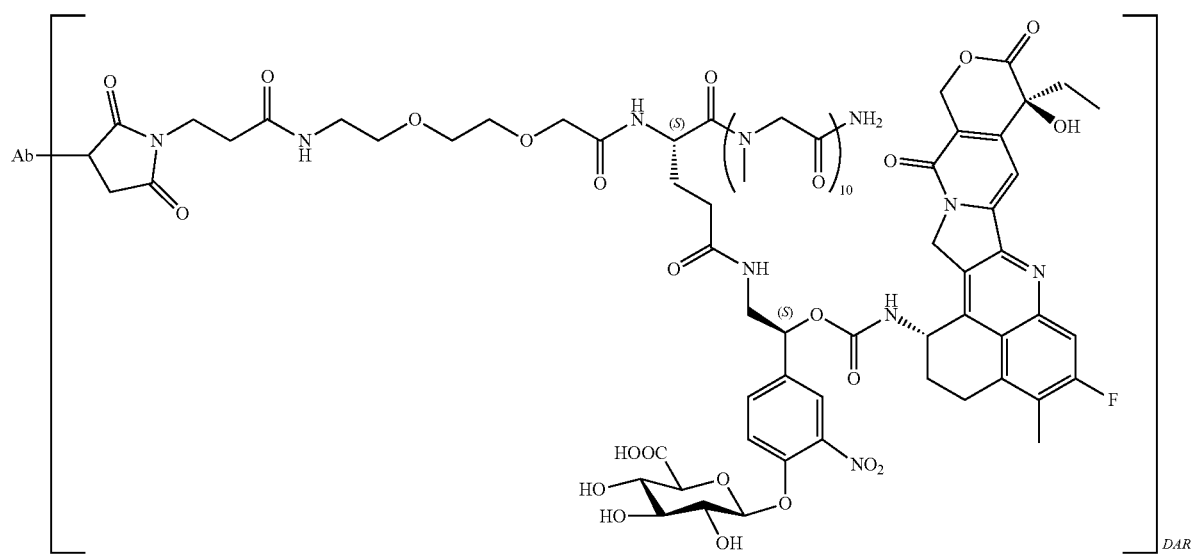

wherein DAR is from 1-8 and represents the drug-antibody ratio (DAR) of the ADC.

In some embodiments of the ADC of Formula (ADC'), DAR is a value large enough so as to provide sufficient toxicity for the DAR. In some embodiments of the ADC of Formula (ADC), DAR is greater than 1, 2, 3, 4, 5, 6, 7, and preferably DAR is 8.

In some embodiments of the ADC of Formula (ADC'), at least about 50%, 60%, 70%, 80%, 90%, 95%, 96%, 97%, 98%, or 99% of the ADC has a DAR of 8. In some embodiments of the ADC of Formula (ADC'), the ADC is present in a composition wherein at least about 50%, 60%, 70%, 80%, 90%, 95%, 96%, 97%, 98%, or 99% of the ADC in the composition has a DAR of 8. In some embodiments, the ADC of Formula (ADC') is present in a composition wherein the ADC present in the composition has an average DAR greater than about 1, 2, 3, 4, 5, 6, or 7.

In some embodiments of the ADC of Formula (ADC'), the Ab is conjugated to the linker-payload via the thiol group of one or more cysteine residues. In some embodiments, the Ab is conjugated via the thiol group of one or more cysteine residues in the HC of the Ab, optionally wherein the HC has the amino acid sequence of SEQ ID NO:5 and the cysteines are selected from C222, C228, C231, and combinations thereof. In some embodiments, the Ab is conjugated via the thiol group of one or more cysteine residues in the LC of the Ab, optionally wherein the LC has the amino acid sequence of SEQ ID NO:6 and the cysteine is C214. In some embodiments of the ADC of Formula (ADC), the Ab comprises a HC comprising the amino acid sequence of SEQ ID NO:5 and a LC comprising the amino acid sequence of SEQ ID NO:6 and the Ab is conjugated to the linker-payload via the thiol group of cysteines residues including all of C222, C228, C231 of the HC, and C214 of the LC.

In another aspect, provided herein is ADC of the Formula (ETx-22):

Formula (ETx-22)

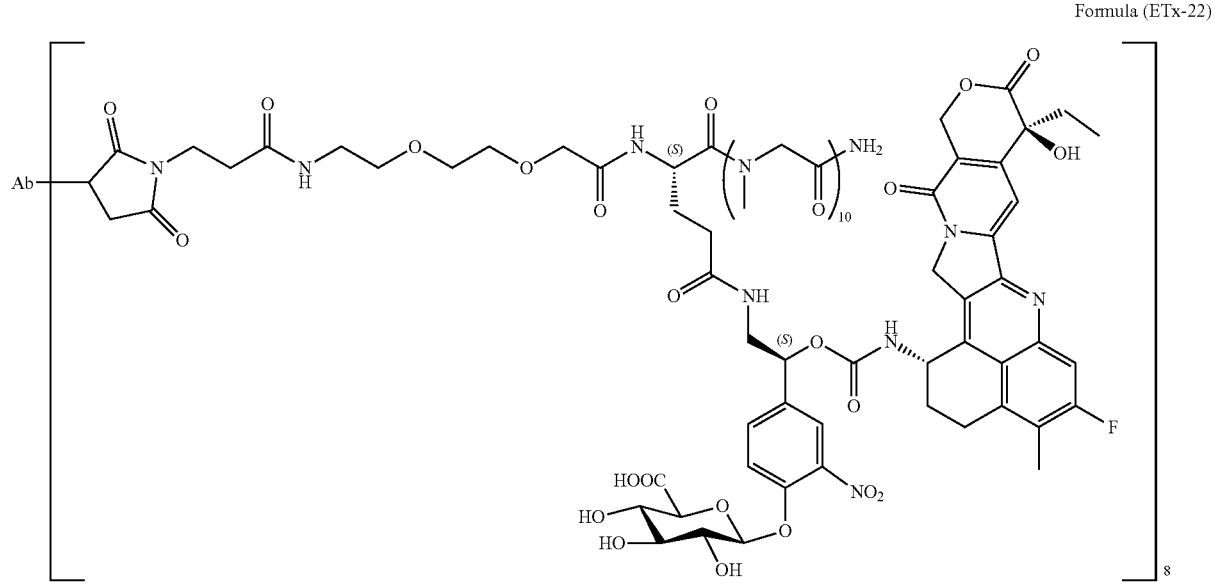

wherein Ab is an antibody that binds to Nectin-4 as disclosed herein. The Ab of Formula (ETx-22) comprises two HCs comprising the amino acid sequence of SEQ ID NO:5 and two LC comprising the amino acid sequence of SEQ ID NO:6 and the Ab is conjugated to the linker payload in Formula (ETx-22) via thiol groups in C222, C228, and C231 of both HCs of the Ab and via a thiol group in C214 of both chains of the LC, providing a DAR of 8 (i.e., 4 cysteine-maleimide linkages for each arm of the Ab).

As indicated, an ADC of Formula (ETx-22) comprises a linker comprising a 3-maleimido-propionyl spacer, a PEG2 spacer (i.e., —CH2-CH2-O-CH2-CH2-O—), a PSAR10 group (i.e., —(N(CH3)-CH2-C(O))$_{10}$—) which is located in a position in the linker characterized as orthogonal relative to the payload, and a self-immolative unit comprising 4-beta-glucuronide-3-nitro-octopamine.

In some aspects, the Ab of Formula (ETx-22) comprises a heavy chain variable region (HCVR) and a light chain variable region (LCVR), wherein the HCVR comprises heavy chain complementarity determining regions (HCDR) HCDR1, HCDR2, and HCDR3, and the LCVR comprises light chain complementarity determining regions (LCDR) LCDR1, LCDR2, and LCDR3, wherein: (a) the HCDR1 comprises SEQ ID NO: 9, the HCDR2 comprises SEQ ID NO: 10, the HCDR3 comprises SEQ ID NO: 11, the LCDR1 comprises SEQ ID NO: 12, the LCDR2 comprises SEQ ID NO: 13, and the LCDR3 comprises SEQ ID NO: 14 (all Kabat numbering); or (b) the HCDR1 comprises SEQ ID NO: 15, the HCDR2 comprises SEQ ID NO: 16, the HCDR3 comprises SEQ ID NO: 17, the LCDR1 comprises SEQ ID NO: 18, the LCDR2 comprises SEQ ID NO: 19, and the LCDR3 comprises SEQ ID NO: 20 (all IMGT numbering).

In some aspects, the Ab of the ADC of Formula (ETx-22) comprises a heavy chain variable region (VH) and a light chain variable region (VL), wherein the HCVR comprises SEQ ID NO: 7 and the LCVR comprises SEQ ID NO: 8.

In some aspects, the Ab of the ADC of Formula (ETx-22) comprises a heavy chain (HC) and a light chain (LC), wherein the HC comprises SEQ ID NO: 5 and the LC comprises SEQ ID NO: 6.

In some aspects, the ADC of Formula (ETx-22) comprises or is prepared using a compound as a linker-payload: (2S, 3S,4S,5R,6S)-6-(4-((3S,9S)-40-amino-9-(2-42-(2-(3-(2,5-dioxo-2,5-dihydro-1H-pyrrol-1-yl)propanamido)ethoxy)ethoxy)acetamido)-1-(((1S,9S)-9-ethyl-5-fluoro-9-hydroxy-4-methyl-10.13-dioxo-2,3,9,10,13,15-hexahydro-111,121-benzo[de]pyrano[3',4':6,7]indolizino[1,2-b]quinolin-1-yl) amino)-11,14,17,20,23,26,29,32,35,38-decamethyl-1,6,10, 13,16,19,22,25,28,31,34,37,40-tridecaoxo-2-oxa-5,11,14, 17,20,23,26,29,32,35,38-undecaazatetracontan-3-yl)-2-nitrophenoxy)-3,4,5-trihydroxytetrahydro-21-pyran-2-carboxylic acid.

In some aspects, the ADC of Formula (ETx-22) is prepared by conjugating: (i) a mAb; and (ii) a linker-payload: (2S,3S,4S,5R,6S)-6-(4-((3,9S)-40-amino-9-(2-(2-(2-(3-(2, 5-dioxo-2,5-dihydro-1-t-pyrrol-1H-yl)propanamido) ethoxy)ethoxy)acetamido)-1-(((1S,9S)-9-ethyl-5-fluoro-9-hydroxy-4-methyl-10,13-dioxo-2,3,9,10,13,15-hexahydro-1,121-benzo[de]pyrano[3',4':6,7]indolizino[1,2-b]quinolin-1-yl)amino)-11,14,17,20,23,26,29,32,35,38-decamethyl-1, 6,10,13,16,19,22,25,28,31,34,37,40-tridecaoxo-2-oxa-5,11, 14,17,20,23,26,29,32,35,38-undecaazatetracontan-3-yl)-2-nitrophenoxy)-3,4,5-trihydroxytetrahydro-2H-pyran-2-carboxylic acid. In some aspects, the disclosed ADC prepared by conjugating (i) and (ii) has a DAR of 8.

In some aspects, the ADC of Formula (ETx-22) is prepared by: (a) reducing a mAb; and (b) conjugating the reduced mAb and a linker-payload a linker-payload: (2S, 3S,4S,5R,6S)-6-(4-((3S,9S)-40-amino-9-(2-(2-(2-(3-(2,5-dioxo-2,5-dihydro-1H-pyrrol-1-yl)propanamido)ethoxy) ethoxy)acetamido)-1-(((1S,9S)-9-ethyl-5-fluoro-9-hydroxy-4-methyl-10,13-dioxo-2,3,9,10,13,15-hexahydro-11,12H1-benzo[de]pyrano3',4:6,7]indolizinol[1,2-b]quinolin-]-yl) amino)-11,14,17,20,23,26,29,32,35,38-decamethyl-1,6,10, 13,16,19,22,25,28,31,34,37,40-tridecaoxo-2-oxa-5,11,14, 17,20,23,26,2932,35,38-undecaazatetracontan-3-yl)-2-nitrophenoxy)-3,4,5-trihydroxytetrahydro-2H-pyran-2-carboxylic acid. In some aspects, the disclosed ADC prepared by steps (a) and (b) has a DAR of 8.

In some aspects, the disclosed ADC is prepared by conjugating: (i) a mAb comprising a HC, comprising the amino sequence of SEQ ID NO:5 and a LC comprising the LC of SEQ ID NO:6; and (ii) (2S,3S,4S,5R,6S)-6-(4-((3S, 9S)-40-amino-9-(2-(2-(2-(3-(2,5-dioxo-2,5-dihydro-1H-pyrrol-1-yl)propanamido)ethoxy)ethoxy)acetamido)-1-(((1S,9S)-9-ethyl-5-fluoro-9-hydroxy-4-methyl-10,13-dioxo-2,3,9,10,13,15-hexahydro-1-1,121-benzo[de]pyrano [3',4':6,7]indolizino[1,2-b]quinolin-1-yl)amino)-11,14,17, 20,23,26,29,32,35,38-decamethyl-1,6,10,13,16,19,22,25, 28,31,34,37,40-tridecaoxo-2-oxa-5,11,14,17,20,23,26,29, 32,35,38-undecaazatetracontan-3-yl)-2-nitrophenoxy)-3,4, 5-trihydroxytetrahydro-211-pyran-2-carboxylic acid. In some aspect, the disclosed ADC is prepared by first reducing the mAb prior to performing conjugating, and conjugating the reduced mAb to the linker payload. In some aspects, the disclosed ADC prepared by conjugating the reduced mAb and the linker-payload has a DAR of 8.

Structural Features and Activity of an ADC of Formula (ETx-22)

The ADC referred to as ETx-22 has the following formula:

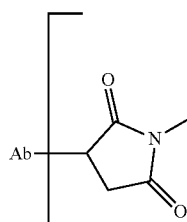
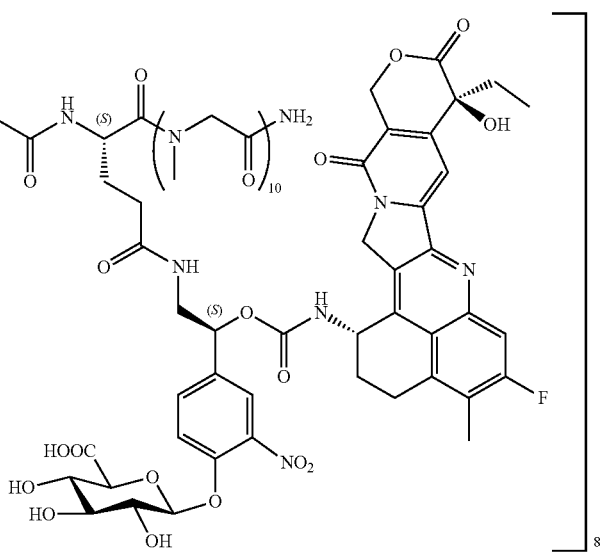

wherein Ab is an antibody that binds to Nectin-4 as disclosed herein, comprising two HCs comprising the amino acid sequence of SEQ ID NO:5 and two LC comprising the amino acid sequence of SEQ ID NO:6. The Ab is conjugated to the linker payload in Formula (ETx-22) via thiol groups in C222, C228, and C231 of both HCs of the Ab and via a thiol group in C214 of both chains of the LC, providing a DAR of 8 (i.e., where ETx-22 comprises 4 cysteine-maleimide linkages for each arm of the Ab).

As indicated, the ADC of Formula (ETx-22) has distinct structural features related to the anti-Nectin-4 antibody and the linker-payload of the ADC of Formula (ETx-22). In some aspects, these distinct structural features of the ADC of Formula (ETx-22), or the combinations thereof, impart desirable activities to the ADC of Formula (ETx-22).

In one aspect, the ADC of Formula (ETx-22) comprises the H1L2_15A7.5 anti-Nectin-4 mAb, comprising a HC of SEQ ID NO:5 and LC of SEQ ID NO:6, which exhibits desirable selectivity. In one aspect, the H1L2_15A7.5 anti-Nectin-4 mAb exhibits desirable selectivity for human Nectin-4 relative to other Nectin proteins such as human Nectin-1, Nectin-2, or Nectin-3. In one aspect, the H1L2_15A7.5 anti-Nectin-4 mAb exhibits desirable selectivity for Nectin-4 expressed by tumors in comparison to Nectin-4 expressed by normal cells, such as normal human endothelial keratinocytes.

In one aspect, the ADC of Formula (ETx-22) has a DAR of 8. In one aspect, the ADC of Formula (ETx-22) has a DAR of 8 which provides desirable toxicity and potency. In one aspect, the ADC of Formula (ETx-22) has a DAR of 8, and the ADC exhibits a minimal amount of aggregation. In one aspect, the ADC of Formula (ETx-22) has a DAR of 8 and the linker of ETx-22 minimizes aggregation. In one aspect, the linker has a sufficient length to minimize aggregation. In one aspect, the linker is sufficiently hydrophilic to minimize aggregation.

As indicated, the ADC of Formula (ETx-22) comprises a linker, and the linker comprises or is prepared from a 3-maleimido-propionyl spacer, a PEG2 spacer (i.e., —CH$_2$—CH$_2$—O—CH$_2$—CH$_2$—O—), a PSAR10 group (i.e., —(N(CH$_3$)—CH$_2$-C(O))$_{10}$—) which may be in a position characterized as orthogonal to the payload, and a self-immolative unit comprising a 4-beta-glucuronide-3-nitro-octopamine group. In one aspect, one or more of these features of the linker minimizes aggregation of the ADC of Formula (ETx-22). In one aspect, one or more of these structural features provide sufficient length to minimize aggregation of the ADC of Formula (ETx-22). In one aspect, one or more of these structural features of the linker provide sufficient hydrophilicity to the ADC of Formula (ETx-22) to minimize aggregation of the ADC.

In one aspect, the ADC of Formula (ETx-22) comprises a linker comprising a spacer with a sufficient length to position the linker-payload at a distance from the anti-Nectin-4 antibody such that the conjugated linker-payload does not substantially interfere with the activity of the anti-Nectin-4 antibody, such as the activity of Nectin-4 binding and affinity. In one aspect, the ADC of Formula (ETx-22) comprises a linker comprising a spacer with a small enough length so as not to impair the stability of the linker-payload.

As indicated, the ADC of Formula (ETx-22) comprises a linker, and the linker comprises or is prepared from a 3-maleimido-propionyl spacer, a PEG2 spacer (i.e., —CH$_2$—CH$_2$—O—CH$_2$—CH$_2$—O—), a PSAR10 group (i.e., —(N(CH$_3$)—CH$_2$-C(O))$_{10}$—) which may be in a position characterized as orthogonal with respect to the payload, and a self-immolative unit comprising a 4-beta-glucuronide-3-nitro-octopamine group. In one aspect, one or more of these structural features may provide for desirable spacing of the linker-payload from the anti-Nectin-4 antibody.

In one aspect, the ADC of Formula (ETx-22) comprises a linker that exhibits desirable stability. In one aspect, an ADC of Formula (ETx-22) comprises a linker that exhibits desirable stability in plasma. In one aspect, stability in plasma may be measured by determining a DAR for the ADC versus time after the ADC is placed in plasma.

As indicated, an ADC of Formula (ETx-22) comprises a linker, and the linker comprises or is prepared from a 3-maleimido-propionyl spacer, a PEG2 spacer (i.e., —CH$_2$—CH$_2$—O—CH$_2$—CH$_2$-O—), a PSAR10 group (i.e., —(N(CH$_3$)—CH$_2$—C(O))$_{10}$—) which may be in a position characterized as orthogonal with respect to the payload, and a self-immolative unit comprising a 4-beta-glucuronide-3-nitro-octopamine group. In one aspect, one or more of these structural features may provide for desirable stability of the linker-payload in the bloodstream.

In one aspect, the ADC of Formula (ETx-22) comprises a linker that exhibits selective cleavability. In one aspect, the ADC of Formula (ETx-22) comprises a linker that stays intact while the ADC is in the bloodstream and is cleaved only after the ADC is delivered to the tumor site. In some aspects, the tumor targeted by the ADC of Formula (ETx-22) expresses an enzyme that cleaves a components of the linker. In some aspects, the tumor expresses a beta-glucuronidase that cleaves the beta-glucuronide of the linker.

As indicated, the ADC of Formula (ETx-22) comprises a self-immolative unit comprising or prepared from a beta-glucuronide group, which may function as a triggering group, and a 3-nitro-octopamine group which undergoes rearrangement and self-immolative cleavage. In one aspect, the self-immolative unit provides for selective cleavability, where cleavage is not triggered until the beta-glucuronide is cleaved by a beta-glucuronidase in a targeted tumor cell. In one aspect, the ADC of ETx-22 is delivered to a tumor that expresses intracellular beta-glucuronidase, preferably at a relatively high level. In one aspect, the beta-glucuronide group is cleaved from the self-immolative unit, and then the self-immolative group undergoes rearrangement and self-immolative cleavage, thereby releasing the exatecan payload.

Therapeutic Applications

In another aspect, provided herein are methods of treating cancer, comprising administering to a patient in need thereof, an effective amount of a Nectin-4 ADC or pharmaceutical composition described herein. In a further aspect, provided herein is a method of treating cancer, comprising administering to a patient in need thereof, an effective amount of an ADC or pharmaceutical composition described herein, wherein the cancer is bladder cancer, breast cancer, lung cancer, gastric cancer, esophageal cancer, colorectal cancer, pancreatic cancer, head and neck cancer, ovarian cancer, or prostate cancer.

In another aspect, provided herein is an ADC comprising a Nectin-4 binding agent and exatecan for use in a method comprising administering the ADC to a patient suffering from a Nectin-4 expressing cancer, optionally wherein the cancer is resistant to treatment with an ADC comprising a Nectin-4-binding agent and an auristatin, such as monomethyl auristatin E (MMAE). In another aspect, provided herein is the use of an ADC comprising a Nectin-4 binding agent and exatecan for the manufacture of a medicament for the treatment of a patient suffering from a Nectin-4 expressing cancer, optionally wherein the cancer is resistant to treatment with an ADC comprising a Nectin-4-binding agent and an auristatin, such as monomethyl auristatin E (MMAE). In still another aspect, provided herein is a method for the treatment of a Nectin-4 expressing cancer comprising administering a therapeutically effective amount of a conjugate comprising a Nectin-4 binding agent and exatecan to a patient in need thereof, optionally wherein the disorder is cancer that is resistant to treatment with an ADC comprising a Nectin-4-binding agent and an auristatin, such as monomethyl auristatin E (MMAE).

In a further aspect, provided is a method of treating cancer, wherein the cancer is bladder cancer. In a further aspect, provided is a method of treating cancer, wherein the cancer is urothelial carcinoma. In a further aspect, provided is a method of treating cancer, wherein the cancer is breast cancer. In a further aspect, provided is a method of treating cancer, wherein the cancer is lung cancer. In a further aspect, provided is a method of treating cancer, wherein the cancer is gastric cancer. In a further aspect, provided is a method of treating cancer, wherein the cancer is esophageal cancer. In a further aspect, provided is a method of treating cancer, wherein the cancer is colorectal cancer. In a further aspect, provided is a method of treating cancer, wherein the cancer is pancreatic cancer. In a further aspect, provided is a method of treating cancer, wherein the cancer is head and neck cancer. In a further aspect, provided is a method of treating cancer, wherein the cancer is ovarian cancer. In a further aspect, provided is a method of treating cancer, wherein the cancer is prostate cancer.

In a further aspect, the patient has relapsed after being administered enfortumab vedotin, or the patient has become refractory to enfortumab vedotin or to standard of care treatments. In a further aspect, the patient being treated with an ADC or pharmaceutical composition described herein is ineligible for treatment with enfortumab vedotin. In a further aspect, the patient has a cancer that is resistant to treatment with an auristatin such as monomethyl auristatin E (MMAE).

In a further aspect, the patient being treated with an ADC or pharmaceutical composition described herein previously received a programmed death receptor-1 (PD-1) or programmed death-ligand 1 (PD-L1) inhibitor, and a platinum-containing chemotherapy in the neoadjuvant/adjuvant, locally advanced or metastatic setting. In a further aspect, the patient being treated with an ADC or pharmaceutical composition described herein in combination with a PD-1 inhibitor or PD-L1 inhibitor is ineligible for treatment with cisplatin-containing chemotherapy.

In a further aspect, provided are methods comprising the administration of an effective amount of an ADC or pharmaceutical composition described herein in simultaneous, separate, or sequential combination with one or more antitumor agents. In a further aspect, provided are methods comprising the administration of an effective amount of an ADC or pharmaceutical composition described herein in simultaneous, separate, or sequential combination with a PD-1 inhibitor or PD-L1 inhibitor. In one aspect, the patient is subjected to a diagnostic test that measures expression of PD-1 or PD-L1 by the patient's cancer prior to simultaneous, separate, or sequential administration of the PD-1 inhibitor or PD-L1 inhibitor.

In another aspect, provided herein are methods comprising administration of an effective amount of a Nectin-4 ADC or pharmaceutical composition described herein in simultaneous, separate, or sequential combination with a FGFR compound. In a further aspect, wherein the cancer is urothelial carcinoma. In a further aspect, wherein the FGFR compound is erdafitinib, LOXO-435, futibatinib, vofatamab, bemarituzumab, derazantinib, infigratinib, pemigatinib, rogaratinib, FGF401, or pemigatinib. In some embodiments, the Nectin-4 ADC is administered to a patient having a cancer that is resistant to treatment with erdafitinib.

In another aspect, provided herein is a Nectin-4 ADC or pharmaceutical composition described herein, for use in therapy. In a further aspect, provided is an ADC or pharmaceutical composition described herein, for use in the treatment of cancer. In a further aspect, the cancer is urothelial carcinoma, breast cancer, lung cancer, gastric cancer, esophageal cancer, colorectal cancer, pancreatic cancer, head and neck cancer, ovarian cancer, or prostate cancer.

In a further aspect, provided herein is a Nectin-4 ADC or pharmaceutical composition described herein, for use in the treatment of bladder cancer. In a further aspect, provided herein is a Nectin-4 ADC or pharmaceutical composition described herein, for use in the treatment of urothelial carcinoma. In a further aspect, provided herein is an ADC or pharmaceutical composition described herein, for use in the treatment of breast cancer. In a further aspect, provided herein is an ADC or pharmaceutical composition described herein, for use in the treatment of lung cancer. In a further aspect, provided herein is an ADC or pharmaceutical composition described herein, for use in the treatment of gastric cancer. In a further aspect, provided herein is an ADC or pharmaceutical composition described herein, for use in the treatment of esophageal cancer. In a further aspect, provided herein is an ADC or pharmaceutical composition described herein, for use in the treatment of colorectal cancer. In a further aspect, provided herein is an ADC or pharmaceutical composition described herein, for use in the treatment of pancreatic cancer. In a further aspect, provided herein is an ADC or pharmaceutical composition described herein, for use in the treatment of head and neck cancer. In a further aspect, provided herein is an ADC or pharmaceutical composition described herein, for use in the treatment of ovarian cancer. In a further aspect, provided herein is an ADC or pharmaceutical composition described herein, for use in the treatment of prostate cancer.

In a further aspect, provided herein is a Nectin-4 ADC or pharmaceutical composition described herein, for use in the treatment of cancer, wherein the cancer has relapsed after treatment with enfortumab vedotin, or the cancer has become refractory to enfortumab vedotin. In a further aspect, provided herein is a Nectin-4 ADC of pharmaceutical composition described herein, for use in the treatment of cancer, wherein the cancer is resistant to treatment with an auristatin such as monomethyl aurastatin E (MMAE). In a further aspect, provided herein is a Nectin-4 ADC or pharmaceutical composition described herein, for use in the treatment of cancer, wherein the cancer has relapsed after treatment with enfortumab vedotin, or the cancer has become refractory to standard of care treatment. In a further aspect, provided herein is an ADC or pharmaceutical composition described herein, for use in the treatment of cancer, wherein prior use of enfortumab vedotin was contraindicated.

In a further aspect, provided herein is an ADC or pharmaceutical composition described herein, for use in the treatment of cancer, wherein prior use occurred for a PD-1 or PD-L1 inhibitor, and a platinum-containing chemotherapy in the neoadjuvant/adjuvant, locally advanced or metastatic setting. In a further aspect, provided herein is an ADC or pharmaceutical composition described herein in simultaneous, separate, or sequential combination with a PD-1 inhibitor or PD-L1 inhibitor, for use in the treatment of cancer, wherein the cancer cannot be treated with cisplatin-containing chemotherapy.

In a further aspect, provided herein is an ADC or pharmaceutical composition described herein in simultaneous, separate, or sequential combination with one or more antitumor agents for use in the treatment of cancer. In a further aspect, with the antitumor agent is a PD-1 inhibitor or PD-L1 inhibitor.

In another aspect, provided herein is a Nectin-4 ADC or pharmaceutical composition described herein in simultaneous, separate, or sequential combination with a FGFR compound for use in the treatment of cancer. In a further aspect, wherein the cancer is urothelial carcinoma. In a further aspect, wherein the FGFR compound is erdafitinib, LOXO-435, futibatinib, vofatamab, bemarituzumab, derazantinib, infigratinib, pemigatinib, rogaratinib, FGF401, or pemigatinib. In another aspect, provided herein is a Nectin-4 ADC of pharmaceutical composition for use in treating cancer that is resistant to erdafitinib.

In another aspect, provided herein is the use of a Nectin-4 ADC or pharmaceutical composition described herein for the manufacture of a medicament for the treatment of cancer. In a further aspect, provided herein is the use of an ADC or pharmaceutical composition described herein for the manufacture of a medicament for the treatment of cancer, wherein the cancer is bladder cancer, breast cancer, lung cancer, gastric cancer, esophageal cancer, colorectal cancer, pancreatic cancer, head and neck cancer, ovarian cancer, or prostate cancer.

In a further aspect, provided herein is the use of a Nectin-4 ADC or pharmaceutical composition described herein for the manufacture of a medicament for the treatment of cancer, wherein the cancer has relapsed after treatment with enfortumab vedotin, or the cancer has become refractory to enfortumab vedotin or to standard of care treatment. In a further aspect, provided herein is the use of an ADC or pharmaceutical composition described herein for the manufacture of a medicament for the treatment of cancer, wherein prior use of enfortumab vedotin was contraindicated. In a further aspect, provided herein is the use of a Nectin-4 ADC or pharmaceutical composition described herein for the manufacture of a medicament for the treatment of cancer, wherein the cancer is resistant to treatment with auristatin such as monomethyl auristatin E (MMAE).

In a further aspect, provided herein is the use of an ADC or pharmaceutical composition described herein for the manufacture of a medicament for the treatment of cancer, wherein prior use of a PD-1 or PD-L1 inhibitor, and a platinum-containing chemotherapy in the neoadjuvant/adjuvant, locally advanced or metastatic setting. In a further aspect, provided herein is the use of an ADC or pharmaceutical composition described herein for the manufacture of a medicament for the treatment of cancer, wherein the cancer cannot be treated with cisplatin-containing chemotherapy and wherein said medicament is to be administered simultaneously, separately, or sequentially with a PD-1 inhibitor or PD-L1 inhibitor.

In a further aspect, provided herein is the use of an ADC or pharmaceutical composition described herein in the manufacture of a medicament for the treatment of cancer wherein said medicament is to be administered simultaneously, separately, or sequentially with one or more antitumor agents. In a further aspect, provided herein is the use of an ADC or pharmaceutical composition described herein in the manufacture of a medicament for the treatment of cancer wherein said medicament is to be administered simultaneously, separately, or sequentially with a PD-1 inhibitor or PD-L1 inhibitor.

In another aspect, provided herein is the use of a Nectin-4 ADC or pharmaceutical composition described herein in the manufacture of a medicament for the treatment of cancer wherein said medicament is to be administered simultaneously, separately, or sequentially with a FGFR compound. In a further aspect, wherein the cancer is urothelial carcinoma. In a further aspect, wherein the FGFR compound is erdafitinib, LOXO-435, futibatinib, vofatamab, bemarituzumab, derazantinib, infigratinib, pemigatinib, rogaratinib, FGF401, or pemigatinib. In another aspect, provided herein is the use of a Nectin-4 ADC or pharmaceutical composition described herein in the manufacture of a medicament for the treatment of cancer that is resistant to treatment with erdafinitib.

In a further aspect, the bladder cancer is urothelial carcinoma, squamous cell carcinoma, or adenocarcinoma. In a further aspect, the bladder cancer is noninvasive, non-muscle-invasive, or muscle invasive. In a further aspect, the bladder cancer is of the bladder, renal pelvis, ureter, or urethra. In a further aspect, the breast cancer is HR-positive, HER2-negative breast cancer, or triple negative breast cancer (TNBC). In a further aspect, the breast cancer is ductal or lobular. In a further aspect, the lung cancer is squamous non-small cell lung cancer (NSCLC) or non-squamous NSCLC. In a further aspect, the lung cancer is squamous, adenocarcinoma, or small cell carcinoma. In a further aspect, the prostate cancer is metastatic castration-resistant prostate cancer. In a further aspect, the gastric cancer is stomach cancer. In a further aspect, the gastric cancer or esophageal cancer is gastroesophageal junction cancer. In a further aspect, the ovarian cancer is serous or mucinous. In a further aspect, the ovarian cancer is fallopian or peritoneal.

In a further aspect, the antitumor agents may be chemotherapeutic therapeutic agents, including platinum-containing chemotherapy, and/or may include cisplatin, carboplatin, dacarbazine, liposomal doxorubicin, docetaxel, cyclophosphamide and doxorubicin, navelbine, eribulin, paclitaxel, paclitaxel protein-bound particles for injectable suspension, ixabepilone, capecitabine, FOLFOX (leucovorin, fluorouracil, and oxaliplatin), FOLFIRI (leucovorin, fluorouracil, and irinotecan), gemcitabine, topotecan, liposomal irinotecan, pemetrexed, and cetuximab. In a further aspect, the antitumor agents may be immuno-oncology agents, including those selected from the group consisting of nivolumab, ipilimumab, pidilizumab, pembrolizumab, tremelimumab, urelumab, lirilumab, atezolizumab, epacadostat, and durvalumab.

Pharmaceutical Compositions and Methods of Administration

The ADCs described herein can be formulated as pharmaceutical compositions administered by any route which makes the antibody or ADC bioavailable including, for example, oral, topical, or subcutaneous administration.

Also provided herein is a pharmaceutical composition comprising an ADC provided herein and one or more agents selected from the group consisting of a physiologically acceptable carrier, a diluent, an excipient, and an auxiliary.

The ADCs of the present disclosure, or pharmaceutical compositions comprising the same, may be administered by parenteral routes (e.g., subcutaneous and intravenous). An ADC of the present disclosure may be administered to a patient alone with pharmaceutically acceptable carriers, diluents, or excipients in single or multiple doses. Pharmaceutical compositions described herein can be prepared by methods well known in the art (e.g., Remington: The Science and Practice of Pharmacy, 22nd ed. (2012), A. Loyd et al., Pharmaceutical Press) and comprise an antibody or ADC, as disclosed herein, and one or more pharmaceutically acceptable carriers, diluents, or excipients.

In an aspect, disclosed herein is a pharmaceutical composition comprising an antibody disclosed herein and one or more pharmaceutically acceptable carriers, diluents, or excipients. In an aspect, disclosed herein is a pharmaceutical composition comprising an ADC disclosed herein and one or more pharmaceutically acceptable carriers, diluents, or excipients.

Dosing, Regimens, and Cycles

The disclosed Nectin-4 ADCs may be administered in methods of treating cancer that administering to a patient in need thereof, an effective amount of a Nectin-4 ADC or pharmaceutical composition described herein. A patient may be administered an effective amount by modulating the dose, dosing regimen, or dosing cycle for the Nectin-4 ADCs.

In one aspect, the ADCs of the present disclosure, or pharmaceutical compositions comprising the same, may be administered by parenteral routes (e.g., subcutaneous and intravenous).

Definitions

As used herein, the terms "a," "an," "the," and similar terms used in the context of the present disclosure (especially in the context of the claims) are to be construed to cover both the singular and plural unless otherwise indicated herein or clearly contradicted by the context.

The terms "bind" and "binds" as used herein, are intended to mean, unless indicated otherwise, the ability of a protein or molecule to form a chemical bond or attractive interaction with another protein or molecule, which results in proximity of the two proteins or molecules as determined by common methods known in the art.

As used herein, the term "effective amount" refers to an amount necessary (for periods of time and for the means of administration) to achieve the desired therapeutic result. An effective amount of a protein or conjugate may vary according to factors such as the disease state, age, sex, and weight of the individual, and the ability of the protein or conjugate to elicit a desired response in the individual. An effective amount is also one in which any toxic or detrimental effects of the protein or conjugate are outweighed by the therapeutically beneficial effects.

As used herein, the terms "treating", "treatment", or "to treat" refers to all processes wherein there may be a slowing, controlling, delaying, or stopping of the progression of the disorders or disease disclosed herein, or ameliorating disorder or disease symptoms, but does not necessarily indicate a total elimination of all disorder or disease symptoms.

The term "patient" or "subject" as used herein, refers to a human patient or human subject, respectively. The term "patient" and "subject" may be used interchangeably herein.

Certain abbreviations are defined as follows: "ACN" refers to acetonitrile; "Boc2O refers to Di-tert-butyl decarbonate; "DCM" refers to dichloromethane; "DIPEA" refers to N,N-diisopropylethylamine; "DBU" refers to 1,8-diazabicyclo[5.4.0]undec-7-ene; "DMTMM" refers to (4-(4,6-dimethoxy-1,3,5-triazin-2-yl)-4-methyl-morpholinium chloride; "DMAC" refers to dimethylacetamide; "DMF" refers to N, N-dimethylformamide; "DTT" refers to dithiothreitol; "EtOAc" refers to ethyl acetate; "EDTA" refers to ethylenediaminetetraacetic acid; "FA" refers to formic acid; "HMPA" refers to hexamethylphosphoramide; "h" refers to hour; "HEPES" refers to (N-2-hydroxyethylpiperazine-N'-2-ethanesulfonic acid); "HMTTA' refers to hexamethyltriethylenetetranine; "HATU" refers to 1-[Bis(dimethylamino) methylene]-1H-1,2,3-triazolo[4,5-b]pyridinium 3-oxide hexafluorophosphate; "HOBt" refers to Hydroxybenzotriazole; "Pyr" refers to pyridine; "NMM" refers to N-methylmorpholine; "NMP" refers to (N-methyl-2-pyrrolidone); "Su" refers to succinimide; "PPTS" refers to pyridinium p-toluenesulfonate; "THF" refers to tetrahydrofuran; "TsOH" refers to p-toluenesulfonic acid; and "TCEP" refers to (tris(2-carboxyethyl)phosphine); "TFA" refers to trifluoroacetic acid; "TEA" refers to triethylamine.

EMBODIMENTS

The following embodiments are illustrative and should not be interpreted as limiting the scope of the claims.

Embodiment 1. An antibody-drug conjugate (ADC) of the formula:

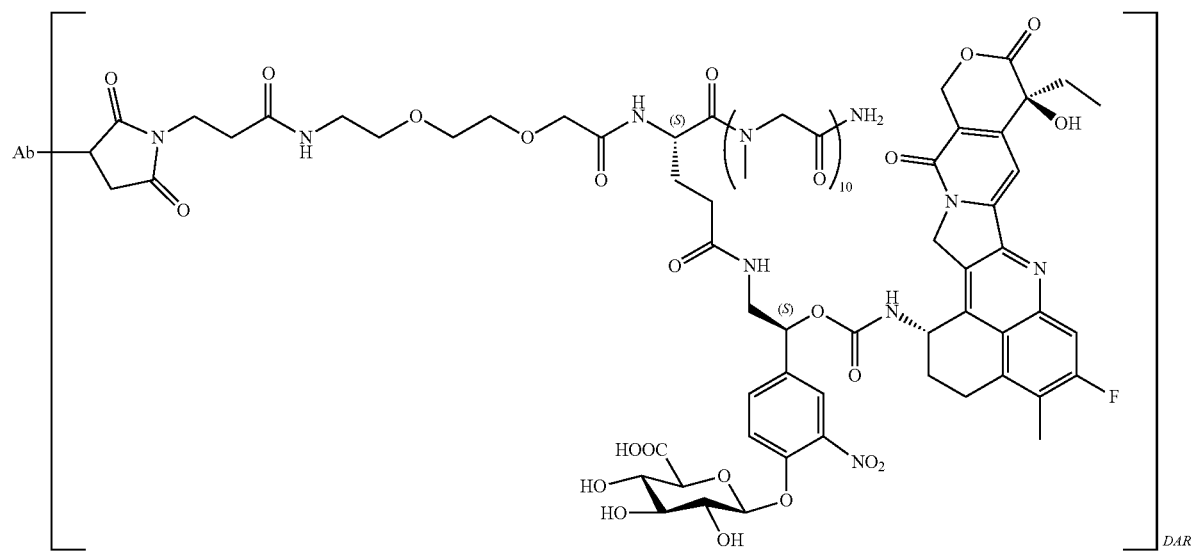

wherein: Ab is antibody that binds human Nectin-4, wherein Ab comprises a heavy chain (HC) comprising a variable region (HCVR) and a light chain (LC) comprising a variable region (LCVR), wherein the HCVR comprises heavy chain complementarity determining regions (HCDR) HCDR1, HCDR2, and HCDR3, and the LCVR comprises light chain complementarity determining regions (LCDR) LCDR1, LCDR2, and LCDR3, wherein: (i) the HCDR1 comprises SEQ ID NO: 9 (NYGMA), the HCDR2 comprises SEQ ID NO: 10 (FISNLAYGINYADTVTG), the HCDR3 comprises SEQ ID NO: 11 (GARATGWFAY), the LCDR1 comprises SEQ ID NO: 12 (KASQNVDTHVA), the LCDR2 comprises SEQ ID NO: 13 (SASYRYS), and the LCDR3 comprises SEQ ID NO: 14 (QQYNSYPLT) (all Kabat numbering); or (ii) the HCDR1 comprises SEQ ID NO: 15 (GFTFSNYG), the HCDR2 comprises SEQ ID NO: 16 (ISNLAYGI), the HCDR3 comprises SEQ ID NO: 17 (ARGARATGWFAY), the LCDR1 comprises SEQ ID NO: 18 (QNVDTH), the LCDR2 comprises SEQ ID NO: 19 (SAS), and the LCDR3 comprises SEQ ID NO: 20 (QQYNSYPLT) (all IMGT numbering); and DAR is from 1-8.

Embodiment 2. The ADC of embodiment 1, wherein the HCVR comprises SEQ ID NO:7 and the LCVR comprises SEQ ID NO:8.

Embodiment 3. The ADC of embodiment 1 or 2, wherein the HC comprises SEQ ID NO:5 and the LC comprises SEQ ID NO:6.

Embodiment 4. The ADC of any one of embodiments 1-3, wherein the Ab has a human IgG1 or IgG4 isotype.

Embodiment 5. The ADC of any one of embodiments 1-4, wherein the Ab has a human IgG1 isotype.

Embodiment 6. The ADC of any one of embodiments 1-5, wherein the Ab is conjugated via one or more thiol groups of cysteine residues present in the HC or LC.

Embodiment 7. The ADC of any one of embodiments 1-6, wherein the Ab comprises a HC having the amino acid sequence of SEQ ID NO:5 and a LC having the amino acid sequence of SEQ ID NO:6 and the Ab is conjugated via a thiol group of C222, C228, or C231 of the HC, a thiol group of C214 of the LC, or combinations thereof.

Embodiment 8. The ADC of embodiment 7, wherein the ADC has a DAR of 8 and the Ab is conjugated by a thiol group of C222, C228, and C231 of the HC, and a thiol group of C214 of the LC.

Embodiment 9. The ADC of any one of embodiments 1-8, wherein at least 95% of the ADC has a DAR of 8.

Embodiment 10. The ADC of any one of embodiments 1-8 having the formula:

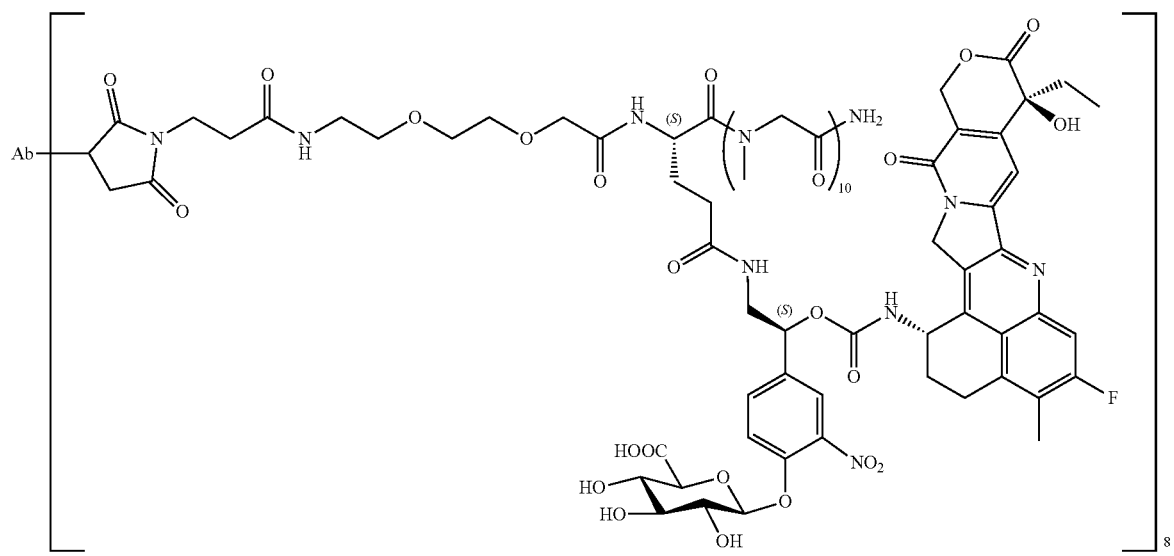

Embodiment 11. The ADC of embodiment 10, wherein the Ab comprises a HC of SEQ ID NO:5 and a LC of SEQ ID NO:6.

Embodiment 12. The ADC of embodiment 11, wherein the Ab is conjugated via cysteines at positions C222, C228, C231 of the HC and via a cysteine of C214 of the LC.

Embodiment 13. A composition comprising the ADC of any one of embodiments 1-8, wherein at least about 95% of the ADC in the composition has a DAR of 8.

Embodiment 14. A pharmaceutical composition comprising the ADC of any one of embodiments 1-12 or the composition of embodiment 13, and one or more pharmaceutically acceptable carriers, diluents, or excipients.

Embodiment 15. A method of treating cancer, the method comprising administering to a patient in need thereof, an effective amount of the ADC of any one of embodiments 1-11, the composition of embodiment 13, or the pharmaceutical composition of embodiment 14.

Embodiment 16. The method of embodiment 15, wherein the cancer is urothelial carcinoma, breast cancer, lung cancer, gastric cancer, esophageal cancer, colorectal cancer, pancreatic cancer, head and neck cancer, ovarian cancer, or prostate cancer.

Embodiment 17. The method of embodiment 15 or 16, wherein the cancer is urothelial carcinoma.

Embodiment 18. The method of any one of embodiments 15-17, wherein the cancer has relapsed after being administered enfortumab vedotin, or the cancer has become refractory to treatment with enfortumab vedotin.

Embodiment 19. The method of any one of embodiments 15-18, wherein enfortumab vedotin was administered to the patient as a first-line, second-line, or third-line treatment, prior to administering to the patient an effective amount of the ADC of any one of embodiments 1-11, the composition of embodiment 13, or the pharmaceutical composition of embodiment 14.

Embodiment 20. The method of any one of embodiments 15-17, wherein the patient is ineligible for treatment with enfortumab vedotin.

Embodiment 21. The method of any one of embodiments 15-17, wherein the cancer is resistant to treatment with monomethyl auristatin E (MMAE).

Embodiment 22. The method of any one of embodiments 15-21, wherein the cancer is characterized by growth of a primary tumor, occurrence and/or recurrence of tumor metastases, and/or increase of at least one tumor marker, and/or by an upregulation of ABCB1 expression.

Embodiment 23. The method of any one of embodiments 15-22, further comprising administrating simultaneously, separately, or sequentially a PD-1 inhibitor or PD-L1 inhibitor to the patient.

Embodiment 24. The method of embodiment 23, wherein prior to administering the PD-1 inhibitor or the PD-L1 inhibitor, the patient is administered a diagnostic test that measures expression of PD-1 or PD-L1 by the cancer.

Embodiment 25. The ADC of any one of embodiments 1-12, for use in therapy.

Embodiment 26. The ADC of any one of embodiments 1-12, for use in the treatment of cancer.

Embodiment 27. The ADC for use of embodiment 26, wherein the cancer is urothelial carcinoma, breast cancer, lung cancer, gastric cancer, esophageal cancer, colorectal cancer, pancreatic cancer, head and neck cancer, ovarian cancer, or prostate cancer.

Embodiment 28. The ADC for use of embodiment 26, wherein the cancer is urothelial carcinoma.

Embodiment 29. The ADC for use of any one of embodiments 26-28, wherein the cancer has relapsed after treatment with enfortumab vedotin, or the cancer has become refractory to treatment with enfortumab vedotin.

Embodiment 30. The ADC for use of any one of embodiments 26-29, wherein enfortumab vedotin previously was administered to the patient as a first-line, second-line, or third-line treatment, prior to administering to the patient an effective amount of the ADC of any one of embodiments 1-11, the composition of embodiment 13, or the pharmaceutical composition of embodiment 14.

Embodiment 31. The ADC for use of any one of embodiments 26-28, wherein prior use of enfortumab vedotin is contraindicated.

Embodiment 32. The ADC for use of any one of embodiments 26-28, wherein the cancer is resistant to treatment with monomethyl auristatin E (MMAE).

Embodiment 33. The ADC for use of any one of embodiments 26-32, wherein the cancer is characterized by growth of a primary tumor, occurrence and/or recurrence of tumor metastases, and/or increase of at least one tumor marker, and/or by an upregulation of ABCB1 expression.

Embodiment 34. The ADC for use of any one of embodiments 24-33, in simultaneous, separate, or sequential combination with a PD-1 inhibitor or PD-L1 inhibitor.

Embodiment 35. The ADC for use of embodiment 34, in simultaneous, separate, or sequential combination with a PD-1 inhibitor or PD-L1 inhibitor after the cancer has been identified as cancer that expresses PD-1 or PD-L1.

Embodiment 36. A pharmaceutical composition comprising an effective amount of the ADC of any one of embodiments 1-12 or an effective amount of the composition of embodiment 13 for use in treating cancer.

Embodiment 37. The composition for use of embodiment 36, wherein the cancer is urothelial carcinoma, breast cancer, lung cancer, gastric cancer, esophageal cancer, colorectal cancer, pancreatic cancer, head and neck cancer, ovarian cancer, or prostate cancer.

Embodiment 38. The composition of embodiment 36 or 37, which is administered in simultaneous, separate, or sequential combination with a PD-1 inhibitor or PD-L1 inhibitor.

Embodiment 39. The composition of embodiment 36, which is administered in simultaneous, separate, or sequential combination with a PD-1 inhibitor or PD-L1 inhibitor after the cancer has been identified as cancer that expresses PD-1 or PD-L1.

Embodiment 40. The use of an ADC of any one of embodiments 1-12 for the manufacture of a medicament for the treatment of cancer.

Embodiment 41. The use of embodiment 40, wherein the cancer is urothelial carcinoma, breast cancer, lung cancer, gastric cancer, esophageal cancer, colorectal cancer, pancreatic cancer, head and neck cancer, ovarian cancer, or prostate cancer.

Embodiment 42. The use of embodiment 40 or 41, wherein the medicament further comprises a PD-1 inhibitor or PD-L1 inhibitor.

Embodiment 43. A method of producing an ADC, the method comprising conjugating: (ii) an antibody (Ab) that binds human Nectin-4, wherein the Ab comprises a heavy chain (HC) having a variable region (HCVR) and a light chain (LC) having a variable region (LCVR), wherein the HCVR comprises heavy chain complementarity determining regions (HCDR) HCDR1, HCDR2, and HCDR3, and the LCVR comprises light chain complementarity determining regions (LCDR) LCDR1, LCDR2, and LCDR3, wherein: (a) the HCDR1 comprises SEQ ID NO: 9 (NYGMA), the HCDR2 comprises SEQ ID NO: 10 (FISNLAYGINY-ADTVTG), the HCDR3 comprises SEQ ID NO: 11 (GA-RATGWFAY), the LCDR1 comprises SEQ ID NO: 12 (KASQNVDTHVA), the LCDR2 comprises SEQ ID NO: 13 (SASYRYS), and the LCDR3 comprises SEQ ID NO: 14 (QQYNSYPLT) (all Kabat numbering); or (b) the HCDR1 comprises SEQ ID NO: 15 (GFTFSNYG), the HCDR2 comprises SEQ ID NO: 16 (ISNLAYGI), the HCDR3 comprises SEQ ID NO: 17 (ARGARATGWFAY), the LCDR1 comprises SEQ ID NO: 18 (QNVDTH), the LCDR2 comprises SEQ ID NO: 19 (SAS), and the LCDR3 comprises SEQ ID NO: 20 (QQYNSYPLT) (all IMGT numbering); and (ii) a compound of the formula:

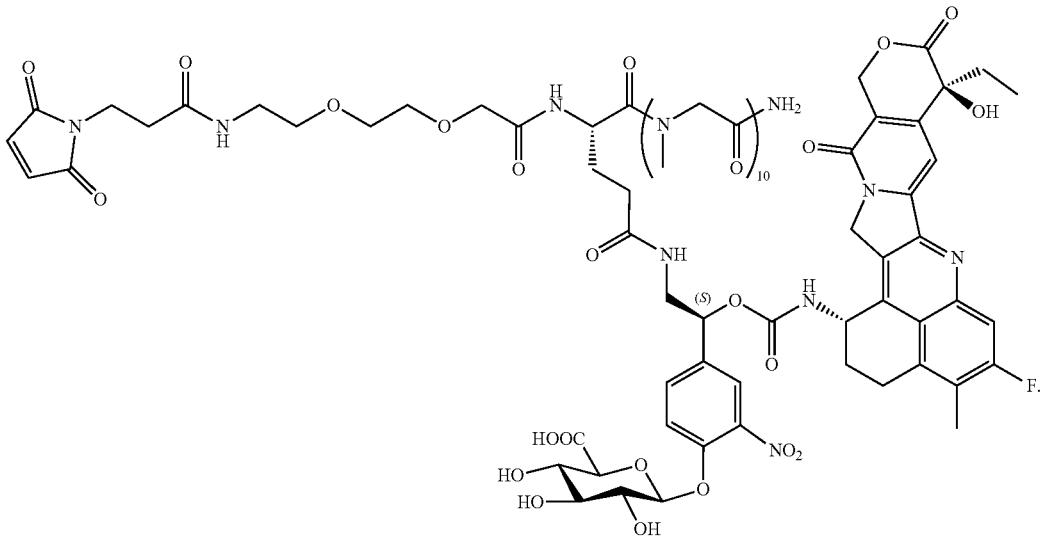

Embodiment 44. The method of embodiment 43, wherein the Ab and compound are conjugated under conditions sufficient for conjugating the Ab and the compound and providing an ADC having a DAR of 8.

Embodiment 45. The method of embodiment 43 or 44, further comprising reducing the Ab with a reducing agent to produce a reduced Ab prior to conjugating.

Embodiment 46. The method of embodiment 45, wherein the reducing agent is DTT or TCEP.

Embodiment 47. The method of any one of embodiments 43-46, wherein the compound is present in a molar excess of at least about 8 relative to the Ab during conjugation.

Embodiment 48. The method of any one of embodiments 43-46, wherein the compound is present in a molar excess of at least about 12 relative to the Ab during conjugating.

EXAMPLES

Example 1: Synthesis of Linker-Payload of Formula (L-P'): (2S,3S,4S,5R,6 S)-6-(4-((3S,9S)-40-amino-9-(2-(2-(2-(3-(2.5-dioxo-2,5-dihydro-1H-pyrrol-1-yl)propanamido)ethoxy)ethoxy)acetamido)-1-(((1S,9S-9-ethyl-5-fluoro-9-hydroxy-4-methyl-10,13-dioxo-2,3,9,10,13,15-hexahydro-1H,12-benzo[de]pyrano[3',4':6,7]indolizino[0.2-b]quinolin-1-yl)amino)-11,14,17,20,23,26,29,32,35,38-decamethyl-1,6,10,13,16,19,22,25,28,31,34,37,40-tridecaoxo-2-oxa-5,11,14,17,20,23,26,29,32,35,38-undecaazatetracontan-3-yl)-2-nitrophenoxy)-3,4,5-trihydroxytetrahydro-2H1-pyran-2-carboxylic acid

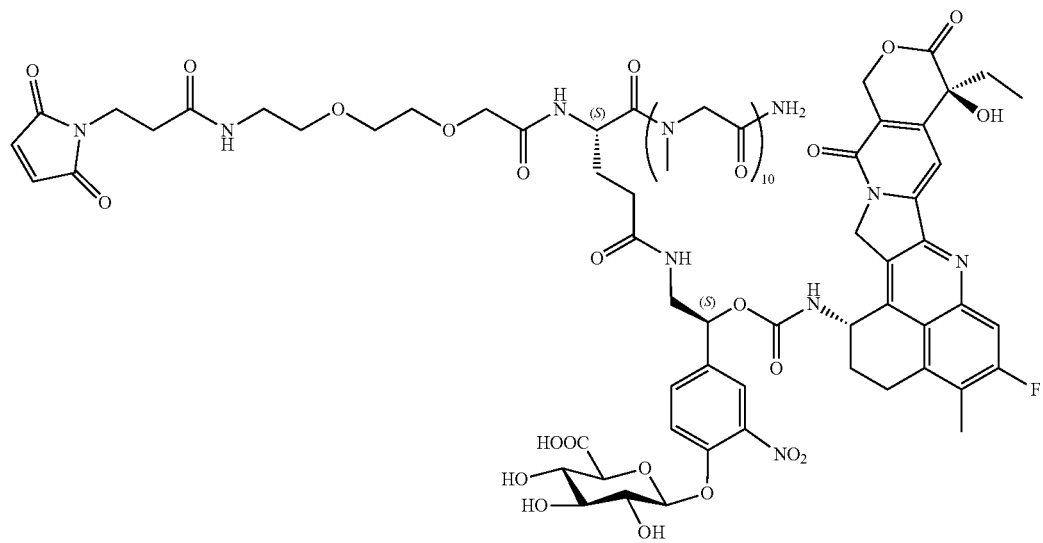

Formula (L-P'): A Linker-Pay Load

The linker-payload of Formula (L-P') was synthesized from precursors or intermediates that include: a polysarcosine (PSAR) compound; a 4-beta-glucuronide-3-nitro-octapamine compound; an exatecan compound; and a maleimido-proprionyl compound. The linker-payload was synthesized using methods disclosed in WO2019081455 and WO2022/207699.

PSAR intermediate:
FmocNH-PEG2-Glu(Su)-PSAR10-NH₂

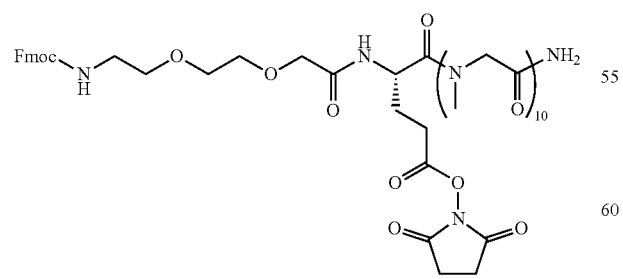

PSAR Intermediate

The PSAR intermediate may be prepared using Scheme 1.

Scheme 1

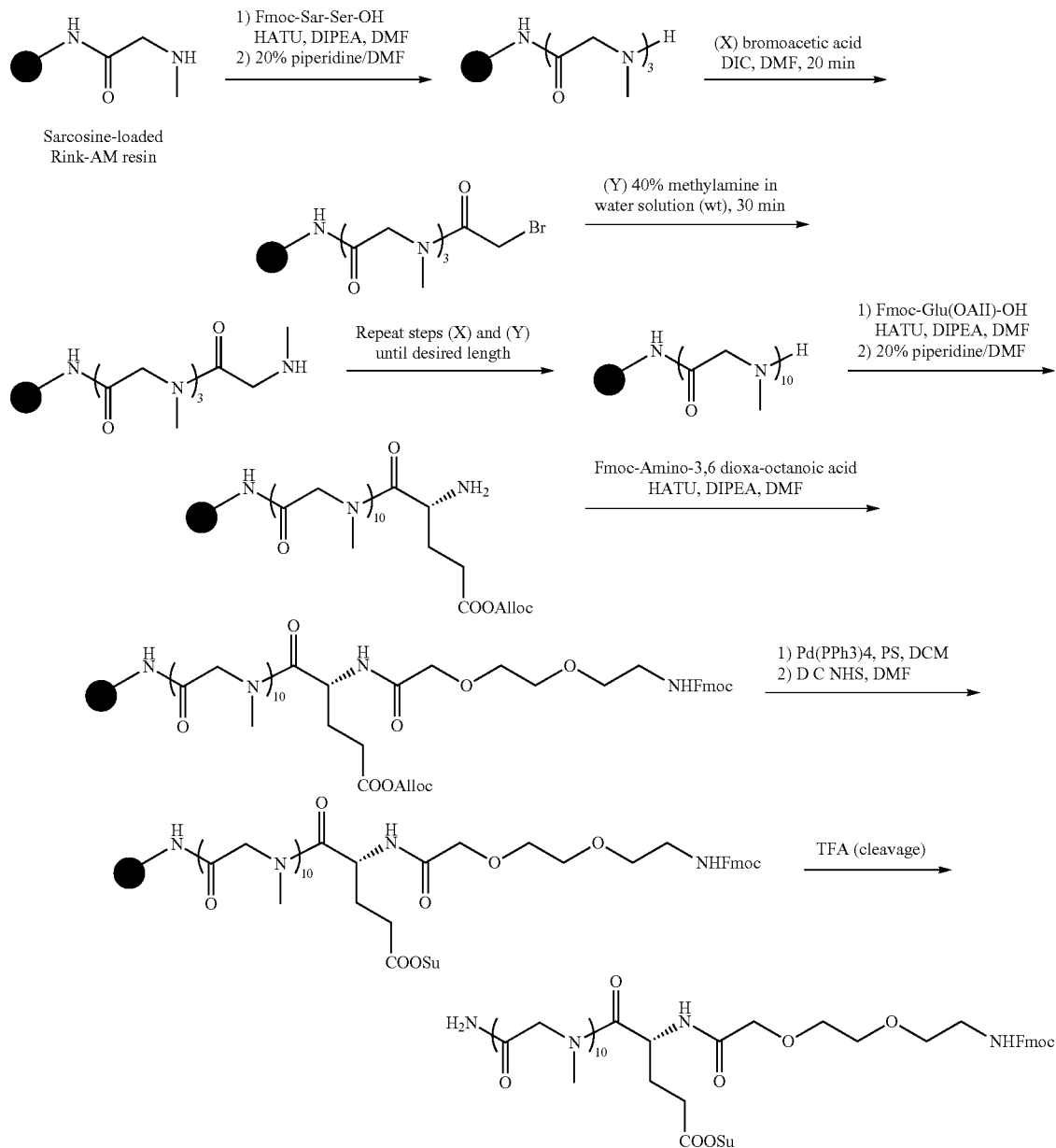

On-resin synthesis of polysarcosines is performed using sub-monomer synthesis iterative procedures for Rink amide with the commercial Fmoc-Sar-Sar-OH dipeptoid building block. Unless otherwise indicated, all reactions are performed at room temperature.

Rink amide preloaded with a first Fmoc-sarcosine residue is used as starting material. Fmoc-sarcosine preloaded Rink amide resin is treated with 20% piperidine in DMF (1 mL per 100 mg of resin) for 2×, 15 min at room temperature. The resin then is washed with DMF (4×) and DCM (4×). To the resin is added a solution of Fmoc-Sar-Sar-OH (3 eq), HATU (2.9 eq) and DIPEA (6 eq) in DMF (1 mL per 100 mg of resin). The reaction vessel is agitated for 2 hours and the resin is washed with DMF (4×) and DCM (4×). The resin is treated with 20% piperidine in DMF (1 mL per 100 mg of resin) for 2 times 15 min, at room temperature. The resin then is washed with DMF (4×) and DCM (4×) to provide a Rink resin having an n=3 polysarcosine oligomer.

Elongation of the n=3 polysarcosine oligomer is performed using sub-monomer synthesis procedures until the desired length is obtained via alternating bromoacetylation and amine displacement steps. The bromoacetylation step is performed by adding 10 eq of bromoacetic acid and 13 eq of diisopropylcarbodiimide in DMF (2 mL per 100 mg of resin). The mixture is agitated for 30 min, drained and washed with DMF (4×). For the amine displacement step, a 40% (wt) methylamine in water solution is added (1.5 mL per 100 mg of resin) and the vessel is shaken for 30 min, drained and washed with DMF (4×) and DCM (4×).

When the desired polysarcosine oligomer length is reached (e.g., a PSAR 10-mer), orthogonal chemical functionalization is performed. Orthogonal chemical functionalization may be followed by a final capping with a Fmoc-protected amino acid group or other group. The Fmoc protecting group may be removed before or after resin cleavage.

The polysarcosine may be functionalized with glutamic acid and Amino-3,6 dioxaoctanoic acid as follows. Fmoc-Glu(OAll)—OH (3 eq), HATU (2.9 eq) and DIPEA (6 eq) in DMF (1 mL per 100 mg of resin) are added to the Rink resin. The reaction vessel is agitated for 90 min and the resin is washed with DMF (4×) and DCM (4×). Resin then is treated with 20% piperidine in DMF (1 ml, per 100 mg of resin) for 2×, 15 min at room temperature. The resin is washed with DMF (4×) and DCM (4×) followed by a 1-hour coupling with Fmoc-Amino-3,6 dioxaoctanoic acid (3 eq), HATU (2.9 eq), DIPEA (6 eq) in DMF (1 mL per 100 mg of resin). The resin is washed with DMF (4×), DCM (4×). The alloc-protecting group is removed by a 2×, 30 min treatment with a DCM solution containing 0.25 eq of Pd(PPh$_3$)$_4$ and 20 eq of phenylsilane (gently agitated under a stream of argon). The resin then is washed with DMF (5×) and DCM (5×). An N-hydroxsuccinimide (NHS) ester is introduced to the carboxylic acid side chain of the final polysarcosine compound by a 90 min treatment with a DMF solution containing 50 eq of DIC and 60 eq of N-hydroxysuccinimide (1.5 mL per 100 mg of resin). The resin then is washed with DMF (4×) and DCM (4×). Final polysarcosine compounds then are cleaved from the resin (100% TFA 2×, 30 min).

4-beta-glucuronide-3-nitro-octopamine intermediate: (2S,3R,4S,5S,6S)-2-(4-(2-((tert-butoxycarbonyl)amino)-1-(((4-nitrophenoxy)carbonyl)oxy)ethyl)-2-nitrophenoxy)-6-(methoxycarbonyl)tetrahydro-2H-pyran-3,4,5-triyl triacetate

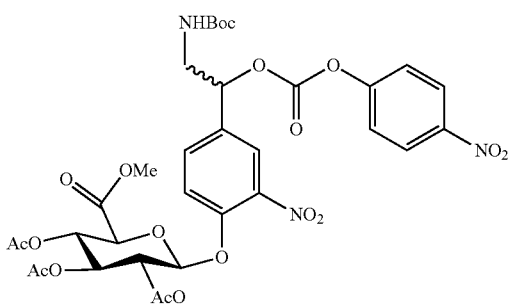

4-beta-glucuronide-3-nitro-octopamine intermediate

The 4-beta-glucuronide-3-nitro-octopamine intermediate 4-beta-glucuronide-3-nitro-octopamine intermediate: (2S,3R,4S,5S,6S)-2-(4-(2-((tert-butoxycarbonyl)amino)-1-(((4-nitrophenoxy)carbonyl)oxy)ethyl)-2-nitrophenoxy)-6-(methoxycarbonyl)tetrahydro-2H-pyran-3,4,5-triyl triacetate may be prepared using Scheme 2.

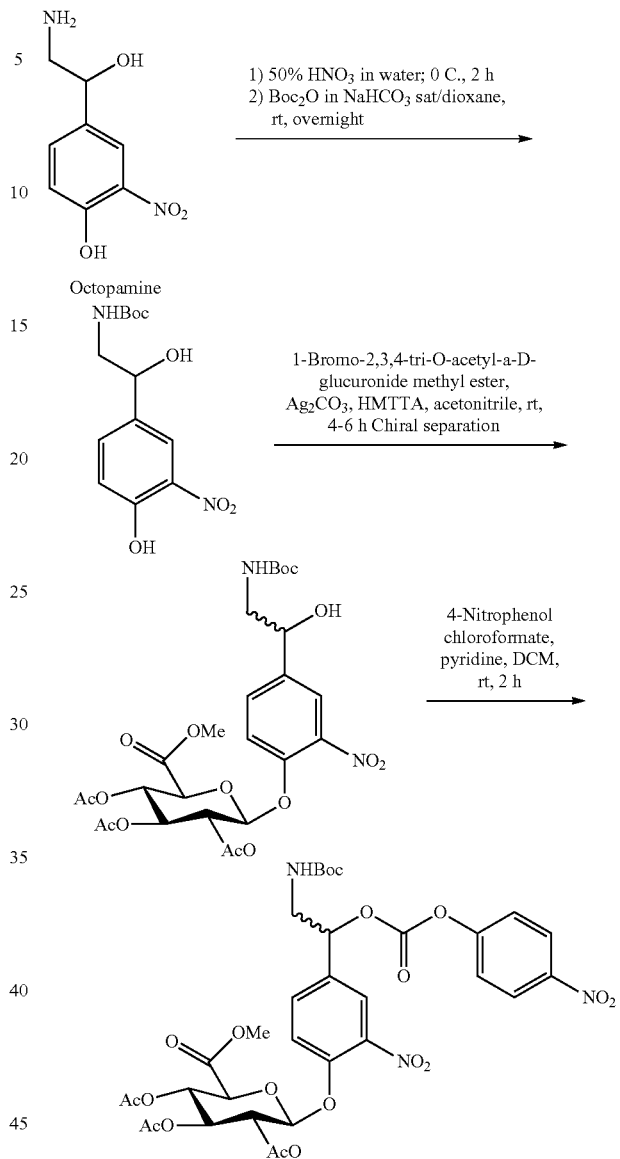

Octopamine or octopamine intermediates as utilized in the present methods may be obtained as racemic mixtures or as enantiopure compounds. Racemic mixtures may be subjected to chiral separation as known in the art to obtain enantiopure compounds.

Octopamine (±) hydrochloride (1690 mg/11 mmol) is suspended in 4 mL of distilled water. The flask is chilled at 0° C. and 4 mL of a pre-chilled 65% nitric acid solution is slowly added. The reaction is kept at 0° C. for 20 minutes and mono-nitration is assessed by HPLC. The mono-nitrated octopamine precursor is transferred to a 250 mL pre-chilled Erlenmeyer and slowly neutralized at 0° C. with a saturated NaHCO$_3$ solution until a pH value of 8-9 is reached. 30 mL of dioxane then is added, followed by Boc$_2$O (7202 mg/13.2 mmol). The reaction is allowed to reach room temperature and is stirred overnight. The reaction then is diluted with EtOAc and washed 3× with a saturated citric acid solution and once with a saturated NaCl solution. The organic phase is dried over MgSO$_4$, filtered, and evaporated under vacuum to afford a crude product that is purified by chromatography on silica gel (petroleum ether/EtOAc, gradient from 70:30 to 20:80) to provide the mono-nitrated octopamine precursor: tert-butyl (2-hydroxy-2-(4-hydroxy-3—nitrophenyl)ethyl) carbamate. The resulting mono-nitrated octopamine precursor then is subjected to chiral separation prior to performing further synthesis steps.

Chiral separation of racemic tert-butyl (2-hydroxy-2-(4-hydroxy-3-nitrophenyl)ethyl)carbamate is performed using an MPLC column and a mobile phase of DCM±0.2% (v/v) EtOH (isocratic gradient) and sample solvent of DCM±0.2% (v/v) EtOH. To determine absolute configuration, phenolic position of both enantiomers is esterified with 1.2 molar equivalents of 4-nitrobenzoyl chloride and 2 molar equivalents of triethylamine in anhydrous THE Compounds are purified by chromatography on silica gel (petroleum ether/EtOAc, gradient from 90:10 to 10:90) to provided 4-(2-((tert-butoxycarbonyl)amino)-1-hydroxyethyl)-2-nitrophenol 4-nitrobenzoate. Absolute configuration of enantiomers (previously dissolved in a 1:1 mixture of heptane/dichloromethane and allowed to slowly evaporate for 3 weeks to induce the formation of crystals) is confirmed by x-ray crystallography.

In a round-bottom flash, Ag$_2$CO$_3$ (1500 mg/5.4 mmol) and 1,1,4,7,10,10-hexamethyltriethylenetetramine (251 mg/1.1 mmol) are suspended in 4 mL of anhydrous acetonitrile and stirred for 2 hours at room temperature. Enantiopure tert-butyl (2-hydroxy-2-(4-hydroxy-3-nitrophenyl) ethyl)carbamate (292 mg/0.98 mmol) and 1-bromo-2,3,4-tri-O-acetyl-a-D-glucuronide methyl ester (583 mg/1.46 mmol) are added at 0° C. and the solution mixture is stirred for 4 h at room temperature. The reaction then is filtered on celite, diluted with EtOAc, and washed 3 times with a saturated citric acid solution and once with a saturated NaCl solution. The organic phase is dried over MgSO$_4$, filtered and evaporated under vacuum to afford a crude product that is purified by chromatography on silica gel (petroleum ether/EtOAc, gradient from 70:30 to 30:70) to provide (2S,3R,4S,5S,6S)-2-(4-(2-((tert-butoxycarbonyl)amino)-1-hydroxyethyl)-2-nitrophenoxy)-6-(methoxycarbonyl)tetrahydro-2H-pyran-3,4,5-triyl triacetate.

(2S,3R,4S,5,6S)-2-(4-(2-((tert-butoxycarbonyl)amino)-1-hydroxyethyl)-2-nitrophenoxy)-6-(methoxycarbonyl)tetrahydro-2H-pyran-3,4,5-triyl triacetate (334 mg/0.54 mmol) and 4-nitrophenyl chloroformate (219 mg/1.09 mmol) are dissolved in 6 mL of dry DCM at 0° C. Anhydrous pyridine (112 mg/1.41 mmol) is added and the mixture is stirred 30 min at room temperature. The reaction is filtered over a 0.45 μm PTFE filter and purified by chromatography on silica gel (petroleum ether/EtOAc, gradient from 85:15 to 30:70) to provide (2S,3R,4S,5S,6S)-2-(4-(2-((tert-butoxycarbonyl)amino)-1-(((4-nitrophenoxy)carbonyl)oxy)ethyl)-2-nitrophenoxy)-6-(methoxycarbonyl)tetrahydro-2H-pyran-3,4,5-triyl triacetate.

4-beta-2glucuronide-3-nitro-octopamine-exatecan intermediate: (2S,3R4S,5S,6S)-2-(4-(2-amino-1-((((1R,9R)-9-ethyl-5-fluoro-9-hydroxy-4-methyl-10,13-dioxo-2,3,9,10,13,15-hexahydro-1H,12H-benzo[de]pyrano[3'A':6,71indolizino[1,2-b]quinolin-1-yl) carbamoyl)oxy)ethyl)-2-nitrophenoxy)-3,4,5-trihydroxytetrahydro-2H-pyran-2-carboxylic acid

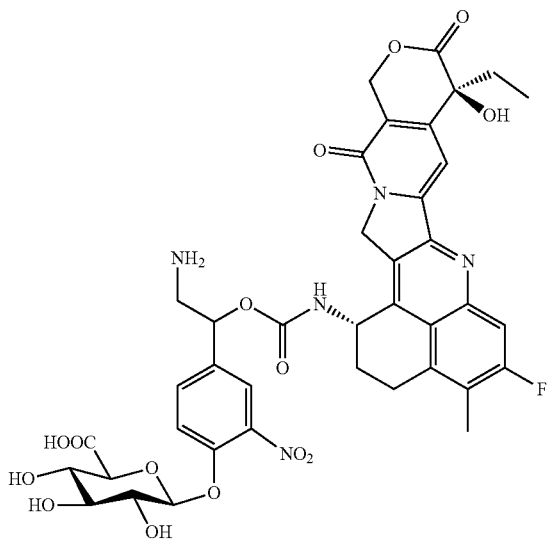

4-beta-glucuronide-3-nitro-octopamine-exatecan intermediate

The 4-beta-glucuronide-3-nitro-octopamine intermediate may be conjugated to exatecan using Scheme 3 to provide the 4-beta-glucuronide-3-nitro-octopamine-exatecan intermediate: (2S,3R,4S,5S,6S)-2-(4-(2-amino-1-((((1R,9R)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)ethyl)-2-nitrophenoxy)-3,4,5-trihydroxytetrahydro-2H-pyran-2-carboxylic acid.

Scheme 3

1) Exatecan Mesylate, HOBt, Pyr DIPEA, DMF, 40 C., 2 H
2) LiOH H$_2$O/ MeOH 0 C., 30 min
3) TFA 30% in DCM
4) Prep-HPLC

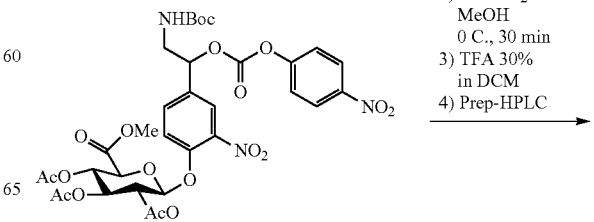

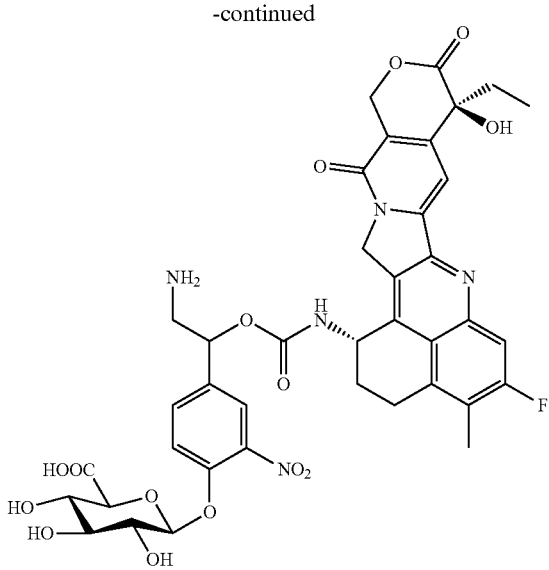

101 mg (0.13 mmol) of 4-beta-glucuronide-3-nitro-octopamine intermediate (2S,3R,4S,5S,6S)-2-(4-(2-((tert-butoxycarbonyl)amino)-1-(((4-nitrophenoxy)carbonyl)oxy)ethyl)-2-nitrophenoxy)-6-(methoxycarbonyl)tetrahydro-2H-pyran-3,4,5-triyl triacetate, 0.14 mmol of Exatecan Mesylate, and 18 rug (0.13 mmol) of HOBt are dissolved in 1 mL of a 85:15 (v/v) mixture of anhydrous DMF/pyridine.

16.7 rug (0.13 mmol) of DIPEA is added. The reaction is stirred for 2 hours at 40° C. and volatiles are evaporated under reduced pressure. The crude residue is purified by chromatography on silica gel (DCM/MeOH gradient from 99:1 to 95:5) to provide an intermediate compound that next is subjected to deprotection.

144 mg (0.106 mmol) of this intermediate compound is dissolved in 3 mL of MeOH (75:25) at 0° C. LiOH monohydrate (44.5 mg/1.06 mmol) is dissolved in water (0.4 mL) and is added to the reaction vessel. After stirring, the mixture is neutralized with acetic acid (83 mg/1.4 mmol) and concentrated under reduced pressure. The obtained crude product is re-dissolved with a TFA/DCM solution and stirred. Volatiles are evaporated under reduced pressure, the crude residue is taken up and purified using HPLC to provide (2S,3R,4S,5S,6S)-2-(4-(2-amino-1-((((1R,9R)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)ethyl)-2-nitrophenoxy)-3,4,5-trihydroxytetrahydro-2H-pyran-2-carboxylic acid.

Conjugation of PSAR intermediate and 4-beta-glucuronide-3-nitro-octopamine-exatecan intermediate to provide functionalized PSAR-4-beta-glucuronide-3-nitro-octopamine-exatecan intermediate

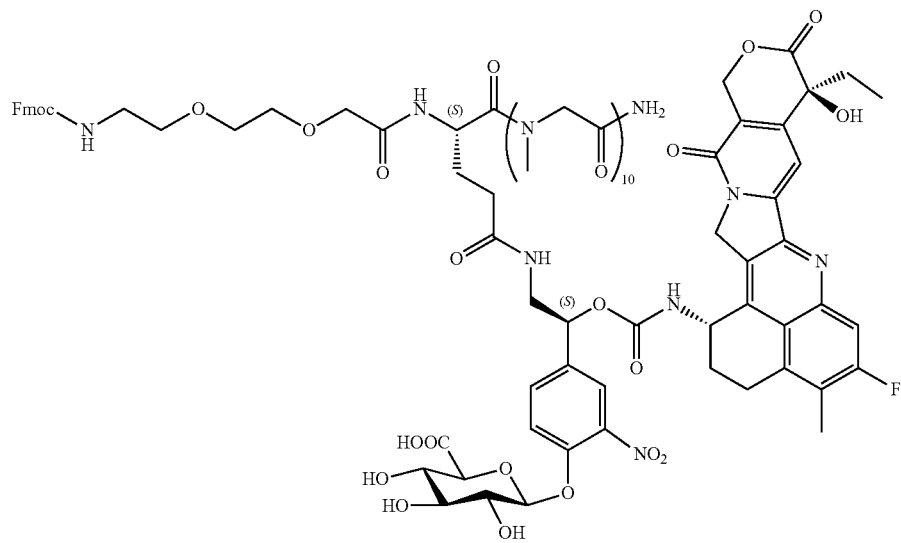

Functionalized PSAR-4-beta-glucuronide-3-nitro-octopamine-exatecan intermediate

The PSAR intermediate and the 4-beta-glucuronide-3-nitro-octopamine-exatecan intermediate may be conjugated using Scheme 4 to provide the functionalized PSAR-4-beta-glucuronide-3-nitro-octopamine-exatecan intermediate.

reaction is stirred 30 min at room temperature. After entire conversion of the reaction is assessed by HPLC, piperidine is directly added into the reaction vial in order to reach an 8% (v/v) piperidine solution in DMF. The reaction is then stirred at room temperature 5-10 min, until entire Fmoc-deprotection is observed by HPLC. The reaction is slowly Scheme 4

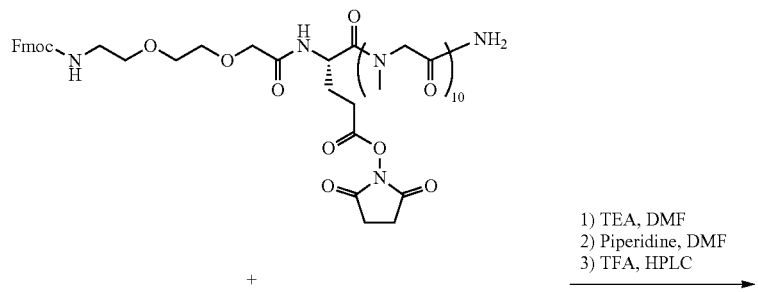

1) TEA, DMF
2) Piperidine, DMF
3) TFA, HPLC

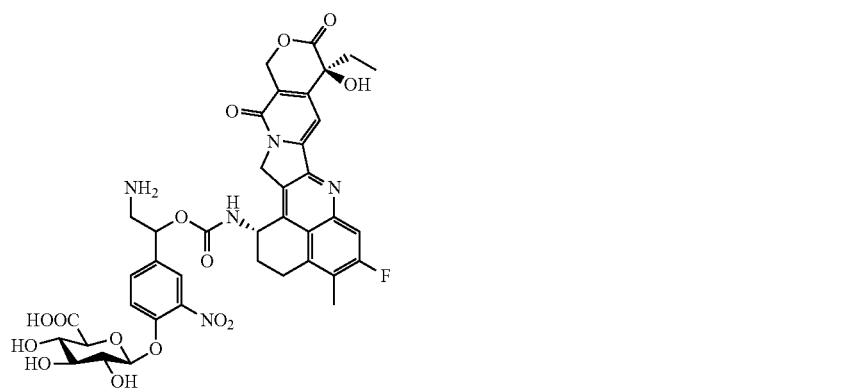

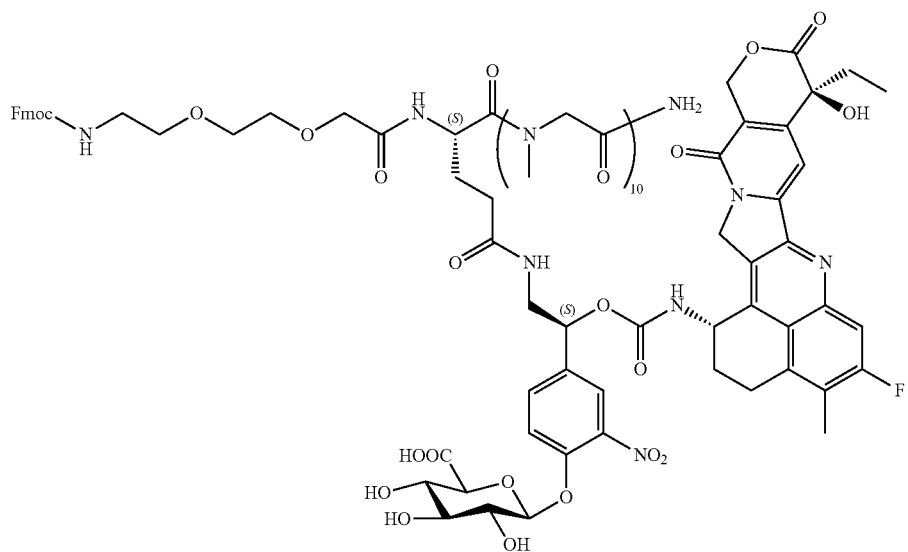

100 mg (0.081 mmol) of the PSAR intermediate and 51 mg (0.061 mmol) of the 4-beta-glucuronide-3-nitro-octopamine-exatecan intermediate are dissolved in anhydrous DMF. 41 mg (0.405 mmol) of triethylamine is added and the reaction is neutralized with a 10% TFA solution in water/ACN 1:1 (v/v) and purified using HPLC to provide the functionalized-PSAR-4-beta-glucuronide-3-nitro-octopamine-exatecan intermediate.

Linker-Payload of Formula (L-P'): (2S,3',4S,51?, 6S)-6-(4-((3S,9S)-40-amino-9-(22-(2-(3-(2.5-dioxo-2,5-dihydro-1H-1-pyrrol-1-yl)propanamido)ethoxy)ethoxy)acetamido)-1-(((1S,9%)-9-ethyl-5-fluoro-9-hydroxy-4-methyl-10,13-dioxo-2,3,9,10,13,5-hexahydro-1-12H-benzo[de]pyrano[3', 6':6,7]indolizinol[1,2-b]quinolin-1-yl)amino)-11,14,17,20,23,26,29,32,35,38-decamethyl-1,6,10,13,16,19,22,25,28,31,34,37,40-tridecaoxo-2-oxa-5,11,14,17,20,23,26,29,32,35,38-undecaazatetracontan-3-yl)-2-nitrophenoxy)-3,4,5-trihydroxytetrahydro-2H-pyran-2-carboxylic acid

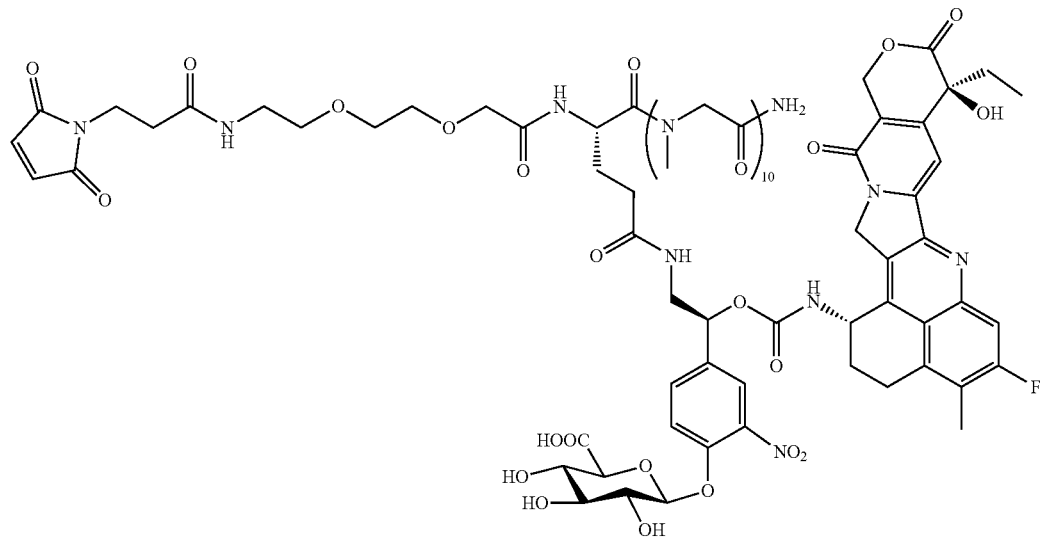

Linker-Payload of Formula (L-P')

The Linker-Payload of Formula (L-P') may be prepared by conjugating maleimidopropionic acid N-hydroxysuccinimide ester and the functionalized-PSAR-4-beta-glucuronide-3-nitro-octopamine-exatecan intermediate using Scheme 5.

Scheme 5

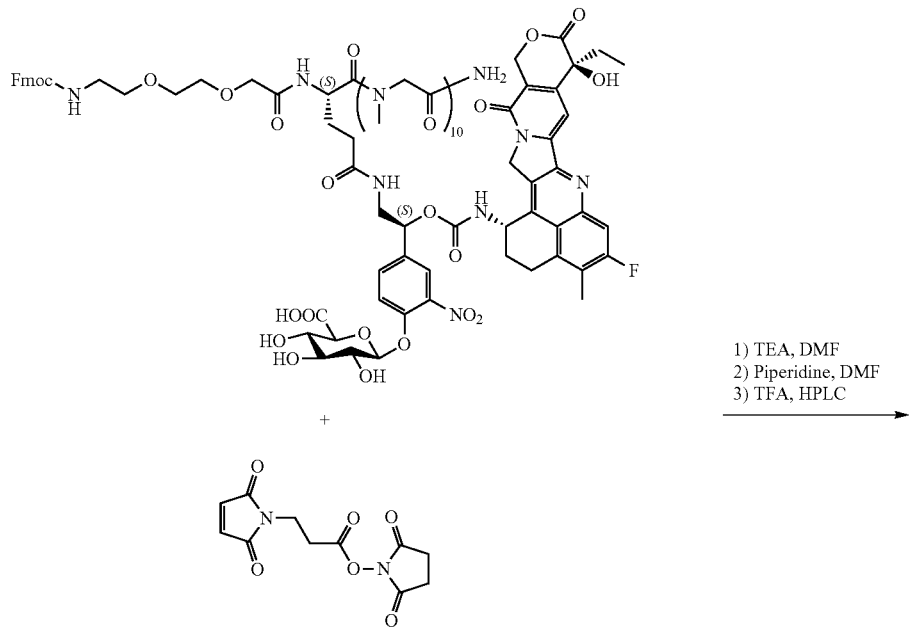

1) TEA, DMF
2) Piperidine, DMF
3) TFA, HPLC

-continued

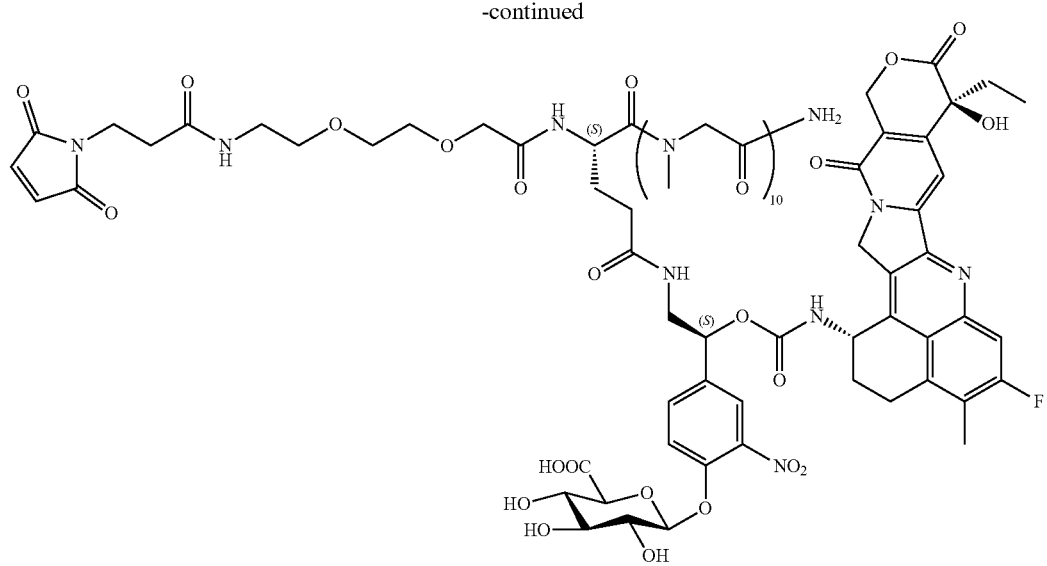

Maleimidopropionic acid N-hydroxsuccinimide ester and functionalized-PSAR-4-beta-glucuronide-3-nitro-octopamine-exatecan intermediate are dissolved in anhydrous DMF (0.1M concentration of maleimide compound). 1.56 mg (0.015) of triethylamine was added and the reaction was stirred for 2 hours until entire conversion of the reaction as observed by HPLC. The reaction mixture is then diluted with a 1% TFA solution in water/ACN 1:1 (v/v) and purified using HPLC preparative method 6 to provide Linker-Payload of Formula (L-P').

Example 2: Humanized Anti-Nectin 4 Monoclonal Antibody (15A7.5 mAb)

The anti-Nectin-4 mAb utilized for the disclosed ADCs is a humanized derivative of the mAb 15A7.5, described in WO2022/207822 and WO2022/207825. As indicated, the mAb 15A7.5 exhibits selective affinity for tumor cells versus keratinocytes. The mAb utilized to prepare the ETx-22 ADC disclosed herein is a humanized derivative of the 15A7.5 mAb having back mutations introduced into the amino acid sequence of its HC (H1) and the amino acid sequence of its LC (L2), and is referred to herein as H1L2_15A7.5. The H1L2_15A7.5 mAb has a heavy chain amino acid sequence of SEQ ID NO:5 and a light chain amino acid sequence of SEQ ID NO:6. The HC variable region (HCVR) is provided as SEQ ID NO:7 and the LC variable region (LCVR) is provided as SEQ ID NO:8. The HC and LC complementary determining regions (HCDRs and LCDRs) are provided as SEQ ID Nos: 9-14 (Kabat) and SEQ ID Nos: 15-20 (IMGT).

Example 3: Preparation of ETx-22 ADC

The ADC referred to as "ETx-22" was prepared by conjugating the H1L2-15A7.5 mAb via cysteine residues to an exatecan payload referred to herein as the Linker-Payload of Formula (L-P'). A schematic representation of ETx-22 is provided in FIG. 1.

To prepare the ADC referred to as ETx-22, the mAb H1L2-15A7.5 (HC: SEQ ID NO:5; LC: SEQ ID NO:6) in PBS 1x, 1 mM EDTA was reduced with 14 molar equivalent of TCEP for 2 hours at 37° C., after which the buffer was exchanged (Amicon ultra 30 kDa) to 100 mM KPO$_4$, 1 mM EDTA pH 7.4. Twelve molar equivalents of the Linke-Payload of Formula (L-P') were used for conjugation with the reduced mAb for 35 min at room temperature. Buffer was then exchanged to 100 mM KPO$_4$ pH 8.0, before incubation at 37° C. for 24 hours in absence of oxygen to allow the maleimide to self-hydrolyze. The final exchange buffer was performed in 20 mM His pH 6.0 before filtration 0.22 µM filter to provide ETx-22.

Figure 2:
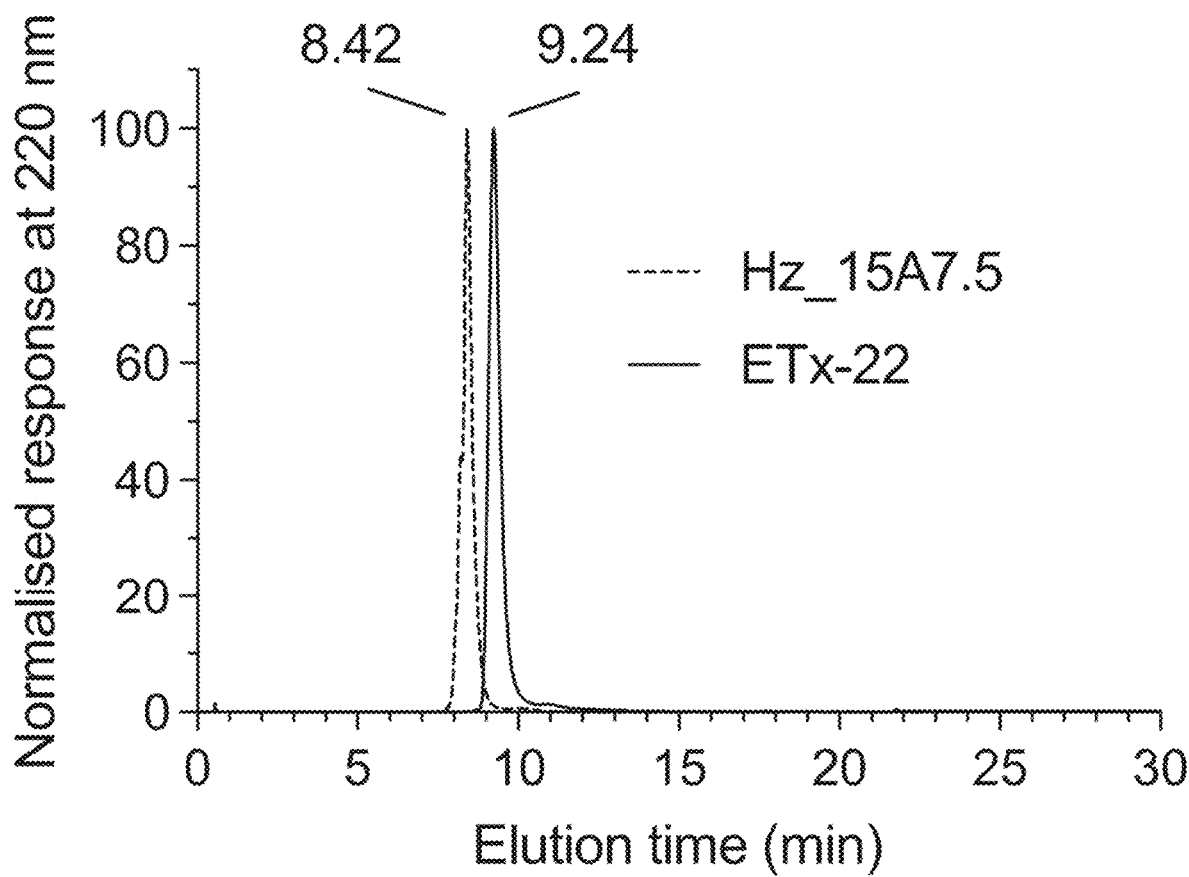
FIG. 2. Comparative HIC between the naked humanized 15A7.5 and ETx-22.
Figure 4:
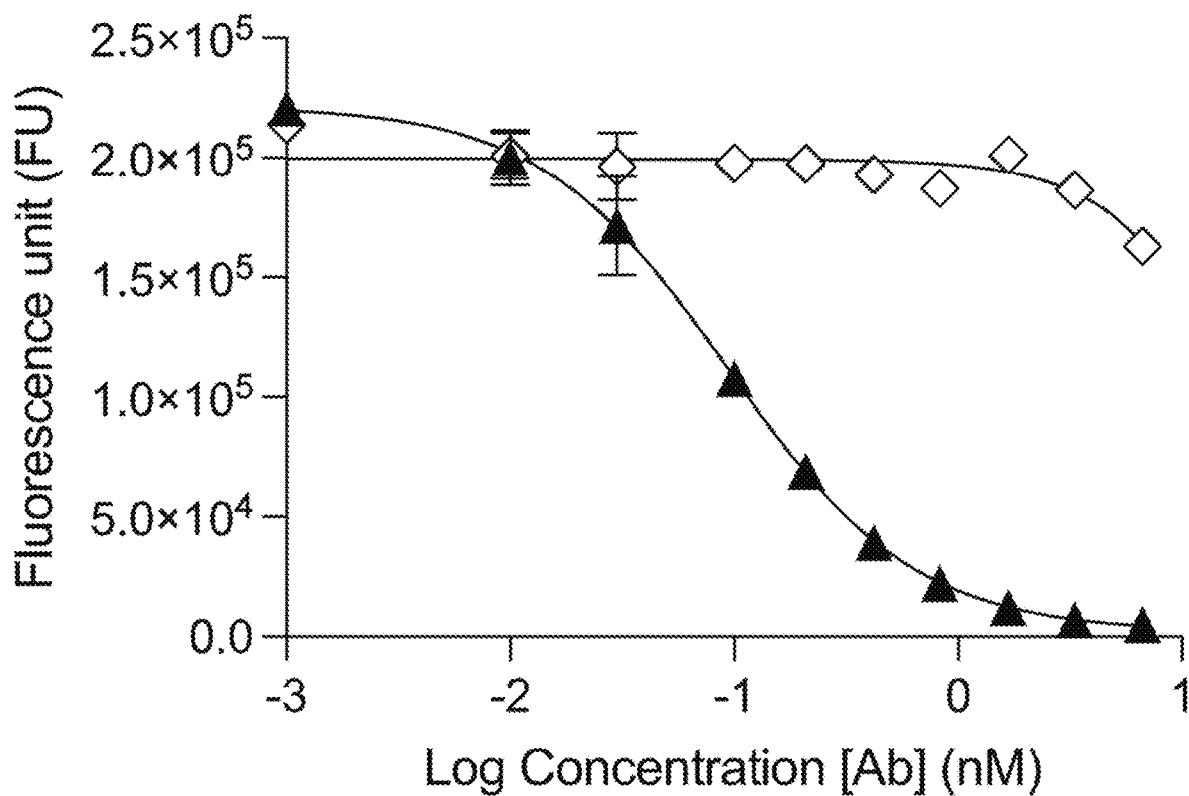
FIG. 4. ETx-22 in vitro cytotoxic activity. A dose range of ETx-22 (solid triangles) or an IgG1 isotype control coupled to the same linker payload (open diamonds) were incubated with HCT-116-2G10 clone expressing human nectin-4 for 8 days. Viability was monitored through mitochondrial oxidation (cell titer blue reagent) with BMG Labtech fluorometer.

The drug-antibody ratio (DAR) for ETx-22 was determined according to LC-MS analysis and was found to be between 7.77 and 7.82 toxins per conjugated mAb. As determined by SEC-HPLC, less than 5% material was aggregated. Analysis of ETx-22 by hydrophobic interaction chromatography (HIC) revealed a single and sharped peak for ETx-22 close to naked 15A7.5 mAb which indicates a high homogenous hydrophilicity. (See FIG. 2 and corresponding Brief Description). Ex vivo stability of ETx-22 was assessed by incubating ETx-22 in mouse, cynomolgus or human serum and measuring DAR over time. (See FIG. 3 and corresponding Brief Description). In vitro cytotoxic activity was assessed for the HCT-116-2G10 clone expressing human nectin-4. (See FIG. 4 and corresponding Brief Description).

As a comparator ADC, the HA22 anti-Nectin-4 mAb was conjugated to maleimidocaproyl-valine-citrulline-PABC-MMAE to generate enfortumab vedotin. Briefly, a 15 mg/mL solution of the HA22 in 10 mM acetate 1% sorbitol, 3% L-arginine, pH 5.0 was supplemented with a 20% volume of 0.1 M Tris, 25 mM EDTA and 750 mM NaCl, pH 8.4 to adjust the pH of the solution to 7.5, 5 mM EDTA and 150 mM sodium chloride. HA22 mAb was then partially reduced by adding 2.5 molar equivalents of TCEP and then gently stirred at 37° C. for 2 hours. The partially reduced mAb solution was then cooled to 5° C. and 4.4 molar equivalents of cysteine reactive linker-exatecan compound added as a 6% (v/v) solution of DMSO. The mixture was stirred for 60 minutes at 5° C., then for 15 additional minutes following the addition of 1 molar equivalents of N-acetyl-cysteine relative to cysteine reactive linker-MMAE compound. Excess quenched cysteine reactive linker-payload and other reaction components were removed by ultrafiltration/diafiltration of the antibody drug conjugate (ADC) with 10 volumes of 20 mM histidine, pH 6.0. The drug-antibody ratio (DAR) according to LC-MS analysis was 3.79 toxins per conjugated mAb. As determined by SEC-HPLC, less than 1% material was aggregated.

Example 4: In Vivo Studies in Mice

Female NOD/SCID/γc null (NSG) and male NMRI-nude mice were obtained from Charles River laboratories. Female NOD/SCID and BALB/c nude mice were obtained from GemPharmatech Co. Mice were housed under sterile conditions with sterilized food and water provided ad libitum and maintained on a 12-h light and 12-h dark cycle. For NSG mice, cells and PDX were inoculated in both flanks in the mammary fat pads with $0.5 \times 10^6$ cells suspended in 50% phenol red-free Matrigel (Becton-Dickinson Bioscience). Otherwise, PDX fragments (2-3 mm. in diameter) were inoculated subcutaneously.

Mice were treated when tumor reached average volume of 100-200 mm$^3$. Mice were treated i.v. with a single or 2 doses of ADCs at indicated concentrations. Tumor growth was monitored by measuring with a digital caliper and by calculating the tumor volume (length×width$^2$×π/6). All animals were randomly assigned into treatment groups, such that the mean tumor volume for each group was 100 to 200 mm$^3$. Animal weight was monitored every 3 days in order to evaluate the toxicity of the different treatments. Mouse weight loss>20%, tumor volume>1500 mm$^3$, ruffled coat and hunched back, weakness, and reduced motility were monitored and considered as endpoints.

Figure 5:
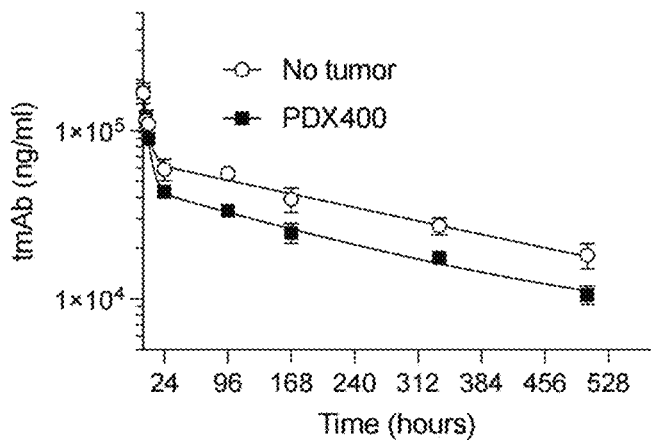
FIG. 5. PK/PD characterization of ETx-22 ADC. NSG mice and TNBC PDX400-grafted NSG mice (n=3 per time point) were injected intravenously when tumors averaged 150 mm$^3$ (TO) with 10 mg/kg of ETx-22. At the indicated time points, terminal blood sampling was performed, and plasma was prepared from naive and PDX 400-grafted NSG mice. A, pharmacokinetic analysis of ETx-22 (ADC+total antibody) by mesoscale discovery technique. B, in vivo stability measurement by LC/MS after affinity capture of ETx-22 with anti-human LC-kappa. C, determination by LC/MS of circulating free exatecan concentration in plasma.
Figure 5:
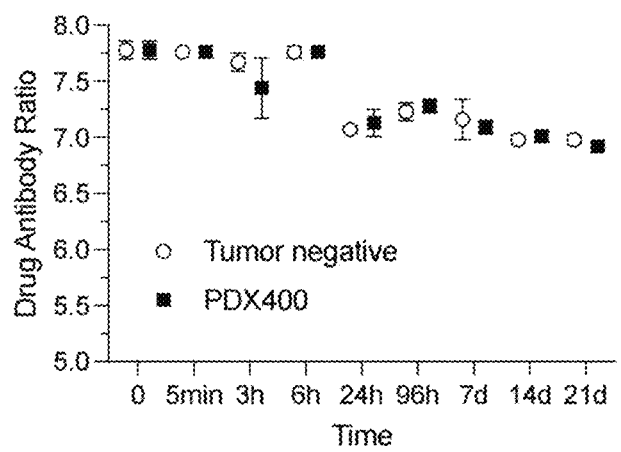
Figure 5:
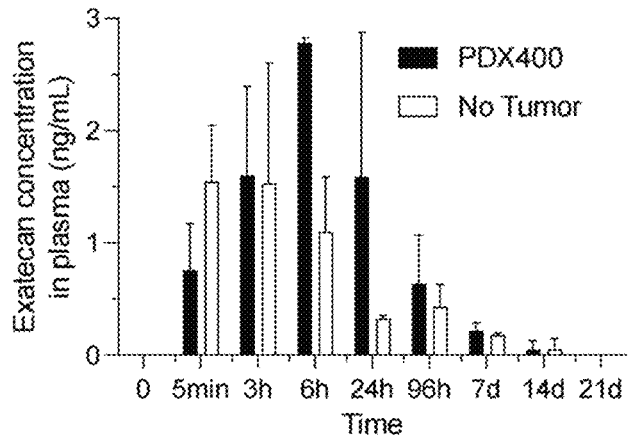

PK/PD characterization of ETx-22 was assessed using NSG mice and triple negative breast cancer (TNBC) PDX400-grafted NSG mice. (See FIG. 5 and corresponding Brief Description).

Figure 6:
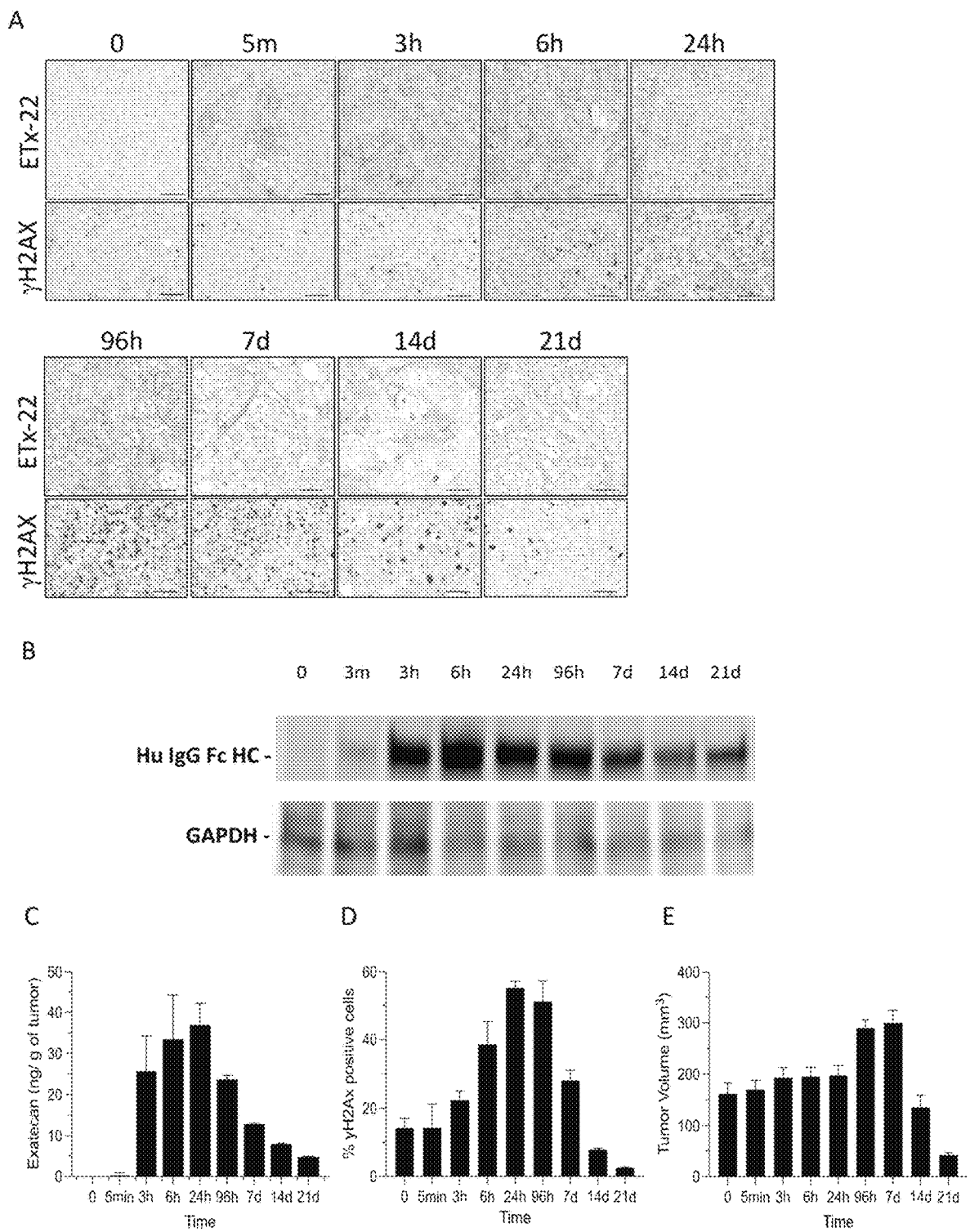
FIG. 6. ETx-22 mechanism of action. TNBC PDX400-grafted NSG mice (n=3 per time point) were injected intravenously when tumors averaged 150 mm$^3$ (TO) with 10 mg/kg of ETx-22. At the indicated time points, animals were euthanized, and their tumors were collected, measured, and weighted. A, IHC analysis of ETx-22 infiltration and pharmacodynamics in PDX400 tumors. Tumors were fixed and embedded in paraffin. ETx-22 (upper panels) was detected with rabbit anti-human IgG which was revealed with a secondary anti-rabbit IgG coupled to horseradish peroxidase and ChromoMap DAB kit. Phosphorylated H2A.X (lower panels) which is a marker of topoisomerase I inhibitor activity, was detected with mouse anti-phospho-Histone H2A.X which was revealed with a secondary rabbit anti-mouse IgG and a tertiary anti-rabbit IgG coupled to horseradish peroxidase and ChromoMap DAB kit. B, western blot analysis of tumor lysates. ETx-22 was detected with a goat anti-human IgG conjugated to horseradish peroxidase. C, LC/MS determination of exatecan amount per gram of tumor. D, quantification of phosphorylated H2A.X positive cells. Slides in A were numerized with Hamamatsu scanner and Tribun Calopix software was used to quantify the percentage of phosphorylated H2A.X positive cells. E, tumor volume measured with a caliper ($V=(L \times W \times H) \times \pi/6$)).

The mechanism of action for ETx-22 was assessed in NSG mice grafted with a PDX model for triple negative breast cancer (PDX400). (See FIG. 6 and corresponding Brief Description).

Figure 7:
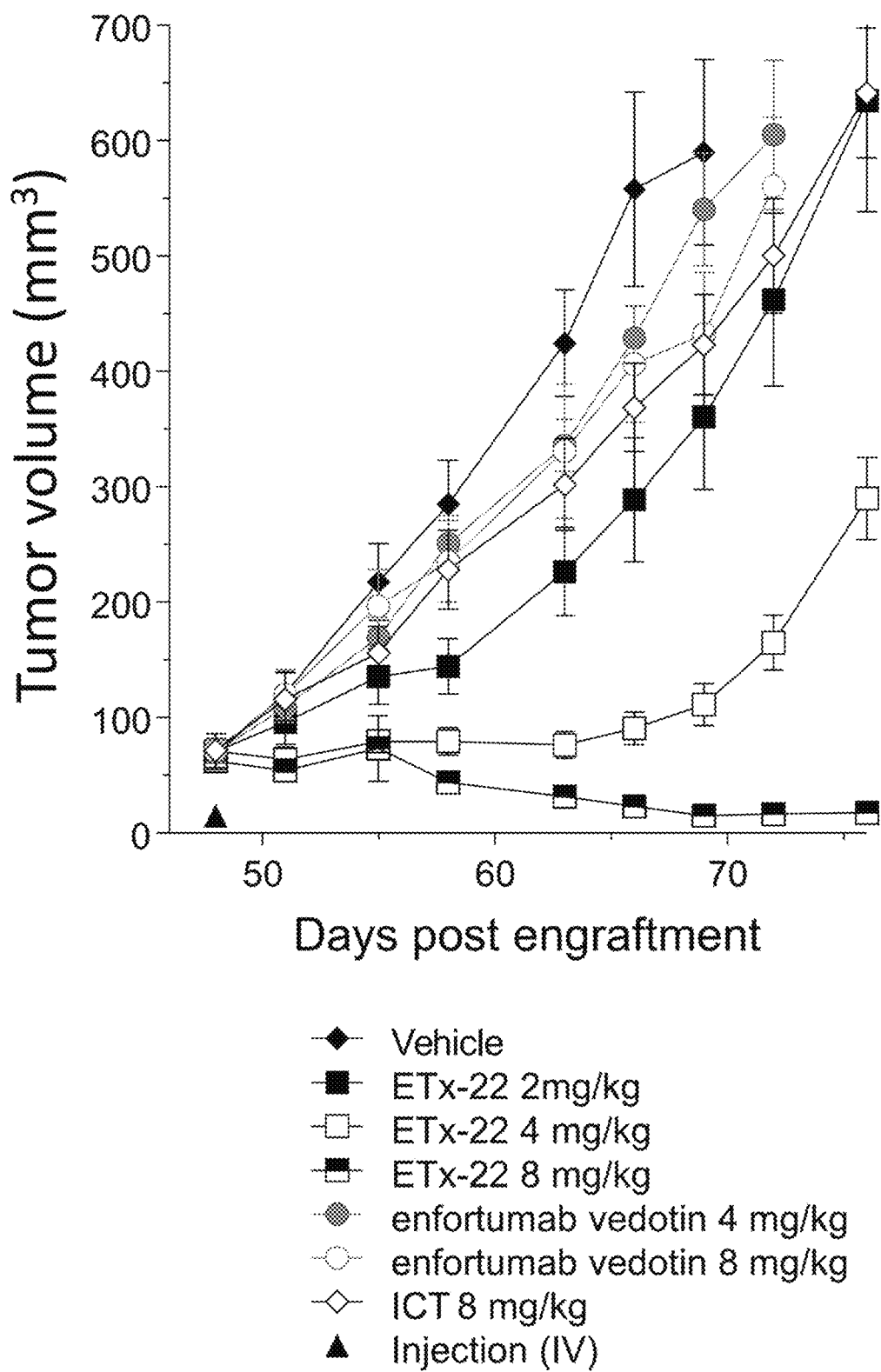
FIG. 7. In vivo efficacy of ETx-22 in MMAE resistant TNBC cell line (SUM190). NSG mice (n=5/group) were orthotopically xenografted bilaterally with MMAE resistant SUM190 cells embedded in Matrigel. At the indicated time (black arrowhead), 3 different ADCs were injected intravenously: Isotype control (8 mg/kg), ETx-22 at 2, 4 and 8 mg/kg and enfortumab vedotin at 4 and 8 mg/kg. Control group received ADC diluent. Tumor growth was monitored twice a week (V (mm$^3$)=L×W$^2$×π/6).

The in vivo efficacy of ETx-22 in the MMAE resistant triple negative breast cancer (TNBC) cell line (SUM190) was assessed in NSG mice. (See FIG. 7 and corresponding Brief Description).

Figure 8:
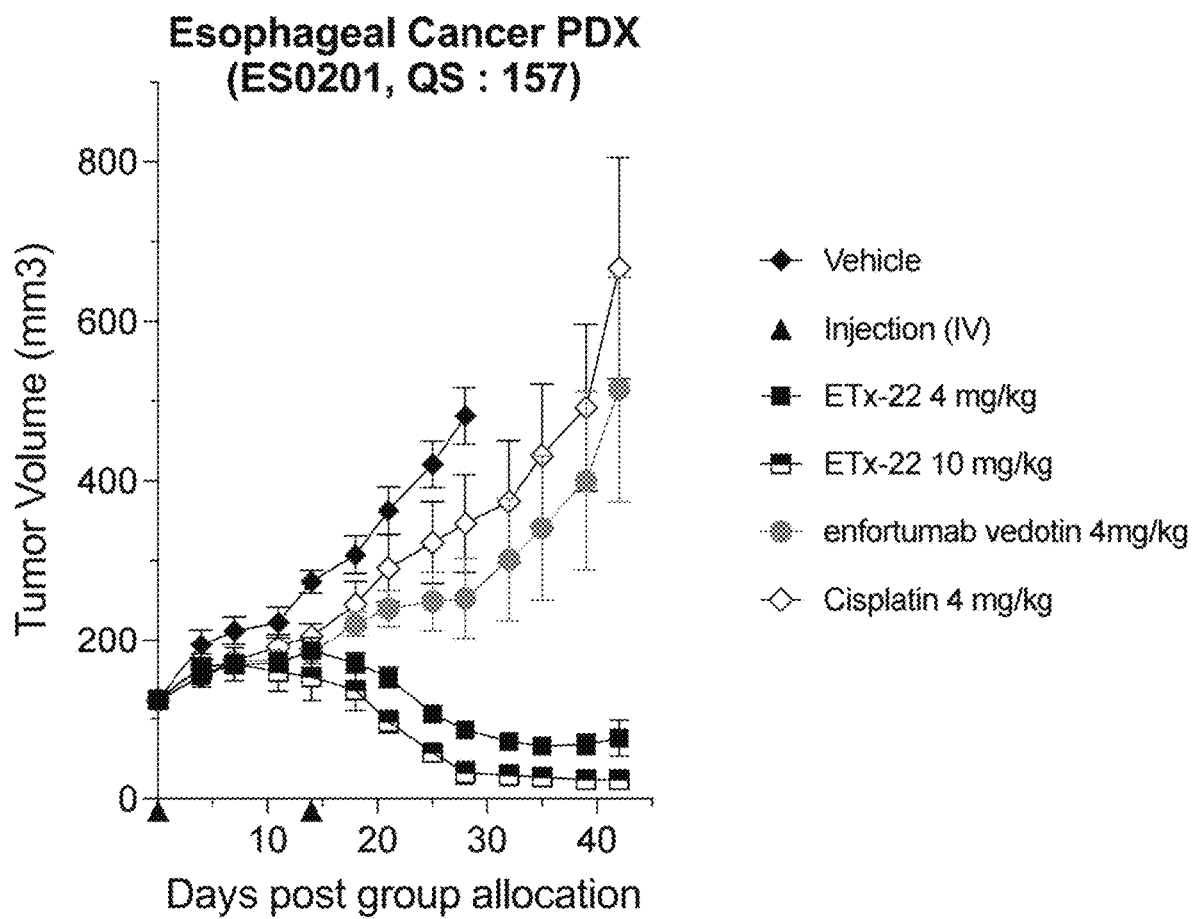
FIG. 8. In vivo efficacy of ETx-22 in PDX model (ES0201, esophageal cancer). BALB/c Nu mice were subcutaneously implanted with tumor fragments. At the indicated time (black arrowhead), the indicated ADCs were injected twice intravenously. Quick score for nectin-4 expression was determined by immuno-histochemistry. Tumor growth was monitored twice a week (V (mm$^3$)=L×W$^2$×π/6).
Figure 9:
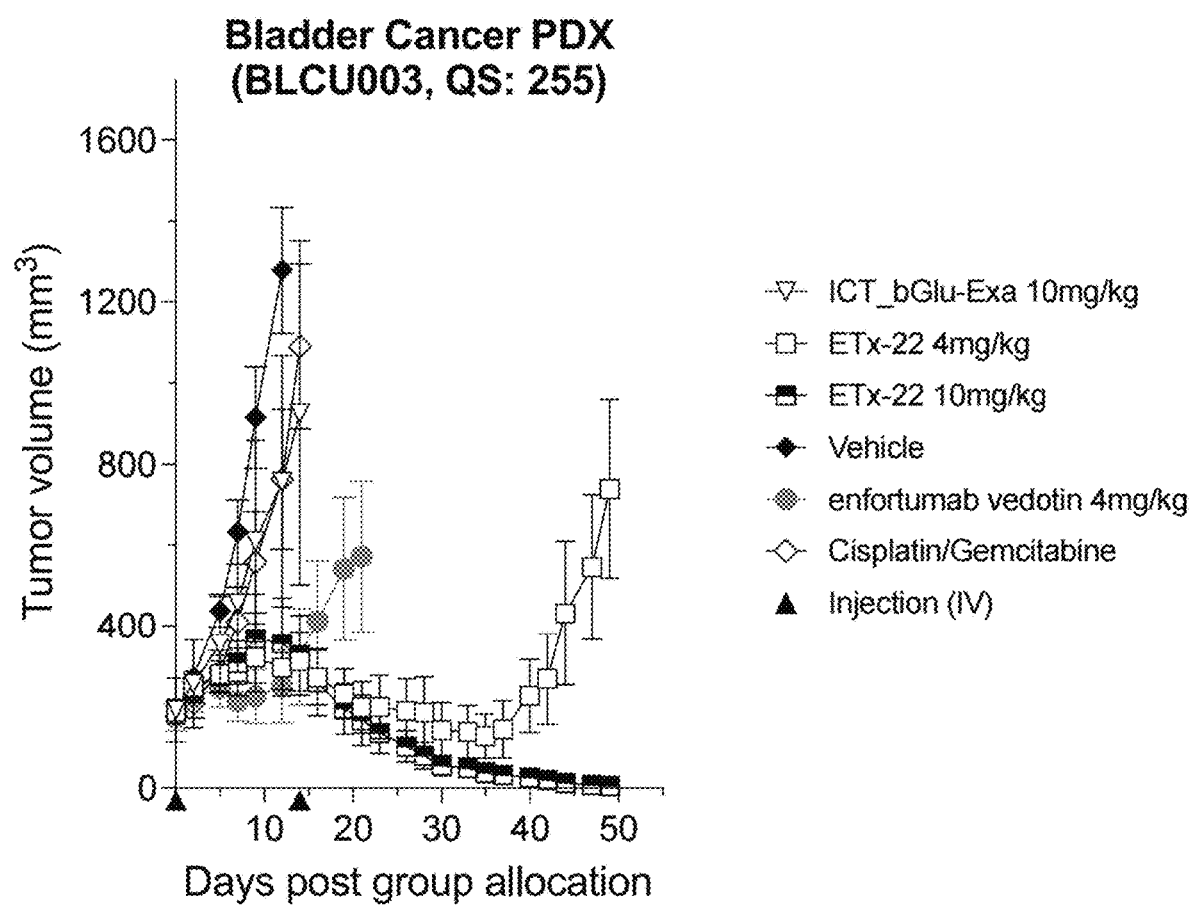
FIG. 9. In vivo efficacy of ETx-22 in PDX model (BLCU003, bladder cancer). NMRI nude mice were subcutaneously implanted with tumor fragments. At the indicated time (black arrowhead), the indicated ADCs were injected twice intravenously. Quick score for nectin-4 expression was determined by immuno-histochemistry staining and is shown here. Tumor growth was monitored twice a week (V (mm$^3$)=L×W$^2$×π/6).
Figure 10:
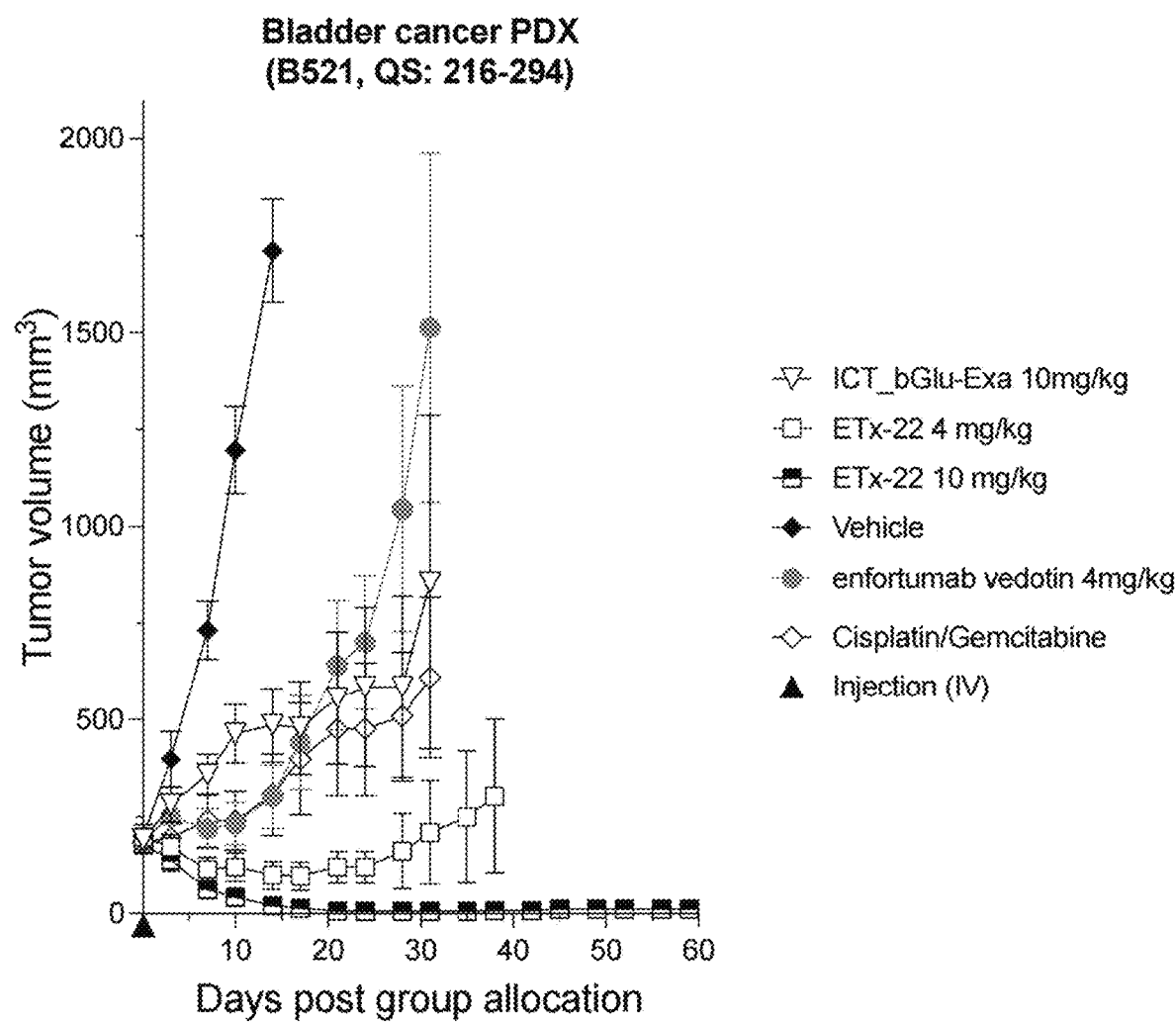
FIG. 10. In vivo efficacy of ETx-22 in PDX model (B521, bladder cancer). The bladder cancer PDX model B521 exhibits relatively high Nectin-4 expression and has a homozygous mutation in FGFR3 imparting resistance to erdafitinib. Cisplatin/gemcitabine were administered: 4 mg/kg Q3W×2/60 mg/kg QW×4.
Figure 11:
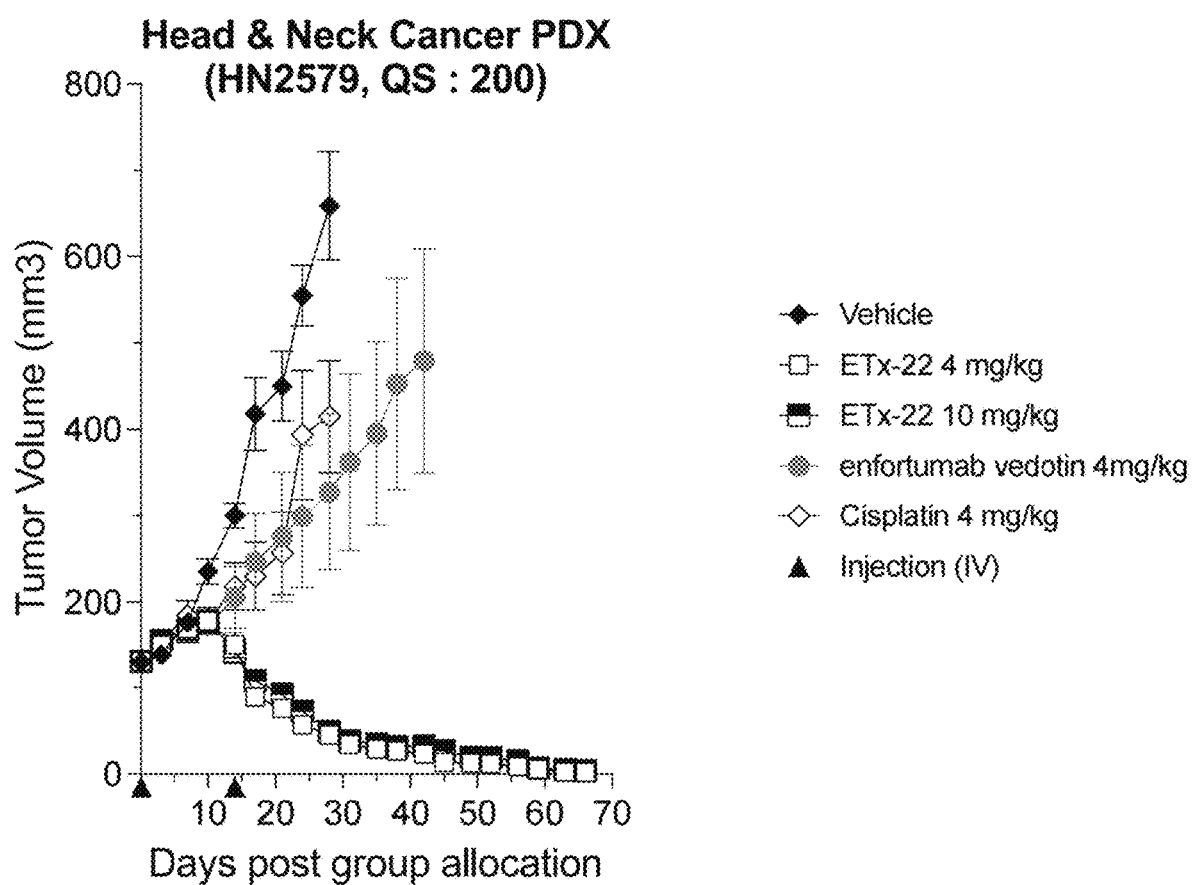
FIG. 11. In vivo efficacy of ETx-22 in PDX model (HN2579, head & neck cancer). The head & neck PDX model HN2579 exhibits moderate to high Nectin-4 expression. NOD/SCID mice were subcutaneously implanted with tumor fragments. At the indicated time (black arrowhead), the indicated ADCs were injected twice intravenously. Quick score for nectin-4 expression was determined by immuno-histochemistry staining and is shown here. Tumor growth was monitored twice a week (V (mm$^3$)=L×W$^2$×π/6), FIG. 12. In vivo efficacy of ETx-22 in PDX model (CV3035, cervical cancer). BALB/c Nu mice were subcutaneously implanted with tumor fragments. At the indicated time (black arrowhead), the indicated ADCs were injected twice intravenously. Quick score for nectin-4 expression was determined by immuno-histochemistry staining and is shown here. Tumor growth was monitored twice a week (V (mm$^3$)=L×W$^2$×π/6).
Figure 12:
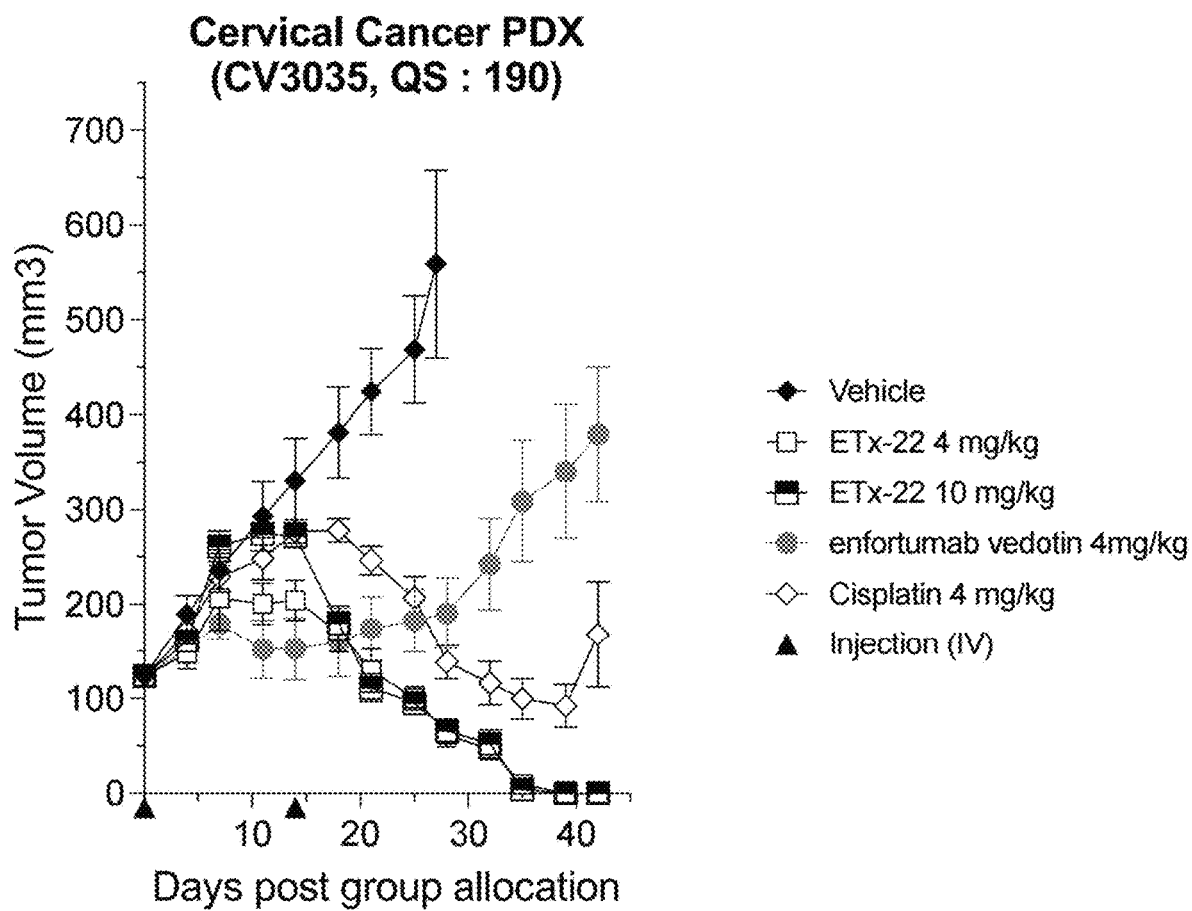
Figure 13:
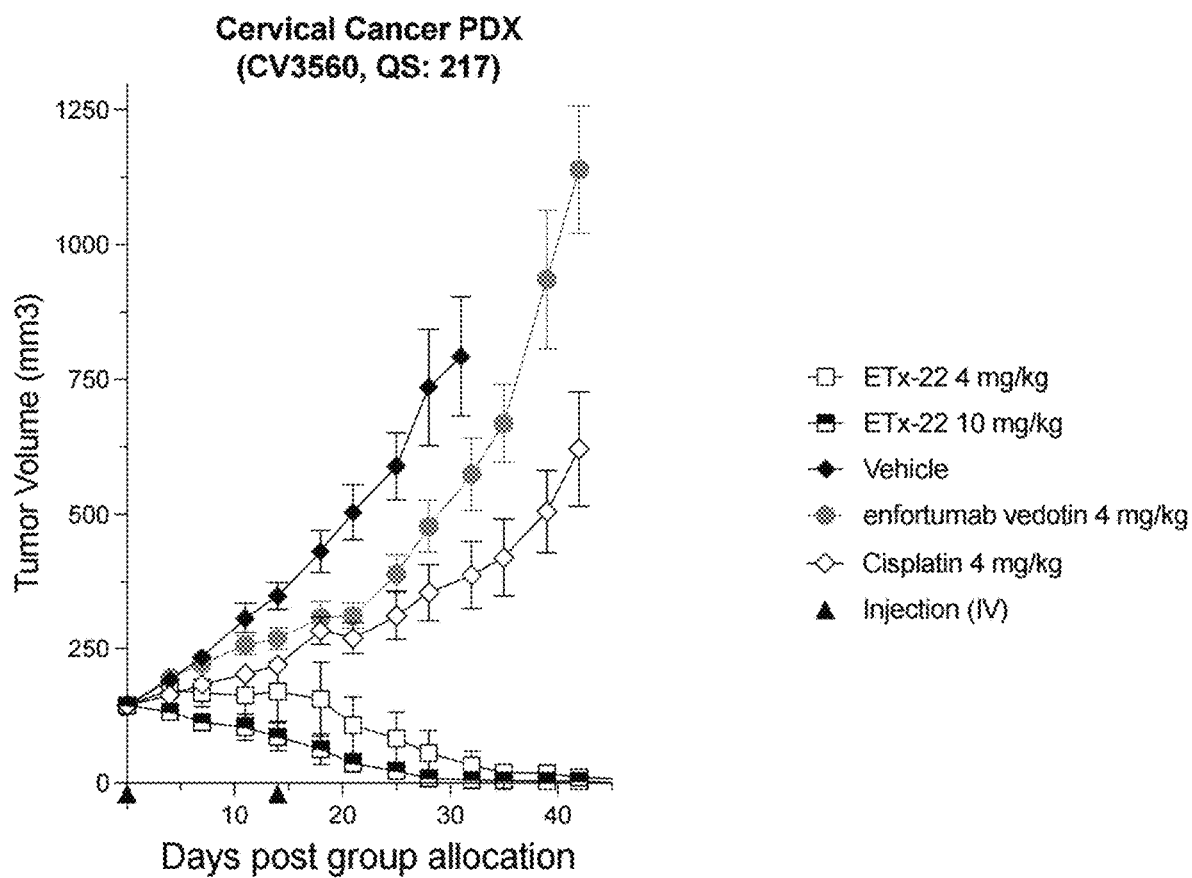
FIG. 13. In vivo efficacy of ETx-22 in PDX model (CV3560, cervical cancer). The cervical cancer PDX model CV3560 exhibits moderate to high Nectin-4 expression.
Figure 14:
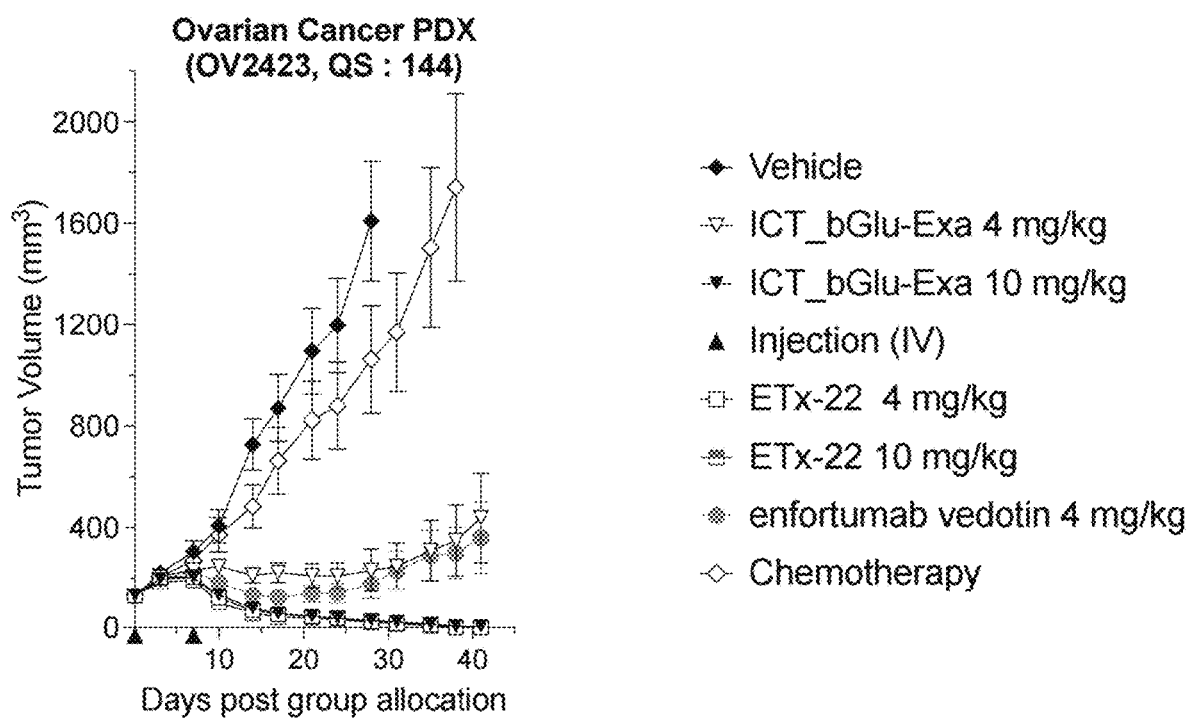
FIG. 14. In vivo efficacy of ETx-22 in PDX model (OV2423, ovarian cancer). NOD/SCID mice were subcutaneously implanted with tumor fragments. At the indicated time (black arrowhead), the indicated ADCs were injected twice intravenously. In each PDX model, the quick score for nectin-4 expression was determined by immuno-histochemistry staining and is shown here. Tumor growth was monitored twice a week (V (mm$^3$)=L×W$^2$×π/6).

The in vivo efficacy of ETx-22 was assessed in PDX models for esophageal cancer (ES0201) (FIG. 8 and corresponding Brief Description); bladder cancer (BLCU003) (FIG. 9 and corresponding Brief Description); bladder cancer (B521) (FIG. 10 and corresponding Brief Description); head & neck cancer (HN2579) (FIG. 11 and corresponding Brief Description); cervical cancer (CV3035) (FIG. 12 and corresponding Brief Description); cervical cancer (CV3560) (FIG. 13 and corresponding Brief Description); and ovarian cancer (OV2423) (FIG. 14 and corresponding Brief Description).

Figure 15:
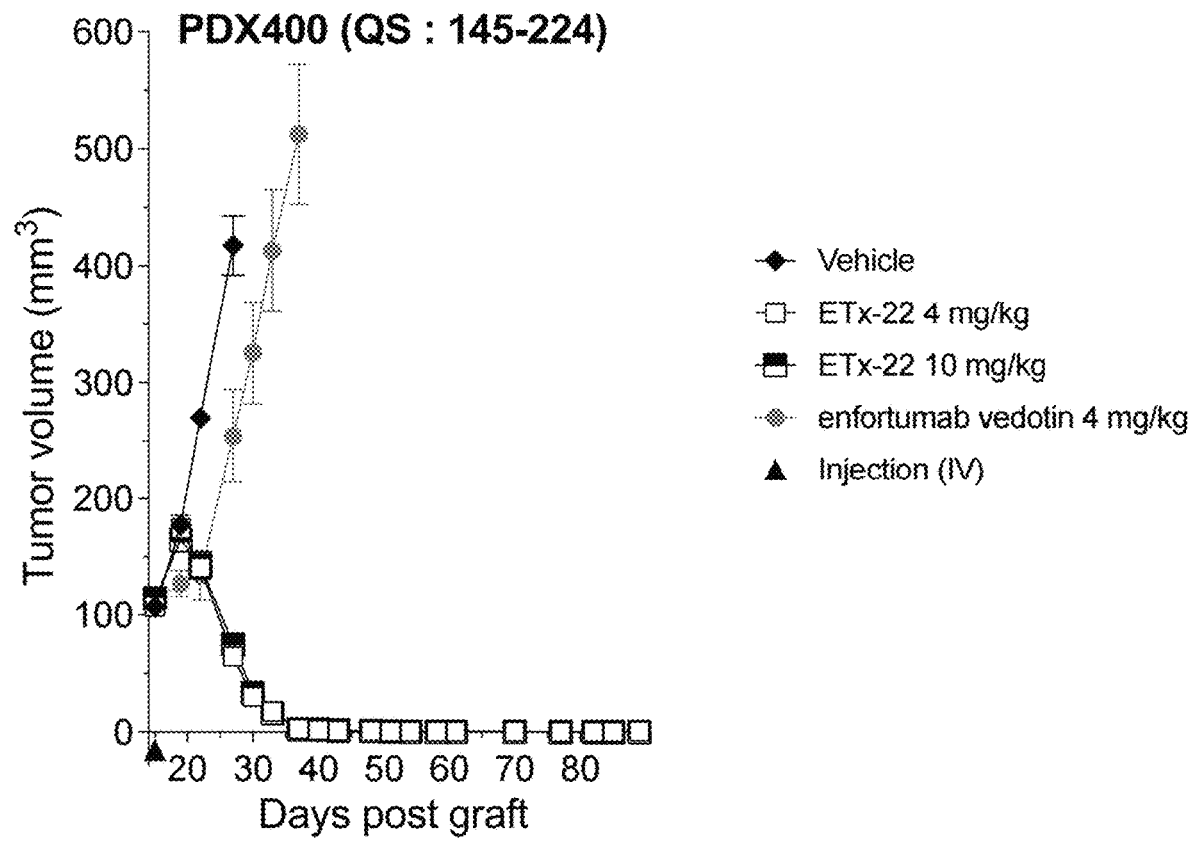
FIG. 15. In vivo efficacy of ETx-22 in TNBC PDX400 model. NSG mice were orthotopically implanted bilaterally with tumor fragments. At the indicated time (black arrowhead), the indicated ADC was injected intravenously. The quick score for nectin-4 expression as determined by immuno-histochemistry staining is shown. Bar=500 μm.
Figure 15:
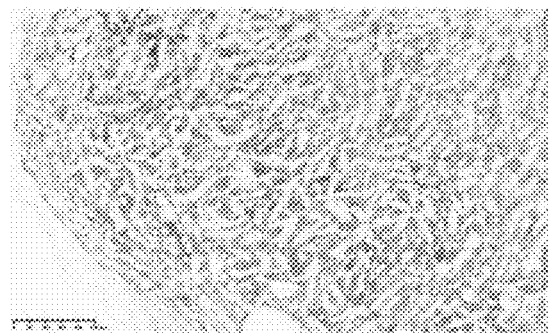
Figure 16:
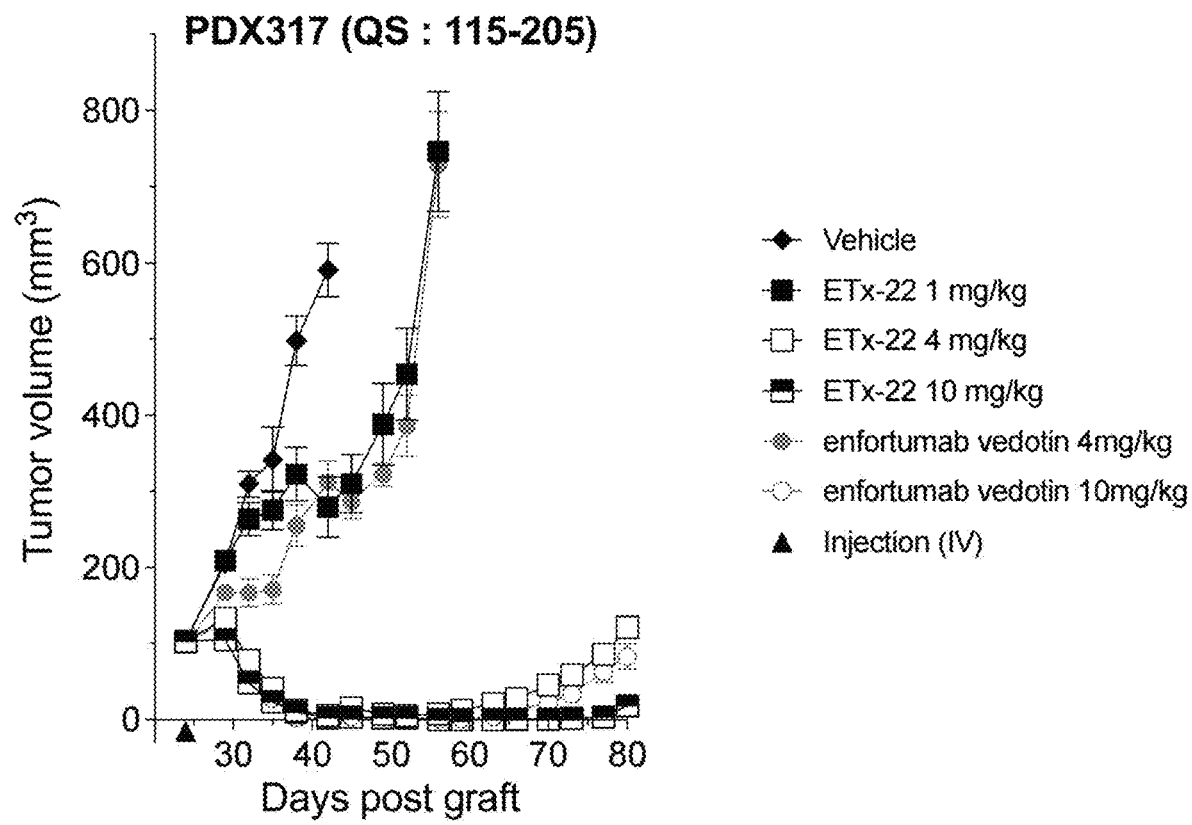
FIG. 16. In vivo efficacy of ETx-22 in TNBC PDX317 model. NSG mice were orthotopically implanted bilaterally with tumor fragments. At the indicated time (black arrowhead), the indicated ADC was injected intravenously. The quick score for nectin-4 expression as determined by immuno-histochemistry staining is shown. Bar=500 μm.
Figure 16:
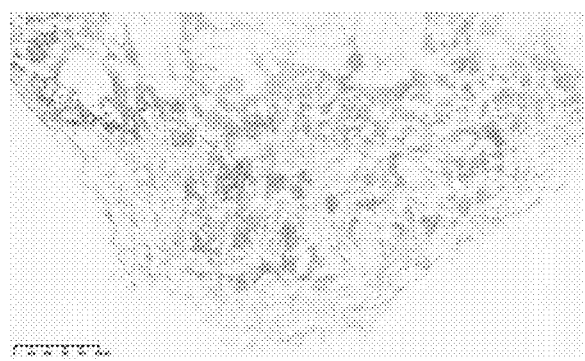
Figure 17:
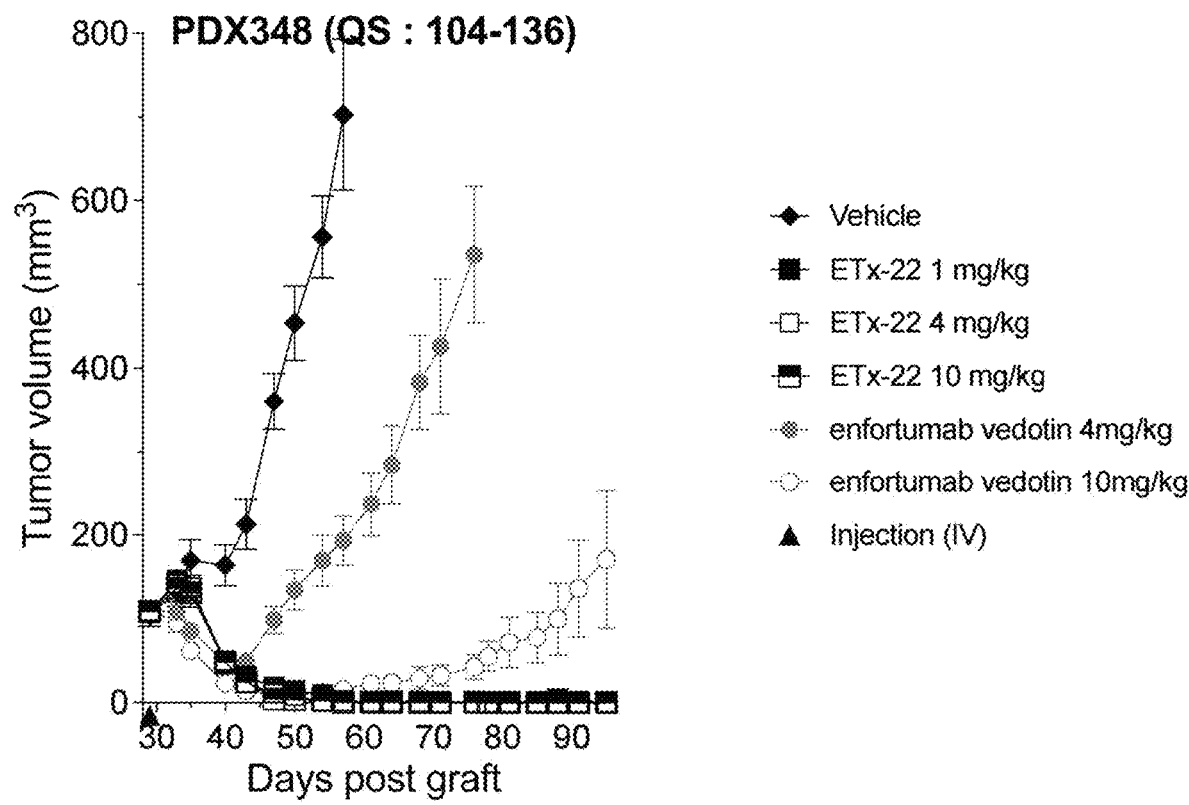
FIG. 17. In vivo efficacy of ETx-22 in TNBC PDX348 model. NSG mice were orthotopically implanted bilaterally with tumor fragments. At the indicated time (black arrowhead), the indicated ADC was injected intravenously. The quick score for nectin-4 expression as determined by immuno-histochemistry staining is shown. Bar=500 μm.
Figure 17:
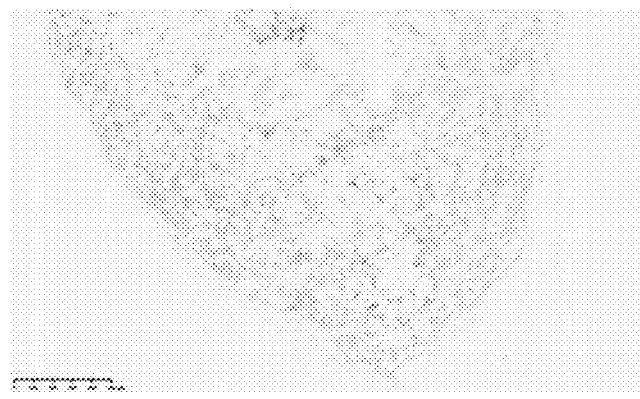
Figure 18:
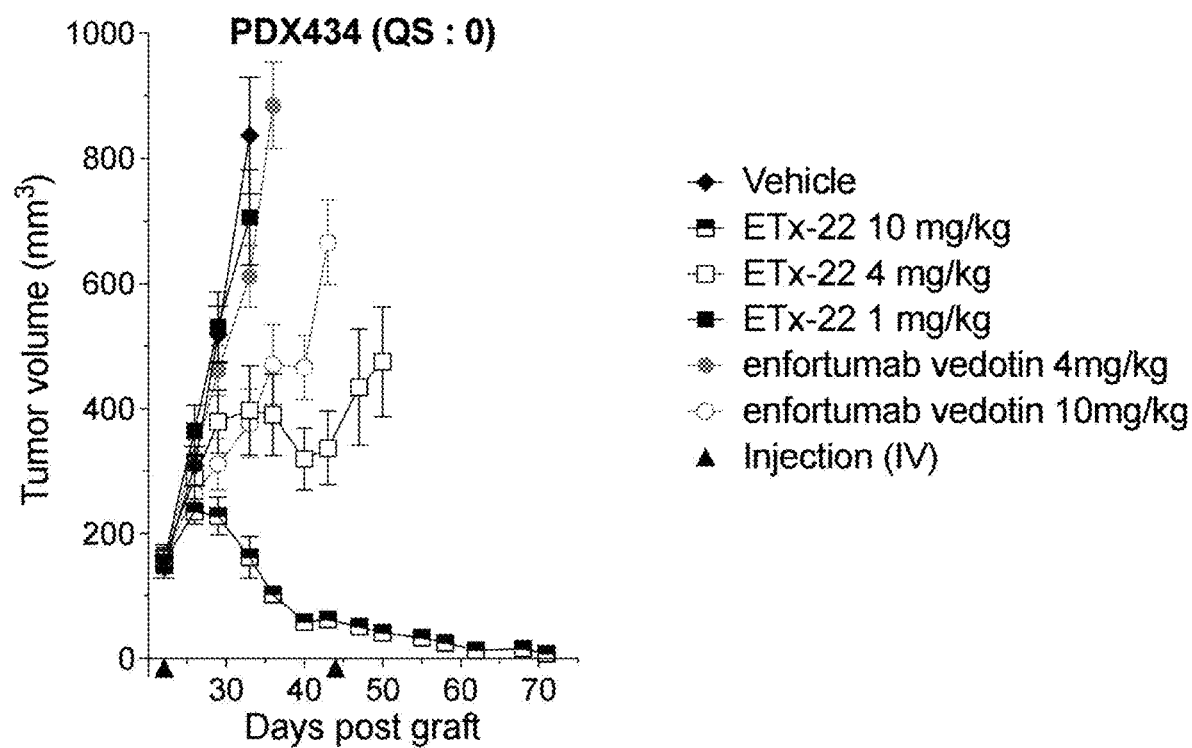
FIG. 18. In vivo efficacy of ETx-22 in TNBC PDX434 model. The TNBC PDX434 model exhibits low Nectin-4 expression. NSG mice were orthotopically implanted bilaterally with tumor fragments. At the indicated time (black arrowhead), the indicated ADC was injected intravenously. The quick score for nectin-4 expression as determined by immuno-histochemistry staining is shown. Bar=500 μm.
Figure 18:
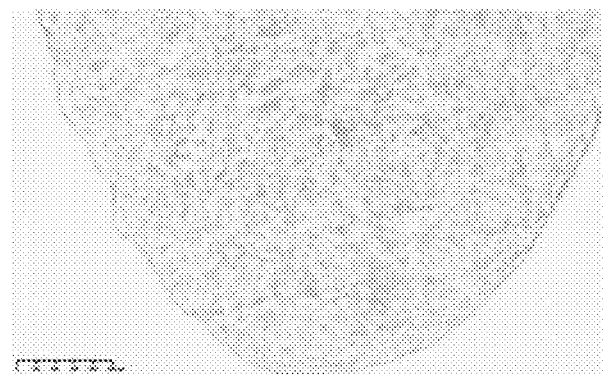

The in vivo efficacy of ETx-22 was assessed in PDX models for triple negative breast cancer (TNBC): PDX400 (FIG. 15 and corresponding Brief Description); PDX 317 (FIG. 16 and corresponding Brief Description); PDX348 (FIG. 17 and corresponding Brief Description); and PDX434 (FIG. 18 and corresponding Brief Description).

AMINO ACID SEQUENCES

| AMINO ACID SEQUENCES |
|---|
| SEQ ID NO: 1<br>MPLSLGAEMWGPEAWLLLLLLLASFTGRCPAGELETSDVVTVVLGQDAKLPCFYRGD<br>SGEQVGQVAWARVDAGEGAQELALLHSKYGLHVSPAYEGRVEQPPPPRNPLDGSVLL<br>RNAVQADEGEYECRVSTFPAGSFQARLRLRVLVPPLPSLNPGPALEEGQGLTLAASCTA<br>EGSPAPSVTWDTEVKGTTSSRSFKHSRSAAVTSEFHLVPSRSMNGQPLTCVVSHPGLLQ<br>DQRITHILHVSFLAEASVRGLEDQNLWHIGREGAMLKCLSEGQPPPSYNWTRLDGPLPS<br>GVRVDGDTLGFPPLTTEHSGIYVCHVSNEFSSRDSQVTVDVLDPQEDSGKQVDLVSAS<br>VVVVGVIAALLFCLLVVVVLMSRYHRRKAQQMTQKYEEELTLTRENSIRRLHSHHT<br>DPRSQPEESVGLRAEGHPDSLKDNSSCSVMSEEPEGRSYSTLTTVREIETQTELLSPGSG<br>RAEEEEDQDEGIKQAMNHFVQENGTLRAKPTGNGIYINGRGHLV |
| SEQ ID NO: 2<br>ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKRVEPKSCDKTHTCPPCPAPELL<br>GGPSVFLFPPKPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKGQPREPQVYTL<br>PPSREEMTKNQVSLTCLVKGFYPSDIAVEWESNGQPENNYKTTPPVLDSDGSFFLYSKL<br>TVDKSRWQQGNVFSCSVMHEALHNHYTQKSLSLSPGK |
| SEQ ID NO: 3<br>ASTKGPSVFPLAPSSKSTSGGTAALGCLVKDYFPEPVTVSWNSGALTSGVHTFPAVLQS<br>SGLYSLSSVVTVPSSSLGTQTYICNVNHKPSNTKVDKRVEPKSCDKTHTCPPCPAPEFEG<br>GPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPASIEKTISKAKGQPREPQVYTLP<br>PSREEMTKNQVSLTCLVKGFYPSDIAVEWESNGQPENNYKTTPPVLDSDGSFFLYSKLT<br>VDKSRWQQGNVFSCSVMHEALHNHYTQKSLSLSPGK |
| SEQ ID NO: 4<br>RTVAAPSVFIFPPSDEQLKSGTASVVCLLNNFYPREAKVQWKVDNALQSGNSQESVTE<br>QDSKDSTYSLSSTLTLSKADYEKHKVYACEVTHQGLSSPVTKSFNRGEC |
| SEQ ID NO: 5<br>EVQLVESGGGLVQPGGSLRLSCAASGFTFSNYGMAWVRQAPGKGLEWVSFISNLAYGI<br>NYADTVTGRFTISRDNAKNSLYLQMNSLRAEDTAVYYCARGARATGWFAYWGQGTL<br>VTVSSASTKGPSVFPLAPSSKSTSGGTAALGCLVKDYFPEPVTVSWNSGALTSGVHTFP<br>AVLQSSGLYSLSSVVTVPSSSLGTQTYICNVNHKPSNTKVDKRVEPKSCDKTHTCPPCP<br>APEFEGGPSVFLFPPKPKDTLMISRTPEVTCVVVDVSHEDPEVKFNWYVDGVEVHNAK<br>TKPREEQYNSTYRVVSVLTVLHQDWLNGKEYKCKVSNKALPASIEKTISKAKGQPREP<br>QVYTLPPSREEMTKNQVSLTCLVKGFYPSDIAVEWESNGQPENNYKTTPPVLDSDGSFF<br>LYSKLTVDKSRWQQGNVFSCSVMHEALHNHYTQKSLSLSPGK |

AMINO ACID SEQUENCES

SEQ ID NO: 6
DIQMTQSPSSLSASVGDRVTITCKASQNVDTHVAWYQQKPGKAPKALIYSASYRYSGV
PSRFSGSGSGTDFTLTISSLQPEDFATYYCQQYNSYPLTFGGGTKVEIKRTVAAPSVFIFP
PSDEQLKSGTASVVCLLNNFYPREAKVQWKVDNALQSGNSQESVTEQDSKDSTYSLSS
TLTLSKADYEKHKVYACEVTHQGLSSPVTKSFNRGEC

SEQ ID NO: 7
EVQLVESGGGLVQPGGSLRLSCAASGFTFSNYGMAWVRQAPGKGLEWVSFISNLAYGI
NYADTVTGRFTISRDNAKNSLYLQMNSLRAEDTAVYYCARGARATGWFAYWGQGTL
VTVSS

SEQ ID NO: 8
DIQMTQSPSSLSASVGDRVTITCKASQNVDTHVAWYQQKPGKAPKALIYSASYRYSGV
PSRFSGSGSGTDFTLTISSLQPEDFATYYCQQYNSYPLTFGGGTKVEIK

SEQ ID NO: 9
NYGMA

SEQ ID NO: 10
FISNLAYGINYADTVTG

SEQ ID NO: 11
GARATGWFAY

SEQ ID NO: 12
KASQNVDTHVA

SEQ ID NO: 13
SASYRYS

SEQ ID NO: 14
QQYNSYPLT

SEQ ID NO: 15
GFTFSNYG

SEQ ID NO: 16
ISNLAYGI

SEQ ID NO: 17
ARGARATGWFAY

SEQ ID NO: 18
QNVDTH

SEQ ID NO: 19
SAS

SEQ ID NO: 20
QQYNSYPLT

SEQUENCE LISTING

```
Sequence total quantity: 20
SEQ ID NO: 1                    moltype = AA   length = 510
FEATURE                         Location/Qualifiers
source                          1..510
                                mol_type = protein
                                organism = synthetic construct
SEQUENCE: 1
MPLSLGAEMW GPEAWLLLLL LLASFTGRCP AGELETSDVV TVVLGQDAKL PCFYRGDSGE   60
QVGQVAWARV DAGEGAQELA LLHSKYGLHV SPAYEGRVEQ PPPPRNPLDG SVLLRNAVQA  120
DEGEYECRVS TFPAGSFQAR LRLRVLVPPL PSLNPGPALE EGQGLTLAAS CTAEGSPAPS  180
VTWDTEVKGT TSSRSFKHSR SAAVTSEFHL VPSRSMNGQP LTCVVSHPGL LQDQRITHIL  240
HVSFLAEASV RGLEDQNLWH IGREGAMLKC LSEGQPPPSY NWTRLDGPLP SGVRVDGDTL  300
GFPPLTTEHS GIYVCHVSNE FSSRDSQVTV DVLDPQEDSG KQVDLVSASV VVVGVIAALL  360
FCLLVVVVL MSRYHRRKAQ QMTQKYEEEL TLTRENSIRR LHSHHTDPRS QPEESVGLRA  420
EGHPDSLKDN SSCSVMSEEP EGRSYSTLTT VREIETQTEL LSPGSGRAEE EEDQDEGIKQ  480
AMNHFVQENG TLRAKPTGNG IYINGRGHLV                                  510

SEQ ID NO: 2                    moltype = AA   length = 330
FEATURE                         Location/Qualifiers
```

```
source                  1..330
                        mol_type = protein
                        organism = synthetic construct
SEQUENCE: 2
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                    330

SEQ ID NO: 3            moltype = AA  length = 330
FEATURE                 Location/Qualifiers
source                  1..330
                        mol_type = protein
                        organism = synthetic construct
SEQUENCE: 3
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPEFEGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPASIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                    330

SEQ ID NO: 4            moltype = AA  length = 107
FEATURE                 Location/Qualifiers
source                  1..107
                        mol_type = protein
                        organism = synthetic construct
SEQUENCE: 4
RTVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                 107

SEQ ID NO: 5            moltype = AA  length = 449
FEATURE                 Location/Qualifiers
source                  1..449
                        mol_type = protein
                        organism = synthetic construct
SEQUENCE: 5
EVQLVESGGG LVQPGGSLRL SCAASGFTFS NYGMAWVRQA PGKGLEWVSF ISNLAYGINY     60
ADTVTGRFTI SRDNAKNSLY LQMNSLRAED TAVYYCARGA RATGWFAYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKRVEPK SCDKTHTCPP CPAPEFEGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PASIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                     449

SEQ ID NO: 6            moltype = AA  length = 214
FEATURE                 Location/Qualifiers
source                  1..214
                        mol_type = protein
                        organism = synthetic construct
SEQUENCE: 6
DIQMTQSPSS LSASVGDRVT ITCKASQNVD THVAWYQQKP GKAPKALIYS ASYRYSGVPS     60
RFSGSGSGTD FTLTISSLQP EDFATYYCQQ YNSYPLTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 7            moltype = AA  length = 119
FEATURE                 Location/Qualifiers
source                  1..119
                        mol_type = protein
                        organism = synthetic construct
SEQUENCE: 7
EVQLVESGGG LVQPGGSLRL SCAASGFTFS NYGMAWVRQA PGKGLEWVSF ISNLAYGINY     60
ADTVTGRFTI SRDNAKNSLY LQMNSLRAED TAVYYCARGA RATGWFAYWG QGTLVTVSS    119

SEQ ID NO: 8            moltype = AA  length = 107
FEATURE                 Location/Qualifiers
source                  1..107
                        mol_type = protein
                        organism = synthetic construct
SEQUENCE: 8
DIQMTQSPSS LSASVGDRVT ITCKASQNVD THVAWYQQKP GKAPKALIYS ASYRYSGVPS     60
RFSGSGSGTD FTLTISSLQP EDFATYYCQQ YNSYPLTFGG GTKVEIK                 107

SEQ ID NO: 9            moltype = AA  length = 5
FEATURE                 Location/Qualifiers
```

```
source                  1..5
                        mol_type = protein
                        organism = synthetic construct
SEQUENCE: 9
NYGMA                                                                           5

SEQ ID NO: 10           moltype = AA  length = 17
FEATURE                 Location/Qualifiers
source                  1..17
                        mol_type = protein
                        organism = synthetic construct
SEQUENCE: 10
FISNLAYGIN YADTVTG                                                              17

SEQ ID NO: 11           moltype = AA  length = 10
FEATURE                 Location/Qualifiers
source                  1..10
                        mol_type = protein
                        organism = synthetic construct
SEQUENCE: 11
GARATGWFAY                                                                      10

SEQ ID NO: 12           moltype = AA  length = 11
FEATURE                 Location/Qualifiers
source                  1..11
                        mol_type = protein
                        organism = synthetic construct
SEQUENCE: 12
KASQNVDTHV A                                                                    11

SEQ ID NO: 13           moltype = AA  length = 7
FEATURE                 Location/Qualifiers
source                  1..7
                        mol_type = protein
                        organism = synthetic construct
SEQUENCE: 13
SASYRYS                                                                         7

SEQ ID NO: 14           moltype = AA  length = 9
FEATURE                 Location/Qualifiers
source                  1..9
                        mol_type = protein
                        organism = synthetic construct
SEQUENCE: 14
QQYNSYPLT                                                                       9

SEQ ID NO: 15           moltype = AA  length = 8
FEATURE                 Location/Qualifiers
source                  1..8
                        mol_type = protein
                        organism = synthetic construct
SEQUENCE: 15
GFTFSNYG                                                                        8

SEQ ID NO: 16           moltype = AA  length = 8
FEATURE                 Location/Qualifiers
source                  1..8
                        mol_type = protein
                        organism = synthetic construct
SEQUENCE: 16
ISNLAYGI                                                                        8

SEQ ID NO: 17           moltype = AA  length = 12
FEATURE                 Location/Qualifiers
source                  1..12
                        mol_type = protein
                        organism = synthetic construct
SEQUENCE: 17
ARGARATGWF AY                                                                   12

SEQ ID NO: 18           moltype = AA  length = 6
FEATURE                 Location/Qualifiers
source                  1..6
                        mol_type = protein
                        organism = synthetic construct
SEQUENCE: 18
QNVDTH                                                                          6

SEQ ID NO: 19           moltype =    length =
```

```
SEQUENCE: 19
000

SEQ ID NO: 20          moltype = AA   length = 9
FEATURE                Location/Qualifiers
source                 1..9
                       mol_type = protein
                       organism = synthetic construct
SEQUENCE: 20
QQYNSYPLT                                                                    9
```

What is claimed is:

1. An antibody-drug conjugate (ADC) of the formula:

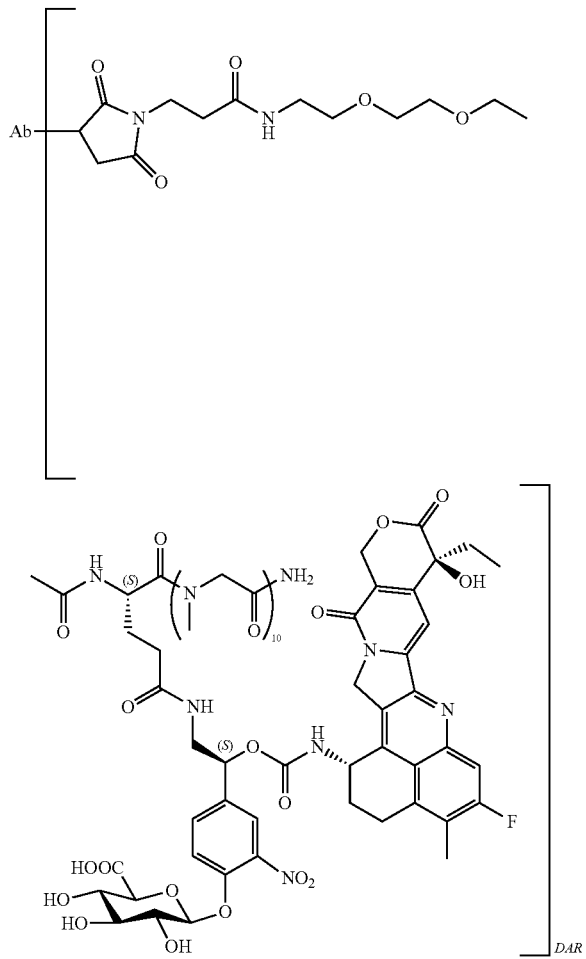

wherein:

Ab is an antibody that binds human Nectin-4 and comprises a heavy chain (HC) and a light chain (LC), wherein:

Ab comprises a HC of SEQ ID NO:5 and a LC of SEQ ID NO:6, DAR is 8, and the Ab is conjugated via cysteines at positions C222, C228, C231 of the HC and via a cysteine of C214 of the LC.

2. The ADC of claim 1, wherein the Ab has a human IgG1 isotype.

3. A composition comprising the ADC of claim 1, wherein at least about 95% of the ADC in the composition has a DAR of 8.

4. A pharmaceutical composition comprising the ADC of claim 1, and one or more pharmaceutically acceptable carriers, diluents, or excipients.

5. A method of treating cancer characterized by expression of Nectin-4, the method comprising administering to a patient in need thereof, an effective amount of the ADC of claim 1.

6. The method of claim 5, wherein the cancer is urothelial carcinoma, breast cancer, lung cancer, gastric cancer, esophageal cancer, colorectal cancer, pancreatic cancer, head and neck cancer, ovarian cancer, or prostate cancer.

7. The method of claim 5, wherein the cancer is urothelial cancer.

8. The method of claim 5, wherein the patient previously was administered enfortumab vedotin as a first-line, second-line, or third-line treatment and the effective amount of the ADC is subsequently administered.

9. The method of claim 8, wherein the cancer has relapsed after enfortumab vedotin was administered as a treatment.

10. The method of claim 8, wherein the cancer has become refractory to treatment with enfortumab vedotin after enfortumab vedotin was administered as a treatment.

11. The method of claim 5, wherein the cancer is resistant to treatment with enfortumab vedotin.

* * * * *

UNITED STATES PATENT AND TRADEMARK OFFICE
CERTIFICATE OF CORRECTION

PATENT NO. : 12,419,964 B2
APPLICATION NO. : 18/904628
DATED : September 23, 2025
INVENTOR(S) : Elands et al.

It is certified that error appears in the above-identified patent and that said Letters Patent is hereby corrected as shown below:

On the Title Page

Column 1, item (71) Applicants, Line 3: Delete "Marseilles" and insert -- Marseille --.

Column 1, item (71) Applicants, Line 7: Delete "Marseilles" and insert -- Marseille --.

Column 1, item (71) Applicants, Line 11: Delete "Lyons" and insert -- Lyon --.

Column 1, item (72) Inventors, Line 3: Delete "Lyons" and insert -- Lyon --.

Column 1, item (72) Inventors, Line 6: Delete "Marseilles" and insert -- Marseille --.

Column 1, item (72) Inventors, Line 7: Delete "Marseilles" and insert -- Marseille --.

Column 1, item (73) Assignees, Line 3: Delete "Marseilles" and insert -- Marseille --.

Column 1, item (73) Assignees, Line 7: Delete "Marseilles" and insert -- Marseille --.

Column 1, item (73) Assignees, Line 11: Delete "Lyons" and insert -- Lyon --.

Signed and Sealed this
Thirteenth Day of January, 2026

John A. Squires
*Director of the United States Patent and Trademark Office*